(12) United States Patent
Buck

(10) Patent No.: US 8,404,806 B2
(45) Date of Patent: Mar. 26, 2013

(54) ISOLATED BRCA1 PEPTIDES AND METHOD OF USE

(75) Inventor: Martina Buck, Del Mar, CA (US)

(73) Assignee: The Regents of the University of California, Oakland, CA (US)

( * ) Notice: Subject to any disclaimer, the term of this patent is extended or adjusted under 35 U.S.C. 154(b) by 193 days.

(21) Appl. No.: 12/849,261

(22) Filed: Aug. 3, 2010

(65) Prior Publication Data

US 2010/0317598 A1 Dec. 16, 2010

Related U.S. Application Data

(63) Continuation of application No. PCT/US2009/033072, filed on Feb. 4, 2009.

(60) Provisional application No. 61/026,154, filed on Feb. 5, 2008, provisional application No. 61/043,176, filed on Apr. 8, 2008.

(51) Int. Cl.
*C07K 1/00* (2006.01)
*C07K 14/00* (2006.01)
*A61K 38/00* (2006.01)
*A61P 35/00* (2006.01)
*C07H 21/02* (2006.01)
*C07H 21/04* (2006.01)

(52) U.S. Cl. ....... 530/350; 514/1.1; 514/19.2; 514/19.3; 536/23.1; 536/23.5

(58) Field of Classification Search .................. None
See application file for complete search history.

(56) References Cited

U.S. PATENT DOCUMENTS

2003/0105000 A1* 6/2003 Pero et al. ...................... 514/12

FOREIGN PATENT DOCUMENTS

WO WO99/50280 A1 10/1999

OTHER PUBLICATIONS

Rudikoff et al. (PNAS, USA, 1982, 79: 1979-1983).*
Coleman et al. (Research in Immunology, 1994; 145(1): 33-36).*
Burgess et al. (J of Cell Bio. 111:2129-2138, 1990).*
Skolnick et al. (TIBTECH 18:34-39, 2000).*
Ibragimova and Eade (Biophysical Journal, Oct. 1999, vol. 77, pp. 2191-2198).*
Holt et al. (Nature Genetics 1996, 12: 298-302).*
Zhang et al., 1998, "BRCA1 Physically Associated with p53 and Stimulates its Transcriptional Activity," Oncogene, vol. 16:1713-1721.
Navaraj et al., 2005, "Cooperation between BRCA1 and p53 in Repair of Cyclobutane Pyrimidine Dimmers," Cancer Biology and Therapy, vol. 4(12):1409-1414.
Thangaraju et al., 2000, "BRCA1 Facilitates Stress-Induced Apoptosis in Breast and Ovarian Cancer Cell Lines," The Journal of biological Chemistry, vol. 275(43):33487-33496.
Buck, 2008, "A Novel Domain of BRCA1 Interacts with p53 in Breast Cancer Cells," Cancer Letters, vol. 268 (1):137-145.
International Search Report for PCT/US2009/033072 dated Jul. 29, 2009 (3 pages).

* cited by examiner

*Primary Examiner* — Peter J Reddig
(74) *Attorney, Agent, or Firm* — Sutherland Asbill & Brennan LLP

(57) ABSTRACT

The invention provides isolated peptides of a BRCA1 domain, which bind to p53 cognate DNA and stimulate transcription activities and cancer cell apoptosis. Nucleic acids encoding the peptides, and methods of expression thereof, are also provided. The invention provides pharmaceutical compositions, and methods of use thereof, for treating breast and ovarian cancer using the peptides.

15 Claims, 7 Drawing Sheets

SEQUENCE LISTING

<160> NUMBER OF SEQ ID NOS: 22

<210> SEQ ID NO 1
<211> LENGTH: 521
<212> TYPE: PRT
<213> ORGANISM: Homo sapiens

<400> SEQUENCE: 1

```
Val Pro Gly Thr Asp Tyr Gly Thr Gln Glu Ser Ile Ser Leu Leu Glu
1               5                   10                  15

Val Ser Thr Leu Gly Lys Ala Lys Thr Glu Pro Asn Lys Cys Val Ser
            20                  25                  30

Gln Cys Ala Ala Phe Glu Asn Pro Lys Gly Leu Ile His Gly Cys Ser
        35                  40                  45

Lys Asp Asn Arg Asn Asp Thr Glu Gly Phe Lys Tyr Pro Leu Gly His
    50                  55                  60

Glu Val Asn His Ser Arg Glu Thr Ser Ile Glu Met Glu Glu Ser Glu
65                  70                  75                  80

Leu Asp Ala Gln Tyr Leu Gln Asn Thr Phe Lys Val Ser Lys Arg Gln
                85                  90                  95

Ser Phe Ala Pro Phe Ser Asn Pro Gly Asn Ala Glu Glu Glu Cys Ala
            100                 105                 110
```

```
Thr Phe Ser Ala His Ser Gly Ser Leu Lys Lys Gln Ser Pro Lys Val
        115                 120                 125

Thr Phe Glu Cys Glu Gln Lys Glu Glu Asn Gln Gly Lys Asn Glu Ser
        130                 135                 140

Asn Ile Lys Pro Val Gln Thr Val Asn Ile Thr Ala Gly Phe Pro Val
145                 150                 155                 160

Val Gly Gln Lys Asp Lys Pro Val Asp Asn Ala Lys Cys Ser Ile Lys
                165                 170                 175

Gly Gly Ser Arg Phe Cys Leu Ser Ser Gln Phe Arg Gly Asn Glu Thr
                180                 185                 190

Gly Leu Ile Thr Pro Asn Lys His Gly Leu Leu Gln Asn Pro Tyr Arg
        195                 200                 205

Ile Pro Pro Leu Phe Pro Ile Lys Ser Phe Val Lys Thr Lys Cys Lys
        210                 215                 220

Lys Asn Leu Leu Glu Glu Asn Phe Glu Glu His Ser Met Ser Pro Glu
225                 230                 235                 240

Arg Glu Met Gly Asn Glu Asn Ile Pro Ser Thr Val Ser Thr Ile Ser
                245                 250                 255

Arg Asn Asn Ile Arg Glu Asn Val Phe Lys Glu Ala Ser Ser Ser Asn
                260                 265                 270

Ile Asn Glu Val Gly Ser Ser Thr Asn Glu Val Gly Ser Ser Ile Asn
        275                 280                 285

Glu Ile Gly Ser Ser Asp Glu Asn Ile Gln Ala Glu Leu Gly Arg Asn
        290                 295                 300

Arg Gly Pro Lys Leu Asn Ala Met Leu Arg Leu Gly Val Leu Gln Pro
305                 310                 315                 320

Glu Val Tyr Lys Gln Ser Leu Pro Gly Ser Asn Cys Lys His Pro Glu
                325                 330                 335

Ile Lys Lys Gln Glu Tyr Glu Glu Val Val Gln Thr Val Asn Thr Asp
                340                 345                 350

Phe Ser Pro Tyr Leu Ile Ser Asp Asn Leu Glu Gln Pro Met Gly Ser
        355                 360                 365

Ser His Ala Ser Gln Val Cys Ser Glu Thr Pro Asp Asp Leu Leu Asp
        370                 375                 380

Asp Gly Glu Ile Lys Glu Asp Thr Ser Phe Ala Glu Asn Asp Ile Lys
385                 390                 395                 400

Glu Ser Ser Ala Val Phe Ser Lys Ser Val Gln Lys Gly Glu Leu Ser
                405                 410                 415

Arg Ser Pro Ser Pro Phe Thr His Thr His Leu Ala Gln Gly Tyr Arg
                420                 425                 430

Arg Gly Ala Lys Lys Leu Glu Ser Ser Glu Glu Asn Leu Ser Ser Glu
                435                 440                 445

Asp Glu Glu Leu Pro Cys Phe Gln His Leu Leu Phe Gly Lys Val Asn
450                 455                 460

Asn Ile Pro Ser Gln Ser Thr Arg His Ser Thr Val Ala Thr Glu Cys
465                 470                 475                 480

Leu Ser Lys Asn Thr Glu Glu Asn Leu Leu Ser Leu Lys Asn Ser Leu
                485                 490                 495

Asn Asp Cys Ser Asn Gln Val Ile Leu Ala Lys Ala Ser Gln Glu His
                500                 505                 510

His Leu Ser Glu Glu Thr Lys Cys Ser
        515                 520
```

```
<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tacagaatcg ctctaagcat gctgggg                                           27

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tacagaacat gtctaagcat gctgggg                                           27

<210> SEQ ID NO 4
<211> LENGTH: 1710
<212> TYPE: PRT
<213> ORGANISM: Homo sapiens

<400> SEQUENCE: 4
```

Met Asp Leu Ser Ala Leu Arg Val Glu Glu Val Gln Asn Val Ile Asn
1               5                   10                  15

Ala Met Gln Lys Ile Leu Glu Cys Pro Ile Cys Leu Glu Leu Ile Lys
            20                  25                  30

Glu Pro Val Ser Thr Lys Cys Asp His Ile Phe Cys Lys Phe Cys Met
        35                  40                  45

Leu Lys Leu Leu Asn Gln Lys Lys Gly Pro Ser Gln Cys Pro Leu Cys
    50                  55                  60

Lys Asn Asp Ile Thr Lys Arg Ser Leu Gln Glu Ser Thr Arg Phe Ser
65                  70                  75                  80

Gln Leu Val Glu Glu Leu Leu Lys Ile Ile Cys Ala Phe Gln Leu Asp
                85                  90                  95

Thr Gly Leu Glu Tyr Ala Asn Ser Tyr Asn Phe Ala Lys Lys Glu Asn
            100                 105                 110

Asn Ser Pro Glu His Leu Lys Asp Glu Val Ser Ile Ile Gln Ser Met
        115                 120                 125

Gly Tyr Arg Asn Arg Ala Lys Arg Leu Leu Gln Ser Glu Pro Glu Asn
    130                 135                 140

Pro Ser Leu Gln Glu Thr Ser Leu Ser Val Gln Leu Ser Asn Leu Gly
145                 150                 155                 160

Thr Val Arg Thr Leu Arg Thr Lys Gln Arg Ile Gln Pro Gln Lys Thr
                165                 170                 175

Ser Val Tyr Ile Glu Leu Gly Ser Asp Ser Ser Glu Asp Thr Val Asn
            180                 185                 190

Lys Ala Thr Tyr Cys Ser Val Gly Asp Gln Glu Leu Leu Gln Ile Thr
        195                 200                 205

Pro Gln Gly Thr Arg Asp Glu Ile Ser Leu Asp Ser Ala Lys Lys Ala
    210                 215                 220

Ala Cys Glu Phe Ser Glu Thr Asp Val Thr Asn Thr Glu His His Gln
225                 230                 235                 240

Pro Ser Asn Asn Asp Leu Asn Thr Thr Glu Lys Arg Ala Ala Glu Arg
                245                 250                 255

```
His Pro Glu Lys Tyr Gln Gly Ser Ser Val Ser Asn Leu His Val Glu
            260                 265                 270
Pro Cys Gly Thr Asn Thr His Ala Ser Ser Leu Gln His Glu Asn Ser
            275                 280                 285
Ser Leu Leu Thr Lys Asp Arg Met Asn Val Glu Lys Ala Glu Phe
290                 295                 300
Cys Asn Lys Ser Lys Gln Pro Gly Leu Ala Arg Ser Gln His Asn Arg
305                 310                 315                 320
Trp Ala Gly Ser Lys Glu Thr Cys Asn Asp Arg Arg Thr Pro Ser Thr
                325                 330                 335
Glu Lys Lys Val Asp Leu Asn Ala Asp Pro Leu Cys Glu Arg Lys Glu
            340                 345                 350
Trp Asn Lys Gln Lys Leu Pro Cys Ser Glu Asn Pro Arg Asp Thr Glu
            355                 360                 365
Asp Val Pro Trp Ile Thr Leu Asn Ser Ser Ile Gln Lys Val Asn Glu
            370                 375                 380
Trp Phe Ser Arg Ser Asp Glu Leu Leu Gly Ser Asp Ser His Asp
385                 390                 395                 400
Gly Glu Ser Glu Ser Asn Ala Lys Val Ala Asp Val Leu Asp Val Leu
                405                 410                 415
Asn Glu Val Asp Glu Tyr Ser Gly Ser Ser Glu Lys Ile Asp Leu Leu
            420                 425                 430
Ala Ser Asp Pro His Glu Ala Leu Ile Cys Lys Ser Glu Arg Val His
            435                 440                 445
Ser Lys Ser Val Glu Ser Asn Ile Glu Asp Lys Ile Phe Gly Lys Thr
450                 455                 460
Tyr Arg Lys Lys Ala Ser Leu Pro Asn Leu Ser His Val Thr Glu Asn
465                 470                 475                 480
Leu Ile Ile Gly Ala Phe Val Thr Glu Pro Gln Ile Ile Gln Glu Arg
                485                 490                 495
Pro Leu Thr Asn Lys Leu Lys Arg Lys Arg Arg Pro Thr Ser Gly Leu
            500                 505                 510
His Pro Glu Asp Phe Ile Lys Lys Ala Asp Leu Ala Val Gln Lys Thr
            515                 520                 525
Pro Glu Met Ile Asn Gln Gly Thr Asn Gln Thr Glu Gln Asn Gly Gln
530                 535                 540
Val Met Asn Ile Thr Asn Ser Gly His Glu Asn Lys Thr Lys Gly Asp
545                 550                 555                 560
Ser Ile Gln Asn Glu Lys Asn Pro Asn Pro Ile Glu Ser Leu Glu Lys
                565                 570                 575
Glu Ser Ala Phe Lys Thr Lys Ala Glu Pro Ile Ser Ser Ser Ile Ser
            580                 585                 590
Asn Met Glu Leu Glu Leu Asn Ile His Asn Ser Lys Ala Pro Lys Lys
            595                 600                 605
Asn Arg Leu Arg Arg Lys Ser Ser Thr Arg His Ile His Ala Leu Glu
            610                 615                 620
Leu Val Val Ser Arg Asn Leu Ser Pro Pro Asn Cys Thr Glu Leu Gln
625                 630                 635                 640
Ile Asp Ser Cys Ser Ser Ser Glu Glu Ile Lys Lys Lys Lys Tyr Asn
                645                 650                 655
Gln Met Pro Val Arg His Ser Arg Asn Leu Gln Leu Met Glu Gly Lys
            660                 665                 670
Glu Pro Ala Thr Gly Ala Lys Lys Ser Asn Lys Pro Asn Glu Gln Thr
```

```
            675                 680                 685
Ser Lys Arg His Asp Ser Asp Thr Phe Pro Glu Leu Lys Leu Thr Asn
690                 695                 700
Ala Pro Gly Ser Phe Thr Lys Cys Ser Asn Thr Ser Glu Leu Lys Glu
705                 710                 715                 720
Phe Val Asn Pro Ser Leu Pro Arg Glu Glu Lys Glu Lys Leu Glu
                725                 730                 735
Thr Val Lys Val Ser Asn Ala Glu Asp Pro Lys Asp Leu Met Leu
            740                 745                 750
Ser Gly Glu Arg Val Leu Gln Thr Glu Arg Ser Val Glu Ser Ser
        755                 760                 765
Ile Ser Leu Val Pro Gly Thr Asp Tyr Gly Thr Gln Glu Ser Ile Ser
770                 775                 780
Leu Leu Glu Val Ser Thr Leu Gly Lys Ala Lys Thr Glu Pro Asn Lys
785                 790                 795                 800
Cys Val Ser Gln Cys Ala Ala Phe Glu Asn Pro Lys Gly Leu Ile His
                805                 810                 815
Gly Cys Ser Lys Asp Asn Arg Asn Asp Thr Glu Gly Phe Lys Tyr Pro
            820                 825                 830
Leu Gly His Glu Val Asn His Ser Arg Glu Thr Ser Ile Glu Met Glu
        835                 840                 845
Glu Ser Glu Leu Asp Ala Gln Tyr Leu Gln Asn Thr Phe Lys Val Ser
    850                 855                 860
Lys Arg Gln Ser Phe Ala Pro Phe Ser Asn Pro Gly Asn Ala Glu Glu
865                 870                 875                 880
Glu Cys Ala Thr Phe Ser Ala His Ser Gly Ser Leu Lys Lys Gln Ser
                885                 890                 895
Pro Lys Val Thr Phe Glu Cys Glu Gln Lys Glu Asn Gln Gly Lys
            900                 905                 910
Asn Glu Ser Asn Ile Lys Pro Val Gln Thr Val Asn Ile Thr Ala Gly
        915                 920                 925
Phe Pro Val Val Gly Gln Lys Asp Lys Pro Val Asp Asn Ala Lys Cys
930                 935                 940
Ser Ile Lys Gly Gly Ser Arg Phe Cys Leu Ser Ser Gln Phe Arg Gly
945                 950                 955                 960
Asn Glu Thr Gly Leu Ile Thr Pro Asn Lys His Gly Leu Leu Gln Asn
                965                 970                 975
Pro Tyr Arg Ile Pro Pro Leu Phe Pro Ile Lys Ser Phe Val Lys Thr
            980                 985                 990
Lys Cys Lys Lys Asn Leu Leu Glu Glu Asn Phe Glu Glu His Ser Met
        995                 1000                1005
Ser Pro Glu Arg Glu Met Gly Asn Glu Asn Ile Pro Ser Thr Val
    1010                1015                1020
Ser Thr Ile Ser Arg Asn Asn Ile Arg Glu Asn Val Phe Lys Glu
    1025                1030                1035
Ala Ser Ser Ser Asn Ile Asn Glu Val Gly Ser Ser Thr Asn Glu
    1040                1045                1050
Val Gly Ser Ser Ile Asn Glu Ile Gly Ser Ser Asp Glu Asn Ile
    1055                1060                1065
Gln Ala Glu Leu Gly Arg Asn Arg Gly Pro Lys Leu Asn Ala Met
    1070                1075                1080
Leu Arg Leu Gly Val Leu Gln Pro Glu Val Tyr Lys Gln Ser Leu
    1085                1090                1095
```

-continued

```
Pro Gly Ser Asn Cys Lys His Pro Glu Ile Lys Lys Gln Glu Tyr
1100                1105                1110

Glu Glu Val Val Gln Thr Val Asn Thr Asp Phe Ser Pro Tyr Leu
1115                1120                1125

Ile Ser Asp Asn Leu Glu Gln Pro Met Gly Ser Ser His Ala Ser
1130                1135                1140

Gln Val Cys Ser Glu Thr Pro Asp Asp Leu Leu Asp Asp Gly Glu
1145                1150                1155

Ile Lys Glu Asp Thr Ser Phe Ala Glu Asn Asp Ile Lys Glu Ser
1160                1165                1170

Ser Ala Val Phe Ser Lys Ser Val Gln Lys Gly Glu Leu Ser Arg
1175                1180                1185

Ser Pro Ser Pro Phe Thr His Thr His Leu Ala Gln Gly Tyr Arg
1190                1195                1200

Arg Gly Ala Lys Lys Leu Glu Ser Ser Glu Glu Asn Leu Ser Ser
1205                1210                1215

Glu Asp Glu Glu Leu Pro Cys Phe Gln His Leu Leu Phe Gly Lys
1220                1225                1230

Val Asn Asn Ile Pro Ser Gln Ser Thr Arg His Ser Thr Val Ala
1235                1240                1245

Thr Glu Cys Leu Ser Lys Asn Thr Glu Glu Asn Leu Leu Ser Leu
1250                1255                1260

Lys Asn Ser Leu Asn Asp Cys Ser Asn Gln Val Ile Leu Ala Lys
1265                1270                1275

Ala Ser Gln Glu His His Leu Ser Glu Glu Thr Lys Cys Ser Ala
1280                1285                1290

Ser Leu Phe Ser Ser Gln Cys Ser Glu Leu Glu Asp Leu Thr Ala
1295                1300                1305

Asn Thr Asn Thr Gln Asp Pro Phe Leu Ile Gly Ser Ser Lys Gln
1310                1315                1320

Met Arg His Gln Ser Glu Ser Gln Gly Val Gly Leu Ser Asp Lys
1325                1330                1335

Glu Leu Val Ser Asp Asp Glu Glu Arg Gly Thr Gly Leu Glu Glu
1340                1345                1350

Asn Asn Gln Glu Glu Gln Ser Met Asp Ser Asn Leu Gly Glu Ala
1355                1360                1365

Ala Ser Gly Cys Glu Ser Glu Thr Ser Val Ser Glu Asp Cys Ser
1370                1375                1380

Gly Leu Ser Ser Gln Ser Asp Ile Leu Thr Thr Gln Gln Arg Asp
1385                1390                1395

Thr Met Gln His Asn Leu Ile Lys Leu Gln Gln Glu Met Ala Glu
1400                1405                1410

Leu Glu Ala Val Leu Glu Gln His Gly Ser Gln Pro Ser Asn Ser
1415                1420                1425

Tyr Pro Ser Ile Ile Ser Asp Ser Ser Ala Leu Glu Asp Leu Arg
1430                1435                1440

Asn Pro Glu Gln Ser Thr Ser Glu Lys Ala Val Leu Thr Ser Gln
1445                1450                1455

Lys Ser Ser Glu Tyr Pro Ile Ser Gln Asn Pro Glu Gly Leu Ser
1460                1465                1470

Ala Asp Lys Phe Glu Val Ser Ala Asp Ser Ser Thr Ser Lys Asn
1475                1480                1485

Lys Glu Pro Gly Val Glu Arg Ser Ser Pro Ser Lys Cys Pro Ser
1490                1495                1500
```

Leu Asp Asp Arg Trp Tyr Met His Ser Cys Ser Gly Ser Leu Gln
    1505                1510                1515

Asn Arg Asn Tyr Pro Ser Gln Glu Leu Ile Lys Val Val Asp
    1520                1525                1530

Val Glu Glu Gln Gln Leu Glu Glu Ser Gly Pro His Asp Leu Thr
    1535                1540                1545

Glu Thr Ser Tyr Leu Pro Arg Gln Asp Leu Glu Gly Thr Pro Tyr
    1550                1555                1560

Leu Glu Ser Gly Ile Ser Leu Phe Ser Asp Asp Pro Glu Ser Asp
    1565                1570                1575

Pro Ser Glu Asp Arg Ala Pro Glu Ser Ala Arg Val Gly Asn Ile
    1580                1585                1590

Pro Ser Ser Thr Ser Ala Leu Lys Val Pro Gln Leu Lys Val Ala
    1595                1600                1605

Glu Ser Ala Gln Ser Pro Ala Ala Ala His Thr Thr Asp Thr Ala
    1610                1615                1620

Gly Tyr Asn Ala Met Glu Glu Ser Val Ser Arg Glu Lys Pro Glu
    1625                1630                1635

Leu Thr Ala Ser Thr Glu Arg Val Asn Lys Arg Met Ser Met Val
    1640                1645                1650

Val Ser Gly Leu Thr Pro Glu Phe Met Leu Val Tyr Lys Phe
    1655                1660                1665

Ala Arg Lys His His Ile Thr Leu Thr Asn Leu Ile Thr Glu Glu
    1670                1675                1680

Thr Thr His Val Val Met Lys Thr Asp Ala Glu Phe Val Cys Glu
    1685                1690                1695

Arg Thr Leu Lys Tyr Phe Leu Gly Ile Ala Gly Gly
    1700                1705                1710

<210> SEQ ID NO 5
<211> LENGTH: 1290
<212> TYPE: PRT
<213> ORGANISM: Homo sapiens

<400> SEQUENCE: 5

Met Asp Leu Ser Ala Leu Arg Val Glu Glu Val Gln Asn Val Ile
1               5                   10                  15

Ala Met Gln Lys Ile Leu Glu Cys Pro Ile Cys Leu Glu Leu Ile Lys
            20                  25                  30

Glu Pro Val Ser Thr Lys Cys Asp His Ile Phe Cys Lys Phe Cys Met
            35                  40                  45

Leu Lys Leu Leu Asn Gln Lys Lys Gly Pro Ser Gln Cys Pro Leu Cys
50                  55                  60

Lys Asn Asp Ile Thr Lys Arg Ser Leu Gln Glu Ser Thr Arg Phe Ser
65                  70                  75                  80

Gln Leu Val Glu Glu Leu Leu Lys Ile Ile Cys Ala Phe Gln Leu Asp
                85                  90                  95

Thr Gly Leu Glu Tyr Ala Asn Ser Tyr Asn Phe Ala Lys Lys Glu Asn
            100                 105                 110

Asn Ser Pro Glu His Leu Lys Asp Glu Val Ser Ile Ile Gln Ser Met
            115                 120                 125

Gly Tyr Arg Asn Arg Ala Lys Arg Leu Leu Gln Ser Glu Pro Glu Asn
            130                 135                 140

Pro Ser Leu Gln Glu Thr Ser Leu Ser Val Gln Leu Ser Asn Leu Gly
145                 150                 155                 160

-continued

```
Thr Val Arg Thr Leu Arg Thr Lys Gln Arg Ile Gln Pro Gln Lys Thr
                165                 170                 175
Ser Val Tyr Ile Glu Leu Gly Ser Asp Ser Glu Asp Thr Val Asn
            180                 185                 190
Lys Ala Thr Tyr Cys Ser Val Gly Asp Gln Glu Leu Leu Gln Ile Thr
                195                 200                 205
Pro Gln Gly Thr Arg Asp Glu Ile Ser Leu Asp Ser Ala Lys Lys Ala
    210                 215                 220
Ala Cys Glu Phe Ser Glu Thr Asp Val Thr Asn Thr Glu His His Gln
225                 230                 235                 240
Pro Ser Asn Asn Asp Leu Asn Thr Thr Glu Lys Arg Ala Ala Glu Arg
                245                 250                 255
His Pro Glu Lys Tyr Gln Gly Ser Ser Val Ser Asn Leu His Val Glu
                260                 265                 270
Pro Cys Gly Thr Asn Thr His Ala Ser Ser Leu Gln His Glu Asn Ser
            275                 280                 285
Ser Leu Leu Leu Thr Lys Asp Arg Met Asn Val Glu Lys Ala Glu Phe
    290                 295                 300
Cys Asn Lys Ser Lys Gln Pro Gly Leu Ala Arg Ser Gln His Asn Arg
305                 310                 315                 320
Trp Ala Gly Ser Lys Glu Thr Cys Asn Asp Arg Arg Thr Pro Ser Thr
                325                 330                 335
Glu Lys Lys Val Asp Leu Asn Ala Asp Pro Leu Cys Glu Arg Lys Glu
                340                 345                 350
Trp Asn Lys Gln Lys Leu Pro Cys Ser Glu Asn Pro Arg Asp Thr Glu
            355                 360                 365
Asp Val Pro Trp Ile Thr Leu Asn Ser Ser Ile Gln Lys Val Asn Glu
    370                 375                 380
Trp Phe Ser Arg Ser Asp Glu Leu Leu Gly Ser Asp Asp Ser His Asp
385                 390                 395                 400
Gly Glu Ser Glu Ser Asn Ala Lys Val Ala Asp Val Leu Asp Val Leu
                405                 410                 415
Asn Glu Val Asp Glu Tyr Ser Gly Ser Ser Glu Lys Ile Asp Leu Leu
                420                 425                 430
Ala Ser Asp Pro His Glu Ala Leu Ile Cys Lys Ser Glu Arg Val His
            435                 440                 445
Ser Lys Ser Val Glu Ser Asn Ile Glu Asp Lys Ile Phe Gly Lys Thr
    450                 455                 460
Tyr Arg Lys Lys Ala Ser Leu Pro Asn Leu Ser His Val Thr Glu Asn
465                 470                 475                 480
Leu Ile Ile Gly Ala Phe Val Thr Glu Pro Gln Ile Ile Gln Glu Arg
                485                 490                 495
Pro Leu Thr Asn Lys Leu Lys Arg Lys Arg Arg Pro Thr Ser Gly Leu
            500                 505                 510
His Pro Glu Asp Phe Ile Lys Lys Ala Asp Leu Ala Val Gln Lys Thr
            515                 520                 525
Pro Glu Met Ile Asn Gln Gly Thr Asn Gln Thr Glu Gln Asn Gly Gln
    530                 535                 540
Val Met Asn Ile Thr Asn Ser Gly His Glu Asn Lys Thr Lys Gly Asp
545                 550                 555                 560
Ser Ile Gln Asn Glu Lys Asn Pro Asn Pro Ile Glu Ser Leu Glu Lys
                565                 570                 575
Glu Ser Ala Phe Thr Lys Ala Glu Pro Ile Ser Ser Ser Ile Ser Asn
```

```
                    580                 585                 590
Met Glu Leu Glu Leu Asn Ile His Asn Ser Lys Ala Pro Lys Lys Asn
                595                 600                 605

Arg Leu Arg Arg Lys Ser Ser Thr Arg His Ile His Ala Leu Glu Leu
            610                 615                 620

Val Val Ser Arg Asn Leu Ser Pro Pro Asn Cys Thr Glu Leu Gln Ile
625                 630                 635                 640

Asp Ser Cys Ser Ser Ser Glu Glu Ile Lys Lys Lys Tyr Asn Gln
                645                 650                 655

Met Pro Val Arg His Ser Arg Asn Leu Gln Leu Met Glu Gly Lys Glu
                660                 665                 670

Pro Ala Thr Gly Ala Lys Lys Ser Asn Lys Pro Asn Glu Gln Thr Ser
                675                 680                 685

Lys His Asp Ser Asp Thr Phe Pro Glu Leu Lys Leu Thr Asn Ala Pro
            690                 695                 700

Gly Ser Phe Thr Lys Cys Ser Asn Thr Ser Glu Leu Lys Glu Phe Val
705                 710                 715                 720

Asn Pro Ser Leu Pro Arg Glu Glu Lys Glu Lys Leu Glu Thr Val
                725                 730                 735

Lys Val Ser Asn Asn Ala Glu Asp Pro Lys Asp Leu Met Leu Ser Gly
                740                 745                 750

Glu Arg Val Leu Gln Thr Glu Arg Ser Val Glu Ser Ser Ile Ser
                755                 760                 765

Leu Val Pro Gly Thr Asp Tyr Gly Thr Gln Glu Ser Ile Ser Leu Leu
            770                 775                 780

Glu Val Ser Thr Leu Gly Lys Ala Lys Thr Glu Pro Asn Lys Cys Val
785                 790                 795                 800

Ser Gln Cys Ala Ala Phe Glu Asn Pro Lys Gly Leu Ile His Gly Cys
                805                 810                 815

Ser Lys Asp Asn Arg Asn Asp Thr Glu Gly Phe Lys Tyr Pro Leu Gly
                820                 825                 830

His Glu Val Asn His Ser Arg Glu Thr Ser Ile Glu Met Glu Glu Ser
            835                 840                 845

Glu Leu Asp Ala Gln Tyr Leu Gln Asn Thr Phe Lys Val Ser Lys Arg
            850                 855                 860

Gln Ser Phe Ala Pro Phe Ser Asn Pro Gly Asn Ala Glu Glu Glu Cys
865                 870                 875                 880

Ala Thr Phe Ser Ala His Ser Gly Ser Leu Lys Lys Gln Ser Pro Lys
                885                 890                 895

Val Thr Phe Glu Cys Glu Gln Lys Glu Glu Asn Gln Gly Lys Asn Glu
                900                 905                 910

Ser Asn Ile Lys Pro Val Gln Thr Val Asn Ile Thr Ala Gly Phe Pro
            915                 920                 925

Val Val Gly Gln Lys Asp Lys Pro Val Asp Asn Ala Lys Cys Ser Ile
            930                 935                 940

Lys Gly Gly Ser Arg Phe Cys Leu Ser Ser Gln Phe Arg Gly Asn Glu
945                 950                 955                 960

Thr Gly Leu Ile Thr Pro Asn Lys His Gly Leu Leu Gln Asn Pro Tyr
                965                 970                 975

Arg Ile Pro Pro Leu Phe Pro Ile Lys Ser Phe Val Lys Thr Lys Cys
            980                 985                 990

Lys Lys Asn Leu Leu Glu Glu Asn  Phe Glu Glu His Ser  Met Ser Pro
            995                 1000                1005
```

```
Glu Arg Glu Met Gly Asn Glu Asn Ile Pro Ser Thr Val Ser Thr
    1010            1015                1020

Ile Ser Arg Asn Asn Ile Arg Glu Asn Val Phe Lys Glu Ala Ser
    1025            1030                1035

Ser Ser Asn Ile Asn Glu Val Gly Ser Ser Thr Asn Glu Val Gly
    1040            1045                1050

Ser Ser Ile Asn Glu Ile Gly Ser Ser Asp Glu Asn Ile Gln Ala
    1055            1060                1065

Glu Leu Gly Arg Asn Arg Gly Pro Lys Leu Asn Ala Met Leu Arg
    1070            1075                1080

Leu Gly Val Leu Gln Pro Glu Val Tyr Lys Gln Ser Leu Pro Gly
    1085            1090                1095

Ser Asn Cys Lys His Pro Glu Ile Lys Lys Gln Glu Tyr Glu Glu
    1100            1105                1110

Val Val Gln Thr Val Asn Thr Asp Phe Ser Pro Tyr Leu Ile Ser
    1115            1120                1125

Asp Asn Leu Glu Gln Pro Met Gly Ser Ser His Ala Ser Gln Val
    1130            1135                1140

Cys Ser Glu Thr Pro Asp Asp Leu Leu Asp Asp Gly Glu Ile Lys
    1145            1150                1155

Glu Asp Thr Ser Phe Ala Glu Asn Asp Ile Lys Glu Ser Ser Ala
    1160            1165                1170

Val Phe Ser Lys Ser Val Gln Lys Gly Glu Leu Ser Arg Ser Pro
    1175            1180                1185

Ser Pro Phe Thr His Thr His Leu Ala Gln Gly Tyr Arg Arg Gly
    1190            1195                1200

Ala Lys Lys Leu Glu Ser Ser Glu Glu Asn Leu Ser Ser Glu Asp
    1205            1210                1215

Glu Glu Leu Pro Cys Phe Gln His Leu Leu Phe Gly Lys Val Asn
    1220            1225                1230

Asn Ile Pro Ser Gln Ser Thr Arg His Ser Thr Val Ala Thr Glu
    1235            1240                1245

Cys Leu Ser Lys Asn Thr Glu Glu Asn Leu Leu Ser Leu Lys Asn
    1250            1255                1260

Ser Leu Asn Asp Cys Ser Asn Gln Val Ile Leu Ala Lys Ala Ser
    1265            1270                1275

Gln Glu His His Leu Ser Glu Glu Thr Lys Cys Ser
    1280            1285                1290

<210> SEQ ID NO 6
<211> LENGTH: 909
<212> TYPE: PRT
<213> ORGANISM: Homo sapiens

<400> SEQUENCE: 6

Met Asp Leu Ser Ala Leu Arg Val Glu Glu Val Gln Asn Val Ile
1               5                   10                  15

Ala Met Gln Lys Ile Leu Glu Cys Pro Ile Cys Leu Glu Leu Ile Lys
            20                  25                  30

Glu Pro Val Ser Thr Lys Cys Asp His Ile Phe Cys Lys Phe Cys Met
                35                  40                  45

Leu Lys Leu Leu Asn Gln Lys Lys Gly Pro Ser Gln Cys Pro Leu Cys
        50                  55                  60

Lys Asn Asp Ile Thr Lys Arg Ser Leu Gln Glu Ser Thr Arg Phe Ser
65                  70                  75                  80
```

```
Gln Leu Val Glu Glu Leu Leu Lys Ile Ile Cys Ala Phe Gln Leu Asp
             85                  90                  95
Thr Gly Leu Glu Tyr Ala Asn Ser Tyr Asn Phe Ala Lys Lys Glu Asn
            100                 105                 110
Asn Ser Pro Glu His Leu Lys Asp Glu Val Ser Ile Ile Gln Ser Met
        115                 120                 125
Gly Tyr Arg Asn Arg Ala Lys Arg Leu Leu Gln Ser Glu Pro Glu Asn
    130                 135                 140
Pro Ser Leu Gln Glu Thr Ser Leu Ser Val Gln Leu Ser Asn Leu Gly
145                 150                 155                 160
Thr Val Arg Thr Leu Arg Thr Lys Gln Arg Ile Gln Pro Gln Lys Thr
                165                 170                 175
Ser Val Tyr Ile Glu Leu Gly Ser Asp Ser Ser Glu Asp Thr Val Asn
            180                 185                 190
Lys Ala Thr Tyr Cys Ser Val Gly Asp Gln Glu Leu Leu Gln Ile Thr
        195                 200                 205
Pro Gln Gly Thr Arg Asp Glu Ile Ser Leu Asp Ser Ala Lys Lys Ala
    210                 215                 220
Ala Cys Glu Phe Ser Glu Thr Asp Val Thr Asn Thr Glu His His Gln
225                 230                 235                 240
Pro Ser Asn Asn Asp Leu Asn Thr Thr Glu Lys Arg Ala Ala Glu Arg
                245                 250                 255
His Pro Glu Lys Tyr Gln Gly Ser Ser Val Ser Asn Leu His Val Glu
            260                 265                 270
Pro Cys Gly Thr Asn Thr His Ala Ser Ser Leu Gln His Glu Asn Ser
        275                 280                 285
Ser Leu Leu Leu Thr Lys Asp Arg Met Asn Val Glu Lys Ala Glu Phe
    290                 295                 300
Cys Asn Lys Ser Lys Gln Pro Gly Leu Ala Arg Ser Gln His Asn Arg
305                 310                 315                 320
Trp Ala Gly Ser Glu Thr Cys Asn Asp Arg Arg Thr Pro Ser Thr Glu
                325                 330                 335
Lys Lys Val Asp Leu Asn Ala Asp Pro Leu Cys Glu Arg Lys Glu Trp
            340                 345                 350
Asn Lys Gln Lys Leu Pro Cys Ser Glu Asn Pro Arg Asp Thr Glu Asp
        355                 360                 365
Val Pro Trp Ile Thr Leu Asn Ser Ser Ile Gln Lys Val Asn Glu Trp
    370                 375                 380
Phe Ser Arg Ser Asp Glu Leu Leu Gly Ser Asp Asp Ser His Asp Gly
385                 390                 395                 400
Glu Ser Glu Ser Asn Ala Lys Val Ala Asp Val Leu Asp Val Leu Asn
                405                 410                 415
Glu Val Asp Glu Tyr Ser Gly Ser Ser Glu Lys Ile Asp Leu Leu Ala
            420                 425                 430
Ser Asp Pro His Glu Ala Leu Ile Cys Lys Ser Glu Arg Val His Ser
        435                 440                 445
Lys Ser Val Glu Ser Asn Ile Glu Asp Lys Ile Phe Gly Lys Thr Tyr
    450                 455                 460
Arg Lys Lys Ala Ser Leu Pro Asn Leu Ser His Val Thr Glu Asn Leu
465                 470                 475                 480
Ile Ile Gly Ala Phe Val Thr Glu Pro Gln Ile Ile Gln Glu Arg Pro
                485                 490                 495
Leu Thr Asn Lys Leu Lys Arg Lys Arg Arg Pro Thr Ser Gly Leu His
            500                 505                 510
```

```
Pro Glu Asp Phe Ile Lys Lys Ala Asp Leu Ala Val Gln Lys Thr Pro
            515                 520                 525
Glu Met Ile Asn Gln Gly Thr Asn Gln Thr Glu Gln Asn Gly Gln Val
        530                 535                 540
Met Asn Ile Thr Asn Ser Gly His Glu Asn Lys Thr Lys Gly Asp Ser
545                 550                 555                 560
Ile Gln Asn Glu Lys Asn Pro Asn Pro Ile Glu Ser Leu Glu Lys Glu
                565                 570                 575
Ser Ala Phe Lys Thr Lys Ala Glu Pro Ile Ser Ser Ile Ser Asn
            580                 585                 590
Met Glu Leu Glu Leu Asn Ile His Asn Ser Lys Ala Pro Lys Lys Asn
        595                 600                 605
Arg Leu Arg Arg Lys Ser Thr Arg His Ile His Ala Leu Glu Leu
    610                 615                 620
Val Val Ser Arg Asn Leu Ser Pro Pro Asn Cys Thr Glu Leu Gln Ile
625                 630                 635                 640
Asp Ser Cys Ser Ser Ser Glu Glu Ile Lys Lys Lys Tyr Asn Gln
                645                 650                 655
Met Pro Val Arg His Ser Arg Asn Leu Gln Leu Met Glu Gly Lys Glu
            660                 665                 670
Pro Ala Thr Gly Ala Lys Lys Ser Asn Lys Pro Asn Glu Gln Thr Ser
        675                 680                 685
Lys Arg His Asp Ser Asp Thr Phe Pro Glu Leu Lys Leu Thr Asn Ala
        690                 695                 700
Pro Gly Ser Phe Thr Lys Cys Ser Asn Thr Ser Glu Leu Lys Glu Phe
705                 710                 715                 720
Val Asn Pro Ser Leu Pro Arg Glu Glu Lys Glu Lys Leu Glu Thr
                725                 730                 735
Val Lys Val Ser Asn Asn Ala Glu Asp Pro Lys Asp Leu Met Leu Ser
            740                 745                 750
Gly Glu Arg Val Leu Gln Thr Glu Arg Ser Val Glu Ser Ser Ser Ile
        755                 760                 765
Ser Leu Val Pro Gly Thr Asp Tyr Gly Thr Gln Glu Ser Ile Ser Leu
        770                 775                 780
Leu Glu Val Ser Thr Leu Gly Lys Ala Lys Thr Glu Pro Asn Lys Cys
785                 790                 795                 800
Val Ser Gln Cys Ala Ala Phe Glu Asn Pro Lys Gly Leu Ile His Gly
                805                 810                 815
Cys Ser Lys Asp Asn Arg Asn Asp Thr Glu Gly Phe Lys Tyr Pro Leu
            820                 825                 830
Gly His Glu Val Asn His Ser Arg Glu Thr Ser Ile Glu Met Glu Glu
        835                 840                 845
Ser Glu Leu Asp Ala Gln Tyr Leu Gln Asn Thr Phe Lys Val Ser Lys
        850                 855                 860
Arg Gln Ser Phe Ala Pro Phe Ser Asn Pro Gly Asn Ala Glu Glu Glu
865                 870                 875                 880
Cys Ala Thr Phe Ser Ala His Ser Gly Ser Leu Lys Lys Gln Ser Pro
                885                 890                 895
Lys Val Thr Phe Glu Cys Glu Gln Lys Glu Glu Asn Gln
            900                 905

<210> SEQ ID NO 7
<211> LENGTH: 471
<212> TYPE: PRT
```

<213> ORGANISM: Homo sapiens

<400> SEQUENCE: 7

Met Asp Leu Ser Ala Leu Arg Val Glu Glu Val Gln Asn Val Ile Asn
1               5                   10                  15

Ala Met Gln Lys Ile Leu Glu Cys Pro Ile Cys Leu Glu Leu Ile Lys
            20                  25                  30

Glu Pro Val Ser Thr Lys Cys Asp His Ile Phe Cys Lys Phe Cys Met
        35                  40                  45

Leu Lys Leu Leu Asn Gln Lys Lys Gly Pro Ser Gln Cys Pro Leu Cys
    50                  55                  60

Lys Asn Asp Ile Thr Lys Arg Ser Leu Gln Glu Ser Thr Arg Phe Ser
65                  70                  75                  80

Gln Leu Val Glu Glu Leu Leu Lys Ile Ile Cys Ala Phe Gln Leu Asp
                85                  90                  95

Thr Gly Leu Glu Tyr Ala Asn Ser Tyr Asn Phe Ala Lys Lys Glu Asn
            100                 105                 110

Asn Ser Pro Glu His Leu Lys Asp Glu Val Ser Ile Ile Gln Ser Met
        115                 120                 125

Gly Tyr Arg Asn Arg Ala Lys Arg Leu Leu Gln Ser Glu Pro Glu Asn
    130                 135                 140

Pro Ser Leu Gln Glu Thr Ser Leu Ser Val Gln Leu Ser Asn Leu Gly
145                 150                 155                 160

Thr Val Arg Thr Leu Arg Thr Lys Gln Arg Ile Gln Pro Gln Lys Thr
                165                 170                 175

Ser Val Tyr Ile Glu Leu Gly Ser Asp Ser Ser Glu Asp Thr Val Asn
            180                 185                 190

Lys Ala Thr Tyr Cys Ser Val Gly Asp Gln Glu Leu Leu Gln Ile Thr
        195                 200                 205

Pro Gln Gly Thr Arg Asp Glu Ile Ser Leu Asp Ser Ala Lys Lys Ala
    210                 215                 220

Ala Cys Glu Phe Ser Glu Thr Asp Val Thr Asn Thr Glu His His Gln
225                 230                 235                 240

Pro Ser Asn Asn Asp Leu Asn Thr Thr Glu Lys Arg Ala Ala Glu Arg
                245                 250                 255

His Pro Glu Lys Tyr Gln Gly Ser Ser Val Ser Asn Leu His Val Glu
            260                 265                 270

Pro Cys Gly Thr Asn Thr His Ala Ser Ser Leu Gln His Glu Asn Ser
        275                 280                 285

Ser Leu Leu Leu Thr Lys Asp Arg Met Asn Val Glu Lys Ala Glu Phe
    290                 295                 300

Cys Asn Lys Ser Lys Gln Pro Gly Leu Ala Arg Ser Gln His Asn Arg
305                 310                 315                 320

Trp Ala Gly Ser Lys Glu Thr Cys Asn Asp Arg Arg Thr Pro Ser Thr
                325                 330                 335

Glu Lys Lys Val Asp Leu Asn Ala Asp Pro Leu Cys Glu Arg Lys Glu
            340                 345                 350

Trp Asn Lys Gln Lys Leu Pro Cys Ser Glu Asn Pro Arg Asp Thr Glu
        355                 360                 365

Asp Val Pro Trp Ile Thr Leu Asn Ser Ser Ile Gln Lys Val Asn Glu
    370                 375                 380

Trp Phe Ser Arg Ser Asp Glu Leu Leu Gly Ser Asp Asp Ser His Asp
385                 390                 395                 400

Gly Glu Ser Glu Ser Asn Ala Lys Val Ala Asp Val Leu Asp Val Leu

```
                405                 410                 415
Asn Glu Val Asp Glu Tyr Ser Gly Ser Ser Glu Lys Ile Asp Leu Ala
            420                 425                 430

Ser Asp Pro His Glu Ala Leu Ile Cys Lys Ser Glu Arg Val His Ser
            435                 440                 445

Lys Ser Val Glu Ser Asn Ile Glu Asp Lys Ile Phe Gly Lys Thr Tyr
            450                 455                 460

Arg Lys Lys Ala Ser Leu Pro
465                 470

<210> SEQ ID NO 8
<211> LENGTH: 266
<212> TYPE: PRT
<213> ORGANISM: Homo sapiens

<400> SEQUENCE: 8

Leu Val Pro Gly Thr Asp Tyr Gly Thr Gln Glu Ser Ile Ser Leu Leu
1               5                   10                  15

Glu Val Ser Thr Leu Gly Lys Ala Lys Thr Glu Pro Asn Lys Cys Val
            20                  25                  30

Ser Gln Cys Ala Ala Phe Glu Asn Pro Lys Gly Leu Ile His Gly Cys
        35                  40                  45

Ser Lys Asp Asn Arg Asn Asp Thr Glu Gly Phe Lys Tyr Pro Leu Gly
    50                  55                  60

His Glu Val Asn His Ser Arg Glu Thr Ser Ile Glu Met Glu Glu Ser
65                  70                  75                  80

Glu Leu Asp Ala Gln Tyr Leu Gln Asn Thr Phe Lys Val Ser Lys Arg
                85                  90                  95

Gln Ser Phe Ala Pro Phe Ser Asn Pro Gly Asn Ala Glu Glu Glu Cys
            100                 105                 110

Ala Thr Phe Ser Ala His Ser Gly Ser Leu Lys Lys Gln Ser Pro Lys
        115                 120                 125

Val Thr Phe Glu Cys Glu Gln Lys Glu Glu Asn Gln Gly Lys Asn Glu
    130                 135                 140

Ser Asn Ile Lys Pro Val Gln Thr Val Asn Ile Thr Ala Gly Phe Pro
145                 150                 155                 160

Val Val Gly Gln Lys Asp Lys Pro Val Asp Asn Ala Lys Cys Ser Ile
                165                 170                 175

Lys Gly Gly Ser Arg Phe Cys Leu Ser Ser Gln Phe Arg Gly Asn Glu
            180                 185                 190

Thr Gly Leu Ile Thr Pro Asn Lys His Gly Leu Leu Gln Asn Pro Tyr
        195                 200                 205

Arg Ile Pro Pro Leu Phe Pro Ile Lys Ser Phe Val Lys Thr Lys Cys
    210                 215                 220

Lys Lys Asn Leu Leu Glu Glu Asn Phe Glu Glu His Ser Met Ser Pro
225                 230                 235                 240

Glu Arg Glu Met Gly Asn Glu Asn Ile Pro Ser Thr Val Ser Thr Ile
                245                 250                 255

Ser Arg Asn Asn Ile Arg Glu Asn Val Phe
            260                 265

<210> SEQ ID NO 9
<211> LENGTH: 307
<212> TYPE: PRT
<213> ORGANISM: Homo sapiens

<400> SEQUENCE: 9
```

Leu Gln Thr Glu Arg Ser Val Glu Ser Ser Ile Ser Leu Val Pro
1               5                   10                  15

Gly Thr Asp Tyr Gly Thr Gln Glu Ser Ile Ser Leu Leu Glu Val Ser
                20                  25                  30

Thr Leu Gly Lys Ala Lys Thr Glu Pro Asn Lys Cys Val Ser Gln Cys
            35                  40                  45

Ala Ala Phe Glu Asn Pro Lys Gly Leu Ile His Gly Cys Ser Lys Asp
    50                  55                  60

Asn Arg Asn Asp Thr Glu Gly Phe Lys Tyr Pro Leu Gly His Glu Val
65                  70                  75                  80

Asn His Ser Arg Glu Thr Ser Ile Glu Met Glu Glu Ser Glu Leu Asp
                85                  90                  95

Ala Gln Tyr Leu Gln Asn Thr Phe Lys Val Ser Lys Arg Gln Ser Phe
                100                 105                 110

Ala Pro Phe Ser Asn Pro Gly Asn Ala Glu Glu Cys Ala Thr Phe
            115                 120                 125

Ser Ala His Ser Gly Ser Leu Lys Lys Gln Ser Pro Lys Val Thr Phe
    130                 135                 140

Glu Cys Glu Gln Lys Glu Glu Asn Gln Gly Lys Asn Glu Ser Asn Ile
145                 150                 155                 160

Lys Pro Val Gln Thr Val Asn Ile Thr Ala Gly Phe Pro Val Val Gly
                165                 170                 175

Gln Lys Asp Lys Pro Val Asp Asn Ala Lys Cys Ser Ile Lys Gly Gly
            180                 185                 190

Ser Arg Phe Cys Leu Ser Ser Gln Phe Arg Gly Asn Glu Thr Gly Leu
    195                 200                 205

Ile Thr Pro Asn Lys His Gly Leu Leu Gln Asn Pro Tyr Arg Ile Pro
                210                 215                 220

Pro Leu Phe Pro Ile Lys Ser Phe Val Lys Thr Lys Cys Lys Lys Asn
225                 230                 235                 240

Leu Leu Glu Glu Asn Phe Glu Glu His Ser Met Ser Pro Glu Arg Glu
                245                 250                 255

Met Gly Asn Glu Asn Ile Pro Ser Thr Val Ser Thr Ile Ser Arg Asn
            260                 265                 270

Asn Ile Arg Glu Asn Val Phe Lys Glu Ala Ser Ser Asn Ile Asn
    275                 280                 285

Glu Val Gly Ser Ser Thr Asn Glu Val Gly Ser Ser Ile Asn Glu Ile
    290                 295                 300

Gly Ser Ser
305

<210> SEQ ID NO 10
<211> LENGTH: 257
<212> TYPE: PRT
<213> ORGANISM: Homo sapiens

<400> SEQUENCE: 10

Phe Lys Glu Ala Ser Ser Asn Ile Asn Glu Val Gly Ser Ser Thr
1               5                   10                  15

Asn Glu Val Gly Ser Ser Ile Asn Glu Ile Gly Ser Ser Asp Glu Asn
                20                  25                  30

Ile Gln Ala Glu Leu Gly Arg Asn Arg Gly Pro Lys Leu Asn Ala Met
            35                  40                  45

Leu Arg Leu Gly Val Leu Gln Pro Glu Val Tyr Lys Gln Ser Leu Pro
    50                  55                  60

```
Gly Ser Asn Cys Lys His Pro Glu Ile Lys Lys Gln Glu Tyr Glu Glu
 65                  70                  75                  80

Val Val Gln Thr Val Asn Thr Asp Phe Ser Pro Tyr Leu Ile Ser Asp
                 85                  90                  95

Asn Leu Glu Gln Pro Met Gly Ser Ser His Ala Ser Gln Val Cys Ser
            100                 105                 110

Glu Thr Pro Asp Asp Leu Leu Asp Asp Gly Glu Ile Lys Glu Asp Thr
        115                 120                 125

Ser Phe Ala Glu Asn Asp Ile Lys Glu Ser Ser Ala Val Phe Ser Lys
    130                 135                 140

Ser Val Gln Lys Gly Glu Leu Ser Arg Ser Pro Ser Pro Phe Thr His
145                 150                 155                 160

Thr His Leu Ala Gln Gly Tyr Arg Arg Gly Ala Lys Lys Leu Glu Ser
                165                 170                 175

Ser Glu Glu Asn Leu Ser Ser Glu Asp Glu Glu Leu Pro Cys Phe Gln
            180                 185                 190

His Leu Leu Phe Gly Lys Val Asn Asn Ile Pro Ser Gln Ser Thr Arg
        195                 200                 205

His Ser Thr Val Ala Thr Glu Cys Leu Ser Lys Asn Thr Glu Glu Asn
    210                 215                 220

Leu Leu Ser Leu Lys Asn Ser Leu Asn Asp Cys Ser Asn Gln Val Ile
225                 230                 235                 240

Leu Ala Lys Ala Ser Gln Glu His His Leu Ser Glu Glu Thr Lys Cys
                245                 250                 255

Ser

<210> SEQ ID NO 11
<211> LENGTH: 389
<212> TYPE: PRT
<213> ORGANISM: Homo sapiens

<400> SEQUENCE: 11

Glu Gln Lys Glu Glu Asn Gln Gly Lys Asn Glu Ser Asn Ile Lys Pro
 1               5                  10                  15

Val Gln Thr Val Asn Ile Thr Ala Gly Phe Pro Val Val Gly Gln Lys
                20                  25                  30

Asp Lys Pro Val Asp Asn Ala Lys Cys Ser Ile Lys Gly Gly Ser Arg
            35                  40                  45

Phe Cys Leu Ser Ser Gln Phe Arg Gly Asn Glu Thr Gly Leu Ile Thr
    50                  55                  60

Pro Asn Lys His Gly Leu Leu Gln Asn Pro Tyr Arg Ile Pro Pro Leu
 65                  70                  75                  80

Phe Pro Ile Lys Ser Phe Val Lys Thr Lys Cys Lys Lys Asn Leu Leu
                85                  90                  95

Glu Glu Asn Phe Glu Glu His Ser Met Ser Pro Glu Arg Glu Met Gly
            100                 105                 110

Asn Glu Asn Ile Pro Ser Thr Val Ser Thr Ile Ser Arg Asn Asn Ile
        115                 120                 125

Arg Glu Asn Val Phe Lys Glu Ala Ser Ser Ser Asn Ile Asn Glu Val
    130                 135                 140

Gly Ser Ser Thr Asn Glu Val Gly Ser Ser Ile Asn Glu Ile Gly Ser
145                 150                 155                 160

Ser Asp Glu Asn Ile Gln Ala Glu Leu Gly Arg Asn Arg Gly Pro Lys
                165                 170                 175
```

```
Leu Asn Ala Met Leu Arg Leu Gly Val Leu Gln Pro Glu Val Tyr Lys
            180                 185                 190

Gln Ser Leu Pro Gly Ser Asn Cys Lys His Pro Glu Ile Lys Lys Gln
        195                 200                 205

Glu Tyr Glu Val Val Gln Thr Val Asn Thr Asp Phe Ser Pro Tyr
    210                 215                 220

Leu Ile Ser Asp Asn Leu Glu Gln Pro Met Gly Ser Ser His Ala Ser
225                 230                 235                 240

Gln Val Cys Ser Glu Thr Pro Asp Asp Leu Leu Asp Asp Gly Glu Ile
                245                 250                 255

Lys Glu Asp Thr Ser Phe Ala Glu Asn Asp Ile Lys Glu Ser Ser Ala
            260                 265                 270

Val Phe Ser Lys Ser Val Gln Lys Gly Glu Leu Ser Arg Ser Pro Ser
        275                 280                 285

Pro Phe Thr His Thr His Leu Ala Gln Gly Tyr Arg Arg Gly Ala Lys
    290                 295                 300

Lys Leu Glu Ser Ser Glu Glu Asn Leu Ser Ser Glu Asp Glu Glu Leu
305                 310                 315                 320

Pro Cys Phe Gln His Leu Leu Phe Gly Lys Val Asn Asn Ile Pro Ser
                325                 330                 335

Gln Ser Thr Arg His Ser Thr Val Ala Thr Glu Cys Leu Ser Lys Asn
            340                 345                 350

Thr Glu Glu Asn Leu Leu Ser Leu Lys Asn Ser Leu Asn Asp Cys Ser
        355                 360                 365

Asn Gln Val Ile Leu Ala Lys Ala Ser Gln Glu His His Leu Ser Glu
    370                 375                 380

Glu Thr Lys Cys Ser
385

<210> SEQ ID NO 12
<211> LENGTH: 1409
<212> TYPE: PRT
<213> ORGANISM: Homo sapiens

<400> SEQUENCE: 12

Met Asp Leu Ser Ala Leu Arg Val Glu Glu Val Gln Asn Val Ile Asn
1               5                   10                  15

Ala Met Gln Lys Ile Leu Glu Cys Pro Ile Cys Leu Glu Leu Ile Lys
            20                  25                  30

Glu Pro Val Ser Thr Lys Cys Asp His Ile Phe Cys Lys Phe Cys Met
        35                  40                  45

Leu Lys Leu Leu Asn Gln Lys Lys Gly Pro Ser Gln Cys Pro Leu Cys
    50                  55                  60

Lys Asn Asp Ile Thr Lys Arg Ser Leu Gln Glu Ser Thr Arg Phe Ser
65                  70                  75                  80

Gln Leu Val Glu Glu Leu Leu Lys Ile Ile Cys Ala Phe Gln Leu Asp
                85                  90                  95

Thr Gly Leu Glu Tyr Ala Asn Ser Tyr Asn Phe Ala Lys Lys Glu Asn
            100                 105                 110

Asn Ser Pro Glu His Leu Lys Asp Glu Val Ser Ile Ile Gln Ser Met
        115                 120                 125

Gly Tyr Arg Asn Arg Ala Lys Arg Leu Leu Gln Ser Glu Pro Glu Asn
    130                 135                 140

Pro Ser Leu Gln Glu Thr Ser Leu Ser Val Gln Leu Ser Asn Leu Gly
145                 150                 155                 160
```

-continued

Thr Val Arg Thr Leu Arg Thr Lys Gln Arg Ile Gln Pro Gln Lys Thr
            165                 170                 175

Ser Val Tyr Ile Glu Leu Gly Ser Asp Ser Ser Glu Asp Thr Val Asn
            180                 185                 190

Lys Ala Thr Tyr Cys Ser Val Gly Asp Gln Glu Leu Leu Gln Ile Thr
            195                 200                 205

Pro Gln Gly Thr Arg Asp Glu Ile Ser Leu Asp Ser Ala Lys Lys Ala
            210                 215                 220

Ala Cys Glu Phe Ser Glu Thr Asp Val Thr Asn Thr Glu His His Gln
225                 230                 235                 240

Pro Ser Asn Asn Asp Leu Asn Thr Thr Glu Lys Arg Ala Ala Glu Arg
            245                 250                 255

His Pro Glu Lys Tyr Gln Gly Ser Ser Val Ser Asn Leu His Val Glu
            260                 265                 270

Pro Cys Gly Thr Asn Thr His Ala Ser Ser Leu Gln His Glu Asn Ser
            275                 280                 285

Ser Leu Leu Leu Thr Lys Asp Arg Met Asn Val Glu Lys Ala Glu Phe
            290                 295                 300

Cys Asn Lys Ser Lys Gln Pro Gly Leu Ala Arg Ser Gln His Asn Arg
305                 310                 315                 320

Trp Ala Gly Ser Lys Glu Thr Cys Asn Asp Arg Arg Thr Pro Ser Thr
            325                 330                 335

Glu Lys Lys Val Asp Leu Asn Ala Asp Pro Leu Cys Glu Arg Lys Glu
            340                 345                 350

Trp Asn Lys Gln Lys Leu Pro Cys Ser Glu Asn Pro Arg Asp Thr Glu
            355                 360                 365

Asp Val Pro Trp Ile Thr Leu Asn Ser Ser Ile Gln Lys Val Asn Glu
            370                 375                 380

Trp Phe Ser Arg Ser Asp Glu Leu Leu Gly Ser Asp Asp Ser His Asp
385                 390                 395                 400

Gly Glu Ser Glu Ser Asn Ala Lys Val Ala Asp Val Leu Asp Val Leu
            405                 410                 415

Asn Glu Val Asp Glu Tyr Ser Gly Ser Ser Glu Lys Ile Asp Leu Leu
            420                 425                 430

Ala Ser Asp Pro His Glu Ala Leu Ile Cys Lys Ser Glu Arg Val His
            435                 440                 445

Ser Lys Ser Val Glu Ser Asn Ile Glu Asp Lys Ile Phe Gly Lys Thr
            450                 455                 460

Tyr Arg Lys Lys Ala Ser Leu Pro Asn Leu Ser His Val Thr Glu Asn
465                 470                 475                 480

Leu Ile Ile Gly Ala Phe Val Thr Glu Pro Gln Ile Ile Gln Glu Arg
            485                 490                 495

Pro Leu Thr Asn Lys Leu Lys Arg Lys Arg Arg Pro Thr Ser Gly Leu
            500                 505                 510

His Pro Glu Asp Phe Ile Lys Lys Ala Asp Leu Ala Val Gln Lys Thr
            515                 520                 525

Pro Glu Met Ile Asn Gln Gly Thr Asn Gln Thr Glu Gln Asn Gly Gln
            530                 535                 540

Val Met Asn Ile Thr Asn Ser Gly His Glu Asn Lys Thr Lys Gly Asp
545                 550                 555                 560

Ser Ile Gln Asn Glu Lys Asn Pro Asn Pro Ile Glu Ser Leu Glu Lys
            565                 570                 575

Glu Ser Ala Phe Lys Thr Lys Ala Glu Pro Ile Ser Ser Ser Ile Ser
            580                 585                 590

```
Asn Met Glu Leu Glu Leu Asn Ile His Asn Ser Lys Ala Pro Lys Lys
        595                 600                 605

Asn Arg Leu Arg Arg Lys Ser Ser Thr Arg His Ile His Ala Leu Glu
    610                 615                 620

Leu Val Val Ser Arg Asn Leu Ser Pro Pro Asn Cys Thr Glu Leu Gln
625                 630                 635                 640

Ile Asp Ser Cys Ser Ser Ser Glu Glu Ile Lys Lys Lys Lys Tyr Asn
                645                 650                 655

Gln Met Pro Val Arg His Ser Arg Asn Leu Gln Leu Met Glu Gly Lys
            660                 665                 670

Glu Pro Ala Thr Gly Ala Lys Lys Ser Asn Lys Pro Asn Glu Gln Thr
        675                 680                 685

Ser Lys Arg His Asp Ser Asp Thr Phe Pro Glu Leu Lys Leu Thr Asn
    690                 695                 700

Ala Pro Gly Ser Phe Thr Lys Cys Ser Asn Thr Ser Glu Leu Lys Glu
705                 710                 715                 720

Phe Val Asn Pro Ser Leu Pro Arg Glu Glu Lys Glu Glu Lys Leu Glu
                725                 730                 735

Thr Val Lys Val Ser Asn Asn Ala Glu Asp Pro Lys Asp Leu Met Leu
            740                 745                 750

Ser Gly Glu Arg Val Leu Gln Thr Glu Arg Ser Val Glu Ser Ser Ser
        755                 760                 765

Ile Ser Leu Val Pro Gly Thr Asp Tyr Gly Thr Gln Glu Ser Ile Ser
    770                 775                 780

Leu Leu Glu Val Ser Thr Leu Gly Lys Ala Lys Thr Glu Pro Asn Lys
785                 790                 795                 800

Cys Val Ser Gln Cys Ala Ala Phe Glu Asn Pro Lys Gly Leu Ile His
                805                 810                 815

Gly Cys Ser Lys Asp Asn Arg Asn Asp Thr Glu Gly Phe Lys Tyr Pro
            820                 825                 830

Leu Gly His Glu Val Asn His Ser Arg Glu Thr Ser Ile Glu Met Glu
        835                 840                 845

Glu Ser Glu Leu Asp Ala Gln Tyr Leu Gln Asn Thr Phe Lys Val Ser
    850                 855                 860

Lys Arg Gln Ser Phe Ala Pro Phe Ser Asn Pro Gly Asn Ala Glu Glu
865                 870                 875                 880

Glu Cys Ala Thr Phe Ser Ala His Ser Gly Ser Leu Lys Lys Gln Ser
                885                 890                 895

Pro Lys Val Thr Phe Glu Cys Glu Gln Lys Glu Glu Asn Gln Gly Lys
            900                 905                 910

Asn Glu Ser Asn Ile Lys Pro Val Gln Thr Val Asn Ile Thr Ala Gly
        915                 920                 925

Phe Pro Val Val Gly Gln Lys Asp Lys Pro Val Asp Asn Ala Lys Cys
    930                 935                 940

Ser Ile Lys Gly Gly Ser Arg Phe Cys Leu Ser Ser Gln Phe Arg Gly
945                 950                 955                 960

Asn Glu Thr Gly Leu Ile Thr Pro Asn Lys His Gly Leu Leu Gln Asn
                965                 970                 975

Pro Tyr Arg Ile Pro Pro Leu Phe Pro Ile Lys Ser Phe Val Lys Thr
            980                 985                 990

Lys Cys Lys Lys Asn Leu Leu Glu Glu Asn Phe Glu Glu His Ser Met
        995                 1000                1005

Ser Pro Glu Arg Glu Met Gly Asn Glu Asn Ile Pro Ser Thr Val
```

```
               1010                1015               1020

Ser Thr Ile Ser Arg Asn Asn  Ile Arg Glu Asn Val  Phe Lys Glu
    1025                1030                1035

Ala Ser Ser Ser Asn Ile Asn  Glu Val Gly Ser Ser  Thr Asn Glu
    1040                1045                1050

Val Gly Ser Ser Ile Asn Glu  Ile Gly Ser Ser Asp  Glu Asn Ile
    1055                1060                1065

Gln Ala Glu Leu Gly Arg Asn  Arg Gly Pro Lys Leu  Asn Ala Met
    1070                1075                1080

Leu Arg Leu Gly Val Leu Gln  Pro Glu Val Tyr Lys  Gln Ser Leu
    1085                1090                1095

Pro Gly Ser Asn Cys Lys His  Pro Glu Ile Lys Lys  Gln Glu Tyr
    1100                1105                1110

Glu Glu Val Val Gln Thr Val  Asn Thr Asp Phe Ser  Pro Tyr Leu
    1115                1120                1125

Ile Ser Asp Asn Leu Glu Gln  Pro Met Gly Ser Ser  His Ala Ser
    1130                1135                1140

Gln Val Cys Ser Glu Thr Pro  Asp Asp Leu Leu Asp  Asp Gly Glu
    1145                1150                1155

Ile Lys Glu Asp Thr Ser Phe  Ala Glu Asn Asp Ile  Lys Glu Ser
    1160                1165                1170

Ser Ala Val Phe Ser Lys Ser  Val Gln Lys Gly Glu  Leu Ser Arg
    1175                1180                1185

Ser Pro Ser Pro Phe Thr His  Thr His Leu Ala Gln  Gly Tyr Arg
    1190                1195                1200

Arg Gly Ala Lys Lys Leu Glu  Ser Ser Glu Glu Asn  Leu Ser Ser
    1205                1210                1215

Glu Asp Glu Glu Leu Pro Cys  Phe Gln His Leu Leu  Phe Gly Lys
    1220                1225                1230

Val Asn Asn Ile Pro Ser Gln  Ser Thr Arg His Ser  Thr Val Ala
    1235                1240                1245

Thr Glu Cys Leu Ser Lys Asn  Thr Glu Glu Asn Leu  Leu Ser Leu
    1250                1255                1260

Lys Asn Ser Leu Asn Asp Cys  Ser Asn Gln Val Ile  Leu Ala Lys
    1265                1270                1275

Ala Ser Gln Glu His His Leu  Ser Glu Glu Thr Lys  Cys Ser Ala
    1280                1285                1290

Ser Leu Phe Ser Ser Gln Cys  Ser Glu Leu Glu Asp  Leu Thr Ala
    1295                1300                1305

Asn Thr Asn Thr Gln Asp Pro  Phe Leu Ile Gly Ser  Ser Lys Gln
    1310                1315                1320

Met Arg His Gln Ser Glu Ser  Gln Gly Val Gly Leu  Ser Asp Lys
    1325                1330                1335

Glu Leu Val Ser Asp Asp Glu  Glu Arg Gly Thr Gly  Leu Glu Glu
    1340                1345                1350

Asn Asn Gln Glu Glu Gln Ser  Met Asp Ser Asn Leu  Gly Glu Ala
    1355                1360                1365

Ala Ser Gly Cys Glu Ser Glu  Thr Ser Val Ser Glu  Asp Cys Ser
    1370                1375                1380

Gly Leu Ser Ser Gln Ser Asp  Ile Leu Thr Thr Gln  Gln Arg Asp
    1385                1390                1395

Thr Met Gln His Asn Leu Ile  Lys Leu Gln Gln
    1400                1405
```

<210> SEQ ID NO 13
<211> LENGTH: 1755
<212> TYPE: PRT
<213> ORGANISM: Homo sapiens

<400> SEQUENCE: 13

```
Lys Lys Glu Asn Asn Ser Pro Glu His Leu Lys Asp Glu Val Ser Ile
1               5                   10                  15

Ile Gln Ser Met Gly Tyr Arg Asn Arg Ala Lys Arg Leu Leu Gln Ser
            20                  25                  30

Glu Pro Glu Asn Pro Ser Leu Gln Glu Thr Ser Leu Ser Val Gln Leu
        35                  40                  45

Ser Asn Leu Gly Thr Val Arg Thr Leu Arg Thr Arg Lys Gln Arg Ile Gln
50                  55                  60

Pro Gln Lys Thr Ser Val Tyr Ile Glu Leu Gly Ser Asp Ser Ser Glu
65                  70                  75                  80

Asp Thr Val Asn Lys Ala Thr Tyr Cys Ser Val Gly Asp Gln Glu Leu
                85                  90                  95

Leu Gln Ile Thr Pro Gln Gly Thr Arg Asp Glu Ile Ser Leu Asp Ser
            100                 105                 110

Ala Lys Lys Ala Ala Cys Glu Phe Ser Glu Thr Asp Val Thr Asn Thr
        115                 120                 125

Glu His His Gln Pro Ser Asn Asn Asp Leu Asn Thr Thr Glu Lys Arg
130                 135                 140

Ala Ala Glu Arg His Pro Glu Lys Tyr Gln Gly Ser Ser Val Ser Asn
145                 150                 155                 160

Leu His Val Glu Pro Cys Gly Thr Asn Thr His Ala Ser Ser Leu Gln
                165                 170                 175

His Glu Asn Ser Ser Leu Leu Leu Thr Lys Asp Arg Met Asn Val Glu
            180                 185                 190

Lys Ala Glu Phe Cys Asn Lys Ser Lys Gln Pro Gly Leu Ala Arg Ser
        195                 200                 205

Gln His Asn Arg Trp Ala Gly Ser Lys Glu Thr Cys Asn Asp Arg Arg
210                 215                 220

Thr Pro Ser Thr Glu Lys Lys Val Asp Leu Asn Ala Asp Pro Leu Cys
225                 230                 235                 240

Glu Arg Lys Glu Trp Asn Lys Gln Lys Leu Pro Cys Ser Glu Asn Pro
                245                 250                 255

Arg Asp Thr Glu Asp Val Pro Trp Ile Thr Leu Asn Ser Ser Ile Gln
            260                 265                 270

Lys Val Asn Glu Trp Phe Ser Arg Ser Asp Glu Leu Leu Gly Ser Asp
        275                 280                 285

Asp Ser His Asp Gly Glu Ser Glu Ser Asn Ala Lys Val Ala Asp Val
290                 295                 300

Leu Asp Val Leu Asn Glu Val Asp Glu Tyr Ser Gly Ser Ser Glu Lys
305                 310                 315                 320

Ile Asp Leu Leu Ala Ser Asp Pro His Glu Ala Leu Ile Cys Lys Ser
                325                 330                 335

Glu Arg Val His Ser Lys Ser Val Glu Ser Asn Ile Glu Asp Lys Ile
            340                 345                 350

Phe Gly Lys Thr Tyr Arg Lys Lys Ala Ser Leu Pro Asn Leu Ser His
        355                 360                 365

Val Thr Glu Asn Leu Ile Ile Gly Ala Phe Val Thr Glu Pro Gln Ile
370                 375                 380
```

```
Ile Gln Glu Arg Pro Leu Thr Asn Lys Leu Lys Arg Lys Arg Pro
385                 390                 395                 400

Thr Ser Gly Leu His Pro Glu Asp Phe Ile Lys Lys Ala Asp Leu Ala
            405                 410                 415

Val Gln Lys Thr Pro Glu Met Ile Asn Gln Gly Thr Asn Gln Thr Glu
        420                 425                 430

Gln Asn Gly Gln Val Met Asn Ile Thr Asn Ser Gly His Glu Asn Lys
            435                 440                 445

Thr Lys Gly Asp Ser Ile Gln Asn Glu Lys Asn Pro Asn Pro Ile Glu
        450                 455                 460

Ser Leu Glu Lys Glu Ser Ala Phe Lys Thr Lys Ala Glu Pro Ile Ser
465                 470                 475                 480

Ser Ser Ile Ser Asn Met Glu Leu Glu Leu Asn Ile His Asn Ser Lys
            485                 490                 495

Ala Pro Lys Lys Asn Arg Leu Arg Arg Lys Ser Ser Thr Arg His Ile
        500                 505                 510

His Ala Leu Glu Leu Val Val Ser Arg Asn Leu Ser Pro Pro Asn Cys
    515                 520                 525

Thr Glu Leu Gln Ile Asp Ser Cys Ser Ser Ser Glu Glu Ile Lys Lys
    530                 535                 540

Lys Lys Tyr Asn Gln Met Pro Val Arg His Ser Arg Asn Leu Gln Leu
545                 550                 555                 560

Met Glu Gly Lys Glu Pro Ala Thr Gly Ala Lys Lys Ser Asn Lys Pro
                565                 570                 575

Asn Glu Gln Thr Ser Lys Arg His Asp Ser Asp Thr Phe Pro Glu Leu
            580                 585                 590

Lys Leu Thr Asn Ala Pro Gly Ser Phe Thr Lys Cys Ser Asn Thr Ser
        595                 600                 605

Glu Leu Lys Glu Phe Val Asn Pro Ser Leu Pro Arg Glu Glu Lys Glu
            610                 615                 620

Glu Lys Leu Glu Thr Val Lys Val Ser Asn Asn Ala Glu Asp Pro Lys
625                 630                 635                 640

Asp Leu Met Leu Ser Gly Glu Arg Val Leu Gln Thr Glu Arg Ser Val
                645                 650                 655

Glu Ser Ser Ser Ile Ser Leu Val Pro Gly Thr Asp Tyr Gly Thr Gln
            660                 665                 670

Glu Ser Ile Ser Leu Leu Glu Val Ser Thr Leu Gly Lys Ala Lys Thr
        675                 680                 685

Glu Pro Asn Lys Cys Val Ser Gln Cys Ala Ala Phe Glu Asn Pro Lys
        690                 695                 700

Gly Leu Ile His Gly Cys Ser Lys Asp Asn Arg Asn Asp Thr Glu Gly
705                 710                 715                 720

Phe Lys Tyr Pro Leu Gly His Glu Val Asn His Ser Arg Glu Thr Ser
                725                 730                 735

Ile Glu Met Glu Glu Ser Glu Leu Asp Ala Gln Tyr Leu Gln Asn Thr
            740                 745                 750

Phe Lys Val Ser Lys Arg Gln Ser Phe Ala Pro Phe Ser Asn Pro Gly
        755                 760                 765

Asn Ala Glu Glu Glu Cys Ala Thr Phe Ser Ala His Ser Gly Ser Leu
        770                 775                 780

Lys Lys Gln Ser Pro Lys Val Thr Phe Glu Cys Glu Gln Lys Glu Glu
785                 790                 795                 800

Asn Gln Gly Lys Asn Glu Ser Asn Ile Lys Pro Val Gln Thr Val Asn
                805                 810                 815
```

```
Ile Thr Ala Gly Phe Pro Val Val Gly Gln Lys Asp Lys Pro Val Asp
                820                 825                 830

Asn Ala Lys Cys Ser Ile Lys Gly Gly Ser Arg Phe Cys Leu Ser Ser
            835                 840                 845

Gln Phe Arg Gly Asn Glu Thr Gly Leu Ile Thr Pro Asn Lys His Gly
    850                 855                 860

Leu Leu Gln Asn Pro Tyr Arg Ile Pro Pro Leu Phe Pro Ile Lys Ser
865                 870                 875                 880

Phe Val Lys Thr Lys Cys Lys Lys Asn Leu Leu Glu Glu Asn Phe Glu
                885                 890                 895

Glu His Ser Met Ser Pro Glu Arg Glu Met Gly Asn Glu Asn Ile Pro
                900                 905                 910

Ser Thr Val Ser Thr Ile Ser Arg Asn Asn Ile Arg Glu Asn Val Phe
                915                 920                 925

Lys Glu Ala Ser Ser Ser Asn Ile Asn Glu Val Gly Ser Ser Thr Asn
            930                 935                 940

Glu Val Gly Ser Ser Ile Asn Glu Ile Gly Ser Ser Asp Glu Asn Ile
945                 950                 955                 960

Gln Ala Glu Leu Gly Arg Asn Arg Gly Pro Lys Leu Asn Ala Met Leu
                965                 970                 975

Arg Leu Gly Val Leu Gln Pro Glu Val Tyr Lys Gln Ser Leu Pro Gly
                980                 985                 990

Ser Asn Cys Lys His Pro Glu Ile Lys Lys Gln Glu Tyr Glu Glu Val
            995                 1000                1005

Val Gln Thr Val Asn Thr Asp Phe Ser Pro Tyr Leu Ile Ser Asp
    1010                1015                1020

Asn Leu Glu Gln Pro Met Gly Ser Ser His Ala Ser Gln Val Cys
    1025                1030                1035

Ser Glu Thr Pro Asp Asp Leu Leu Asp Asp Gly Glu Ile Lys Glu
    1040                1045                1050

Asp Thr Ser Phe Ala Glu Asn Asp Ile Lys Glu Ser Ser Ala Val
    1055                1060                1065

Phe Ser Lys Ser Val Gln Lys Gly Glu Leu Ser Arg Ser Pro Ser
    1070                1075                1080

Pro Phe Thr His Thr His Leu Ala Gln Gly Tyr Arg Arg Gly Ala
    1085                1090                1095

Lys Lys Leu Glu Ser Ser Glu Glu Asn Leu Ser Ser Glu Asp Glu
    1100                1105                1110

Glu Leu Pro Cys Phe Gln His Leu Leu Phe Gly Lys Val Asn Asn
    1115                1120                1125

Ile Pro Ser Gln Ser Thr Arg His Ser Thr Val Ala Thr Glu Cys
    1130                1135                1140

Leu Ser Lys Asn Thr Glu Glu Asn Leu Leu Ser Leu Lys Asn Ser
    1145                1150                1155

Leu Asn Asp Cys Ser Asn Gln Val Ile Leu Ala Lys Ala Ser Gln
    1160                1165                1170

Glu His His Leu Ser Glu Glu Thr Lys Cys Ser Ala Ser Leu Phe
    1175                1180                1185

Ser Ser Gln Cys Ser Glu Leu Glu Asp Leu Thr Ala Asn Thr Asn
    1190                1195                1200

Thr Gln Asp Pro Phe Leu Ile Gly Ser Ser Lys Gln Met Arg His
    1205                1210                1215

Gln Ser Glu Ser Gln Gly Val Gly Leu Ser Asp Lys Glu Leu Val
```

-continued

```
              1220            1225            1230

Ser  Asp  Asp  Glu  Glu  Arg  Gly  Thr  Gly  Leu  Glu  Glu  Asn  Asn  Gln
              1235                 1240                 1245

Glu  Glu  Gln  Ser  Met  Asp  Ser  Asn  Leu  Gly  Glu  Ala  Ala  Ser  Gly
              1250                 1255                 1260

Cys  Glu  Ser  Glu  Thr  Ser  Val  Ser  Glu  Asp  Cys  Ser  Gly  Leu  Ser
              1265                 1270                 1275

Ser  Gln  Ser  Asp  Ile  Leu  Thr  Thr  Gln  Gln  Arg  Asp  Thr  Met  Gln
              1280                 1285                 1290

His  Asn  Leu  Ile  Lys  Leu  Gln  Gln  Glu  Met  Ala  Glu  Leu  Glu  Ala
              1295                 1300                 1305

Val  Leu  Glu  Gln  His  Gly  Ser  Gln  Pro  Ser  Asn  Ser  Tyr  Pro  Ser
              1310                 1315                 1320

Ile  Ile  Ser  Asp  Ser  Ser  Ala  Leu  Glu  Asp  Leu  Arg  Asn  Pro  Glu
              1325                 1330                 1335

Gln  Ser  Thr  Ser  Glu  Lys  Ala  Val  Leu  Thr  Ser  Gln  Lys  Ser  Ser
              1340                 1345                 1350

Glu  Tyr  Pro  Ile  Ser  Gln  Asn  Pro  Glu  Gly  Leu  Ser  Ala  Asp  Lys
              1355                 1360                 1365

Phe  Glu  Val  Ser  Ala  Asp  Ser  Ser  Thr  Ser  Lys  Asn  Lys  Glu  Pro
              1370                 1375                 1380

Gly  Val  Glu  Arg  Ser  Ser  Pro  Ser  Lys  Cys  Pro  Ser  Leu  Asp  Asp
              1385                 1390                 1395

Arg  Trp  Tyr  Met  His  Ser  Cys  Ser  Gly  Ser  Leu  Gln  Asn  Arg  Asn
              1400                 1405                 1410

Tyr  Pro  Ser  Gln  Glu  Glu  Leu  Ile  Lys  Val  Val  Asp  Val  Glu  Glu
              1415                 1420                 1425

Gln  Gln  Leu  Glu  Glu  Ser  Gly  Pro  His  Asp  Leu  Thr  Glu  Thr  Ser
              1430                 1435                 1440

Tyr  Leu  Pro  Arg  Gln  Asp  Leu  Glu  Gly  Thr  Pro  Tyr  Leu  Glu  Ser
              1445                 1450                 1455

Gly  Ile  Ser  Leu  Phe  Ser  Asp  Asp  Pro  Glu  Ser  Asp  Pro  Ser  Glu
              1460                 1465                 1470

Asp  Arg  Ala  Pro  Glu  Ser  Ala  Arg  Val  Gly  Asn  Ile  Pro  Ser  Ser
              1475                 1480                 1485

Thr  Ser  Ala  Leu  Lys  Val  Pro  Gln  Leu  Lys  Val  Ala  Glu  Ser  Ala
              1490                 1495                 1500

Gln  Ser  Pro  Ala  Ala  Ala  His  Thr  Thr  Asp  Thr  Ala  Gly  Tyr  Asn
              1505                 1510                 1515

Ala  Met  Glu  Glu  Ser  Val  Ser  Arg  Glu  Lys  Pro  Glu  Leu  Thr  Ala
              1520                 1525                 1530

Ser  Thr  Glu  Arg  Val  Asn  Lys  Arg  Met  Ser  Met  Val  Val  Ser  Gly
              1535                 1540                 1545

Leu  Thr  Pro  Glu  Glu  Phe  Met  Leu  Val  Tyr  Lys  Phe  Ala  Arg  Lys
              1550                 1555                 1560

His  His  Ile  Thr  Leu  Thr  Asn  Leu  Ile  Thr  Glu  Glu  Thr  Thr  His
              1565                 1570                 1575

Val  Val  Met  Lys  Thr  Asp  Ala  Glu  Phe  Val  Cys  Glu  Arg  Thr  Leu
              1580                 1585                 1590

Lys  Tyr  Phe  Leu  Gly  Ile  Ala  Gly  Gly  Lys  Trp  Val  Val  Ser  Tyr
              1595                 1600                 1605

Phe  Trp  Val  Thr  Gln  Ser  Ile  Lys  Glu  Arg  Lys  Met  Leu  Asn  Glu
              1610                 1615                 1620
```

-continued

```
His Asp Phe Glu Val Arg Gly Asp Val Val Asn Gly Arg Asn His
1625                1630                1635

Gln Gly Pro Lys Arg Ala Arg Glu Ser Gln Asp Arg Lys Ile Phe
1640                1645                1650

Arg Gly Leu Glu Ile Cys Cys Tyr Gly Pro Phe Thr Asn Met Pro
1655                1660                1665

Thr Asp Gln Leu Glu Trp Met Val Gln Leu Cys Gly Ala Ser Val
1670                1675                1680

Val Lys Glu Leu Ser Ser Phe Thr Leu Gly Thr Gly Val His Pro
1685                1690                1695

Ile Val Val Val Gln Pro Asp Ala Trp Thr Glu Asp Asn Gly Phe
1700                1705                1710

His Ala Ile Gly Gln Met Cys Glu Ala Pro Val Val Thr Arg Glu
1715                1720                1725

Trp Val Leu Asp Ser Val Ala Leu Tyr Gln Cys Gln Glu Leu Asp
1730                1735                1740

Thr Tyr Leu Ile Pro Gln Ile Pro His Ser His Tyr
1745                1750                1755

<210> SEQ ID NO 14
<211> LENGTH: 572
<212> TYPE: PRT
<213> ORGANISM: Homo sapiens

<400> SEQUENCE: 14

Ser Ala Ser Leu Phe Ser Ser Gln Cys Ser Glu Leu Glu Asp Leu Thr
1               5                   10                  15

Ala Asn Thr Asn Thr Gln Asp Pro Phe Leu Ile Gly Ser Ser Lys Gln
            20                  25                  30

Met Arg His Gln Ser Glu Ser Gln Gly Val Gly Leu Ser Asp Lys Glu
        35                  40                  45

Leu Val Ser Asp Asp Glu Glu Arg Gly Thr Gly Leu Glu Glu Asn Asn
    50                  55                  60

Gln Glu Glu Gln Ser Met Asp Ser Asn Leu Gly Glu Ala Ala Ser Gly
65                  70                  75                  80

Cys Glu Ser Glu Thr Ser Val Ser Glu Asp Cys Ser Gly Leu Ser Ser
                85                  90                  95

Gln Ser Asp Ile Leu Thr Thr Gln Gln Arg Asp Thr Met Gln His Asn
            100                 105                 110

Leu Ile Lys Leu Gln Gln Glu Met Ala Glu Leu Glu Ala Val Leu Glu
        115                 120                 125

Gln His Gly Ser Gln Pro Ser Asn Ser Tyr Pro Ser Ile Ile Ser Asp
    130                 135                 140

Ser Ser Ala Leu Glu Asp Leu Arg Asn Pro Glu Gln Ser Thr Ser Glu
145                 150                 155                 160

Lys Ala Val Leu Thr Ser Gln Lys Ser Ser Glu Tyr Pro Ile Ser Gln
                165                 170                 175

Asn Pro Glu Gly Leu Ser Ala Asp Lys Phe Glu Val Ser Ala Asp Ser
            180                 185                 190

Ser Thr Ser Lys Asn Lys Glu Pro Gly Val Glu Arg Ser Ser Pro Ser
        195                 200                 205

Lys Cys Pro Ser Leu Asp Asp Arg Trp Tyr Met His Ser Cys Ser Gly
    210                 215                 220

Ser Leu Gln Asn Arg Asn Tyr Pro Ser Gln Glu Glu Leu Ile Lys Val
225                 230                 235                 240
```

-continued

```
Val Asp Val Glu Glu Gln Gln Leu Glu Glu Ser Gly Pro His Asp Leu
                245                 250                 255

Thr Glu Thr Ser Tyr Leu Pro Arg Gln Asp Leu Glu Gly Thr Pro Tyr
            260                 265                 270

Leu Glu Ser Gly Ile Ser Leu Phe Ser Asp Pro Glu Ser Asp Pro
        275                 280                 285

Ser Glu Asp Arg Ala Pro Glu Ser Ala Arg Val Gly Asn Ile Pro Ser
290                 295                 300

Ser Thr Ser Ala Leu Lys Val Pro Gln Leu Lys Val Ala Glu Ser Ala
305                 310                 315                 320

Gln Ser Pro Ala Ala Ala His Thr Thr Asp Thr Ala Gly Tyr Asn Ala
                325                 330                 335

Met Glu Glu Ser Val Ser Arg Glu Lys Pro Glu Leu Thr Ala Ser Thr
            340                 345                 350

Glu Arg Val Asn Lys Arg Met Ser Met Val Val Ser Gly Leu Thr Pro
        355                 360                 365

Glu Glu Phe Met Leu Val Tyr Lys Phe Ala Arg Lys His His Ile Thr
370                 375                 380

Leu Thr Asn Leu Ile Thr Glu Glu Thr Thr His Val Val Met Lys Thr
385                 390                 395                 400

Asp Ala Glu Phe Val Cys Glu Arg Thr Leu Lys Tyr Phe Leu Gly Ile
                405                 410                 415

Ala Gly Gly Lys Trp Val Val Ser Tyr Phe Trp Val Thr Gln Ser Ile
            420                 425                 430

Lys Glu Arg Lys Met Leu Asn Glu His Asp Phe Glu Val Arg Gly Asp
        435                 440                 445

Val Val Asn Gly Arg Asn His Gln Gly Pro Lys Arg Ala Arg Glu Ser
450                 455                 460

Gln Asp Arg Lys Ile Phe Arg Gly Leu Glu Ile Cys Cys Tyr Gly Pro
465                 470                 475                 480

Phe Thr Asn Met Pro Thr Asp Gln Leu Glu Trp Met Val Gln Leu Cys
                485                 490                 495

Gly Ala Ser Val Val Lys Glu Leu Ser Ser Phe Thr Leu Gly Thr Gly
            500                 505                 510

Val His Pro Ile Val Val Gln Pro Asp Ala Trp Thr Glu Asp Asn
        515                 520                 525

Gly Phe His Ala Ile Gly Gln Met Cys Glu Ala Pro Val Val Thr Arg
530                 535                 540

Glu Trp Val Leu Asp Ser Val Ala Leu Tyr Gln Cys Gln Glu Leu Asp
545                 550                 555                 560

Thr Tyr Leu Ile Pro Gln Ile Pro His Ser His Tyr
                565                 570

<210> SEQ ID NO 15
<211> LENGTH: 20
<212> TYPE: PRT
<213> ORGANISM: Homo sapiens

<400> SEQUENCE: 15

Ala Ile Gly Gln Met Cys Glu Ala Pro Val Val Thr Arg Glu Trp Val
1               5                   10                  15

Leu Asp Ser Val
            20

<210> SEQ ID NO 16
<211> LENGTH: 1250
```

```
<212> TYPE: PRT
<213> ORGANISM: Homo sapiens

<400> SEQUENCE: 16
```

Met Asp Leu Ser Ala Leu Arg Val Glu Glu Val Gln Asn Val Ile Asn
1               5                   10                  15

Ala Met Gln Lys Ile Leu Glu Cys Pro Ile Cys Leu Glu Leu Ile Lys
            20                  25                  30

Glu Pro Val Ser Thr Lys Cys Asp His Ile Phe Cys Lys Phe Cys Met
        35                  40                  45

Leu Lys Leu Leu Asn Gln Lys Lys Gly Pro Ser Gln Cys Pro Leu Cys
50                  55                  60

Lys Asn Asp Ile Thr Lys Arg Ser Leu Gln Glu Ser Thr Arg Phe Ser
65                  70                  75                  80

Gln Leu Val Glu Glu Leu Leu Lys Ile Ile Cys Ala Phe Gln Leu Asp
                85                  90                  95

Thr Gly Leu Glu Tyr Ala Asn Ser Tyr Asn Phe Ala Lys Lys Glu Asn
            100                 105                 110

Asn Ser Pro Glu His Leu Lys Asp Glu Val Ser Ile Ile Gln Ser Met
        115                 120                 125

Gly Tyr Arg Asn Arg Ala Lys Arg Leu Leu Gln Ser Glu Pro Glu Asn
130                 135                 140

Pro Ser Leu Gln Glu Thr Ser Leu Ser Val Gln Leu Ser Asn Leu Gly
145                 150                 155                 160

Thr Val Arg Thr Leu Arg Thr Lys Gln Arg Ile Gln Pro Gln Lys Thr
                165                 170                 175

Ser Val Tyr Ile Glu Leu Gly Ser Asp Ser Ser Glu Asp Thr Val Asn
            180                 185                 190

Lys Ala Thr Tyr Cys Ser Val Gly Asp Gln Glu Leu Leu Gln Ile Thr
        195                 200                 205

Pro Gln Gly Thr Arg Asp Glu Ile Ser Leu Asp Ser Ala Lys Lys Ala
210                 215                 220

Ala Cys Glu Phe Ser Glu Thr Asp Val Thr Asn Thr Glu His His Gln
225                 230                 235                 240

Pro Ser Asn Asn Asp Leu Asn Thr Thr Glu Lys Arg Ala Ala Glu Arg
                245                 250                 255

His Pro Glu Lys Tyr Gln Gly Ser Ser Val Ser Asn Leu His Val Glu
            260                 265                 270

Pro Cys Gly Thr Asn Thr His Ala Ser Ser Leu Gln His Glu Asn Ser
        275                 280                 285

Ser Leu Leu Leu Thr Lys Asp Arg Met Asn Val Glu Lys Ala Glu Phe
290                 295                 300

Cys Asn Lys Ser Lys Gln Pro Gly Leu Ala Arg Ser Gln His Asn Arg
305                 310                 315                 320

Trp Ala Gly Ser Lys Glu Thr Cys Asn Asp Arg Arg Thr Pro Ser Thr
                325                 330                 335

Glu Lys Lys Val Asp Leu Asn Ala Asp Pro Leu Cys Glu Arg Lys Glu
            340                 345                 350

Trp Asn Lys Gln Lys Leu Pro Cys Ser Glu Asn Pro Arg Asp Thr Glu
        355                 360                 365

Asp Val Pro Trp Ile Thr Leu Asn Ser Ser Ile Gln Lys Val Asn Glu
370                 375                 380

Trp Phe Ser Arg Ser Asp Glu Leu Leu Gly Ser Asp Asp Ser His Asp
385                 390                 395                 400

```
Gly Glu Ser Glu Ser Asn Ala Lys Val Ala Asp Val Leu Asp Val Leu
                405                 410                 415

Asn Glu Val Asp Glu Tyr Ser Gly Ser Ser Lys Ile Asp Leu Leu
            420                 425                 430

Ala Ser Asp Pro His Glu Ala Leu Ile Cys Lys Ser Glu Arg Val His
            435                 440                 445

Ser Lys Ser Val Glu Ser Asn Ile Glu Asp Lys Ile Phe Gly Lys Thr
        450                 455                 460

Tyr Arg Lys Lys Ala Ser Leu Pro Asn Leu Ser His Val Thr Glu Asn
465                 470                 475                 480

Leu Ile Ile Gly Ala Phe Val Thr Glu Pro Gln Ile Ile Gln Glu Arg
                485                 490                 495

Pro Leu Thr Asn Lys Leu Lys Arg Lys Arg Pro Thr Ser Gly Leu
            500                 505                 510

His Pro Glu Asp Phe Ile Lys Lys Ala Asp Leu Ala Val Gln Lys Thr
        515                 520                 525

Pro Glu Met Ile Asn Gln Gly Thr Asn Gln Thr Glu Gln Asn Gly Gln
            530                 535                 540

Val Met Asn Ile Thr Asn Ser Gly His Glu Asn Lys Thr Lys Gly Asp
545                 550                 555                 560

Ser Ile Gln Asn Glu Lys Asn Pro Asn Pro Ile Glu Ser Leu Glu Lys
                565                 570                 575

Glu Ser Ala Phe Lys Thr Lys Ala Glu Pro Ile Ser Ser Ser Ile Ser
            580                 585                 590

Asn Met Glu Leu Glu Leu Asn Ile His Asn Ser Lys Ala Pro Lys Lys
        595                 600                 605

Asn Arg Leu Arg Arg Lys Ser Ser Thr Arg His Ile His Ala Leu Glu
610                 615                 620

Leu Val Val Ser Arg Asn Leu Ser Pro Pro Asn Cys Thr Glu Leu Gln
625                 630                 635                 640

Ile Asp Ser Cys Ser Ser Ser Glu Glu Ile Lys Lys Lys Lys Tyr Asn
                645                 650                 655

Gln Met Pro Val Arg His Ser Arg Asn Leu Gln Leu Met Glu Gly Lys
            660                 665                 670

Glu Pro Ala Thr Gly Ala Lys Lys Ser Asn Lys Pro Asn Glu Gln Thr
        675                 680                 685

Ser Lys Arg His Asp Ser Asp Thr Phe Pro Glu Leu Lys Leu Thr Asn
        690                 695                 700

Ala Pro Gly Ser Phe Thr Lys Cys Ser Asn Thr Ser Glu Leu Lys Glu
705                 710                 715                 720

Phe Val Asn Pro Ser Leu Pro Arg Glu Glu Lys Glu Glu Lys Leu Glu
                725                 730                 735

Thr Val Lys Val Ser Asn Asn Ala Glu Asp Pro Lys Asp Leu Met Leu
            740                 745                 750

Ser Gly Glu Arg Val Leu Gln Thr Glu Arg Ser Val Glu Ser Ser Ser
        755                 760                 765

Ile Ser Leu Val Pro Gly Thr Asp Tyr Gly Thr Gln Glu Ser Ile Ser
        770                 775                 780

Leu Leu Glu Val Ser Thr Leu Gly Lys Ala Lys Thr Glu Pro Asn Lys
785                 790                 795                 800

Cys Val Ser Gln Cys Ala Ala Phe Glu Asn Pro Lys Gly Leu Ile His
                805                 810                 815

Gly Cys Ser Lys Asp Asn Arg Asn Asp Thr Glu Gly Phe Lys Tyr Pro
            820                 825                 830
```

-continued

Leu Gly His Glu Val Asn His Ser Arg Glu Thr Ser Ile Glu Met Glu
        835                 840                 845

Glu Ser Glu Leu Asp Ala Gln Tyr Leu Gln Asn Thr Phe Lys Val Ser
    850                 855                 860

Lys Arg Gln Ser Phe Ala Pro Phe Ser Asn Pro Gly Asn Ala Glu Glu
865                 870                 875                 880

Glu Cys Ala Thr Phe Ser Ala His Ser Gly Ser Leu Lys Lys Gln Ser
                885                 890                 895

Pro Lys Val Thr Phe Glu Cys Glu Gln Lys Glu Glu Asn Gln Gly Lys
            900                 905                 910

Asn Glu Ser Asn Ile Lys Pro Val Gln Thr Val Asn Ile Thr Ala Gly
        915                 920                 925

Phe Pro Val Val Gly Gln Lys Asp Lys Pro Val Asp Asn Ala Lys Cys
    930                 935                 940

Ser Ile Lys Gly Gly Ser Arg Phe Cys Leu Ser Ser Gln Phe Arg Gly
945                 950                 955                 960

Asn Glu Thr Gly Leu Ile Thr Pro Asn Lys His Gly Leu Leu Gln Asn
                965                 970                 975

Pro Tyr Arg Ile Pro Pro Leu Phe Pro Ile Lys Ser Phe Val Lys Thr
            980                 985                 990

Lys Cys Lys Lys Asn Leu Leu Glu Glu Asn Phe Glu Glu His Ser Met
        995                 1000                1005

Ser Pro Glu Arg Glu Met Gly Asn Glu Asn Ile Pro Ser Thr Val
    1010                1015                1020

Ser Thr Ile Ser Arg Asn Asn Ile Arg Glu Asn Val Phe Lys Glu
    1025                1030                1035

Ala Ser Ser Ser Asn Ile Asn Glu Val Gly Ser Ser Thr Asn Glu
    1040                1045                1050

Val Gly Ser Ser Ile Asn Glu Ile Gly Ser Ser Asp Glu Asn Ile
    1055                1060                1065

Gln Ala Glu Leu Gly Arg Asn Arg Gly Pro Lys Leu Asn Ala Met
    1070                1075                1080

Leu Arg Leu Gly Val Leu Gln Pro Glu Val Tyr Lys Gln Ser Leu
    1085                1090                1095

Pro Gly Ser Asn Cys Lys His Pro Glu Ile Lys Lys Gln Glu Tyr
    1100                1105                1110

Glu Glu Val Val Gln Thr Val Asn Thr Asp Phe Ser Pro Tyr Leu
    1115                1120                1125

Ile Ser Asp Asn Leu Glu Gln Pro Met Gly Ser Ser His Ala Ser
    1130                1135                1140

Gln Val Cys Ser Glu Thr Pro Asp Asp Leu Leu Asp Asp Gly Glu
    1145                1150                1155

Ile Lys Glu Asp Thr Ser Phe Ala Glu Asn Asp Ile Lys Glu Ser
    1160                1165                1170

Ser Ala Val Phe Ser Lys Ser Val Gln Lys Gly Glu Leu Ser Arg
    1175                1180                1185

Ser Pro Ser Pro Phe Thr His Thr His Leu Ala Gln Gly Tyr Arg
    1190                1195                1200

Arg Gly Ala Lys Lys Leu Glu Ser Ser Glu Glu Asn Leu Ser Ser
    1205                1210                1215

Glu Asp Glu Glu Leu Pro Cys Phe Gln His Leu Leu Phe Gly Lys
    1220                1225                1230

Val Asn Asn Ile Pro Ser Gln Ser Thr Arg His Ser Thr Val Ala

```
                1235                1240                1245

Thr Glu
    1250

<210> SEQ ID NO 17
<211> LENGTH: 22
<212> TYPE: PRT
<213> ORGANISM: Homo sapiens

<400> SEQUENCE: 17

Leu Glu Ser Ser Glu Glu Asn Leu Ser Ser Asp Glu Glu Leu Pro
1               5                   10                  15

Cys Phe Gln His Leu Leu
                20

<210> SEQ ID NO 18
<211> LENGTH: 857
<212> TYPE: PRT
<213> ORGANISM: Homo sapiens

<400> SEQUENCE: 18

His Ser Met Ser Pro Glu Arg Glu Met Gly Asn Glu Asn Ile Pro Ser
1               5                   10                  15

Thr Val Ser Thr Ile Ser Arg Asn Asn Ile Arg Glu Asn Val Phe Lys
            20                  25                  30

Glu Ala Ser Ser Ser Asn Ile Asn Glu Val Gly Ser Ser Thr Asn Glu
        35                  40                  45

Val Gly Ser Ser Ile Asn Glu Ile Gly Ser Ser Asp Glu Asn Ile Gln
    50                  55                  60

Ala Glu Leu Gly Arg Asn Arg Gly Pro Lys Leu Asn Ala Met Leu Arg
65                  70                  75                  80

Leu Gly Val Leu Gln Pro Glu Val Tyr Lys Gln Ser Leu Pro Gly Ser
                85                  90                  95

Asn Cys Lys His Pro Glu Ile Lys Lys Gln Glu Tyr Glu Glu Val Val
            100                 105                 110

Gln Thr Val Asn Thr Asp Phe Ser Pro Tyr Leu Ile Ser Asp Asn Leu
        115                 120                 125

Glu Gln Pro Met Gly Ser Ser His Ala Ser Gln Val Cys Ser Glu Thr
    130                 135                 140

Pro Asp Asp Leu Leu Asp Asp Gly Glu Ile Lys Glu Asp Thr Ser Phe
145                 150                 155                 160

Ala Glu Asn Asp Ile Lys Glu Ser Ser Ala Val Phe Ser Lys Ser Val
                165                 170                 175

Gln Lys Gly Glu Leu Ser Arg Ser Pro Ser Pro Phe Thr His Thr His
            180                 185                 190

Leu Ala Gln Gly Tyr Arg Arg Gly Ala Lys Lys Leu Glu Ser Ser Glu
        195                 200                 205

Glu Asn Leu Ser Ser Glu Asp Glu Glu Leu Pro Cys Phe Gln His Leu
    210                 215                 220

Leu Phe Gly Lys Val Asn Asn Ile Pro Ser Gln Ser Thr Arg His Ser
225                 230                 235                 240

Thr Val Ala Thr Glu Cys Leu Ser Lys Asn Thr Glu Glu Asn Leu Leu
                245                 250                 255

Ser Leu Lys Asn Ser Leu Asn Asp Cys Ser Asn Gln Val Ile Leu Ala
            260                 265                 270

Lys Ala Ser Gln Glu His His Leu Ser Glu Glu Thr Lys Cys Ser Ala
        275                 280                 285
```

```
Ser Leu Phe Ser Ser Gln Cys Ser Glu Leu Glu Asp Leu Thr Ala Asn
    290                 295                 300
Thr Asn Thr Gln Asp Pro Phe Leu Ile Gly Ser Ser Lys Gln Met Arg
305                 310                 315                 320
His Gln Ser Glu Ser Gln Gly Val Gly Leu Ser Asp Lys Glu Leu Val
                325                 330                 335
Ser Asp Glu Glu Arg Gly Thr Gly Leu Glu Glu Asn Asn Gln Glu
            340                 345                 350
Glu Gln Ser Met Asp Ser Asn Leu Gly Glu Ala Ala Ser Gly Cys Glu
            355                 360                 365
Ser Glu Thr Ser Val Ser Glu Asp Cys Ser Gly Leu Ser Ser Gln Ser
    370                 375                 380
Asp Ile Leu Thr Thr Gln Gln Arg Asp Thr Met Gln His Asn Leu Ile
385                 390                 395                 400
Lys Leu Gln Gln Glu Met Ala Glu Leu Glu Ala Val Leu Glu Gln His
                405                 410                 415
Gly Ser Gln Pro Ser Asn Ser Tyr Pro Ser Ile Ile Ser Asp Ser Ser
            420                 425                 430
Ala Leu Glu Asp Leu Arg Asn Pro Glu Gln Ser Thr Ser Glu Lys Ala
            435                 440                 445
Val Leu Thr Ser Gln Lys Ser Ser Glu Tyr Pro Ile Ser Gln Asn Pro
450                 455                 460
Glu Gly Leu Ser Ala Asp Lys Phe Glu Val Ser Ala Asp Ser Ser Thr
465                 470                 475                 480
Ser Lys Asn Lys Glu Pro Gly Val Glu Arg Ser Ser Pro Ser Lys Cys
                485                 490                 495
Pro Ser Leu Asp Asp Arg Trp Tyr Met His Ser Cys Ser Gly Ser Leu
            500                 505                 510
Gln Asn Arg Asn Tyr Pro Ser Gln Glu Glu Leu Ile Lys Val Val Asp
            515                 520                 525
Val Glu Glu Gln Gln Leu Glu Glu Ser Gly Pro His Asp Leu Thr Glu
530                 535                 540
Thr Ser Tyr Leu Pro Arg Gln Asp Leu Glu Gly Thr Pro Tyr Leu Glu
545                 550                 555                 560
Ser Gly Ile Ser Leu Phe Ser Asp Asp Pro Glu Ser Asp Pro Ser Glu
                565                 570                 575
Asp Arg Ala Pro Glu Ser Ala Arg Val Gly Asn Ile Pro Ser Ser Thr
            580                 585                 590
Ser Ala Leu Lys Val Pro Gln Leu Lys Val Ala Glu Ser Ala Gln Ser
            595                 600                 605
Pro Ala Ala Ala His Thr Thr Asp Thr Ala Gly Tyr Asn Ala Met Glu
            610                 615                 620
Glu Ser Val Ser Arg Glu Lys Pro Glu Leu Thr Ala Ser Thr Glu Arg
625                 630                 635                 640
Val Asn Lys Arg Met Ser Met Val Val Ser Gly Leu Thr Pro Glu Glu
                645                 650                 655
Phe Met Leu Val Tyr Lys Phe Ala Arg Lys His His Ile Thr Leu Thr
            660                 665                 670
Asn Leu Ile Thr Glu Glu Thr Thr His Val Val Met Lys Thr Asp Ala
            675                 680                 685
Glu Phe Val Cys Glu Arg Thr Leu Lys Tyr Phe Leu Gly Ile Ala Gly
            690                 695                 700
Gly Lys Trp Val Val Ser Tyr Phe Trp Val Thr Gln Ser Ile Lys Glu
```

```
                705                 710                 715                 720
Arg Lys Met Leu Asn Glu His Asp Phe Glu Val Arg Gly Asp Val Val
                    725                 730                 735

Asn Gly Arg Asn His Gln Gly Pro Lys Arg Ala Arg Glu Ser Gln Asp
                740                 745                 750

Arg Lys Ile Phe Arg Gly Leu Glu Ile Cys Cys Tyr Gly Pro Phe Thr
                755                 760                 765

Asn Met Pro Thr Asp Gln Leu Glu Trp Met Val Gln Leu Cys Gly Ala
                770                 775                 780

Ser Val Val Lys Glu Leu Ser Ser Phe Thr Leu Gly Thr Gly Val His
785                 790                 795                 800

Pro Ile Val Val Gln Pro Asp Ala Trp Thr Glu Asp Asn Gly Phe
                    805                 810                 815

His Ala Ile Gly Gln Met Cys Glu Ala Pro Val Val Thr Arg Glu Trp
                820                 825                 830

Val Leu Asp Ser Val Ala Leu Tyr Gln Cys Gln Glu Leu Asp Thr Tyr
                835                 840                 845

Leu Ile Pro Gln Ile Pro His Ser His
    850                 855

<210> SEQ ID NO 19
<211> LENGTH: 547
<212> TYPE: PRT
<213> ORGANISM: Caenorhabditis elegans

<400> SEQUENCE: 19

Met Ala Asp Val Ala Leu Arg Ile Thr Glu Thr Val Ala Arg Leu Gln
1               5                   10                  15

Lys Glu Leu Lys Cys Gly Ile Cys Cys Ser Thr Tyr Lys Asp Pro Ile
                20                  25                  30

Leu Ser Thr Cys Phe His Ile Phe Cys Arg Ser Cys Ile Asn Ala Cys
                35                  40                  45

Phe Glu Arg Lys Arg Lys Val Gln Cys Pro Ile Cys Arg Ser Val Leu
            50                  55                  60

Asp Lys Arg Ser Cys Arg Asp Thr Tyr Gln Ile Thr Met Ala Val Gln
65              70                  75                  80

Asn Tyr Leu Lys Leu Ser Glu Ala Phe Lys Lys Asp Ile Glu Asn Met
                85                  90                  95

Asn Thr Phe Lys Ser Leu Pro Pro Glu Lys Met Phe Met Glu Ser Gln
                100                 105                 110

Met Pro Leu Asp Ile Thr Ile Ile Pro Glu Asn Asp Gly Lys Arg Cys
            115                 120                 125

Ala Pro Asp Phe Ala Ile Pro Phe Leu Pro Val Arg Arg Lys Arg Pro
        130                 135                 140

Ser Arg Pro Gln Pro Pro Ser Ala Phe Ala Glu Glu Pro Ala Glu Pro
145                 150                 155                 160

Val Glu Pro Pro Glu Pro Ala Thr Lys Gln Pro Val Glu Leu Gln Ser
                165                 170                 175

Arg Val Phe Pro Leu Glu Lys Leu Lys Lys Asp Val Glu Thr Ser Thr
                180                 185                 190

Glu Thr Tyr Lys Ile Ser Arg Glu Glu Leu Lys Asn Val Asp Ile Glu
            195                 200                 205

Glu Tyr Ile Asn Thr Leu Arg Glu Asn Ser Thr Glu Ile Asp Glu Ile
        210                 215                 220

Asp Ala Leu Phe Gln Leu Met Pro Thr Met Arg Gln Phe Leu Arg Asn
```

```
                225                 230                 235                 240
Asn Ile Asn Gln Leu Met Glu Lys Phe His Val Ala Pro Lys Lys
                245                 250                 255
Ser Glu Lys Pro Ala Asn Arg Arg Val Ser Phe Ala Ser Ser Gln Asp
            260                 265                 270
Leu Glu Asn Ile Lys Ile Met Thr Ala Ser Glu Ser Leu Glu Thr Pro
        275                 280                 285
Pro Glu Pro Ile Gln Lys Leu Ala Gln Lys Pro Glu Val Phe Lys Ser
    290                 295                 300
Thr Gln Asn Leu Ile Asp Leu Asn Leu Asn Thr Ala Val Lys Lys Pro
305                 310                 315                 320
Val Val Val Ala Ser Asp Asp Glu Val Val Glu Asp Ser Glu Gly
                325                 330                 335
Glu Leu Gln Ile Asp Glu Asp Leu Ala Asn Val Thr Cys Ala Thr
                340                 345                 350
Ser Val Arg Asn Ile Gly Lys Ser Leu Cys Ala Glu Tyr Ile Arg Glu
            355                 360                 365
Gly Arg Ser Ile Ser Gln Lys Ser Thr Ala Tyr Leu Tyr Ala Ile Ala
        370                 375                 380
Arg Lys Cys Val Ile Val Gly Arg Gln Trp Leu Val Asp Cys Ile Thr
385                 390                 395                 400
Thr Gly Leu Leu Leu Ser Glu Ala Asp Tyr Thr Ile Thr Ser Cys Ser
                405                 410                 415
Ser Thr Ile Pro Val Lys Ile Pro Pro Ser Ile Gly Ser Glu Met Gly
            420                 425                 430
Trp Leu Arg Ser Arg Asn Asp Glu His Gly Lys Leu Phe Ala Gly Arg
        435                 440                 445
Arg Phe Met Ile Leu Arg Lys Phe Thr Met Asn Pro Tyr Phe Asp Tyr
    450                 455                 460
Lys Gln Leu Ile Glu Leu Val Gln Gln Cys Gly Gly Glu Ile Leu Ser
465                 470                 475                 480
Cys Tyr Glu Asn Leu Ser Pro Glu Lys Leu Tyr Ile Ile Phe Ser Lys
                485                 490                 495
His Ser Lys Ala Ile Glu Glu Ser Lys Asn Ile Glu Asn Leu Tyr Lys
            500                 505                 510
Cys Asp Val Val Thr Met Glu Trp Val Leu Asp Ser Ile Ser Glu Tyr
        515                 520                 525
Leu Ile Leu Pro Thr Gln Pro Tyr Lys Ala Val Asp Ser Ile Gly Cys
    530                 535                 540
Leu Gln Asp
545

<210> SEQ ID NO 20
<211> LENGTH: 1817
<212> TYPE: PRT
<213> ORGANISM: Rattus norvegicus
<220> FEATURE:
<221> NAME/KEY: MOD_RES
<222> LOCATION: (1491)..(1491)
<223> OTHER INFORMATION: Any amino acid

<400> SEQUENCE: 20

Met Asp Leu Ser Ala Val Arg Ile Gln Glu Val Gln Asn Val Leu His
1               5                   10                  15
Ala Met Gln Lys Ile Leu Glu Cys Pro Ile Cys Leu Glu Leu Ile Lys
            20                  25                  30
```

```
Glu Pro Val Ser Thr Gln Cys Asp His Ile Phe Cys Lys Phe Cys Met
    35                  40                  45

Leu Lys Leu Leu Asn Gln Lys Lys Gly Pro Ser Gln Cys Pro Leu Cys
50                  55                  60

Lys Asn Glu Ile Thr Lys Arg Ser Leu Gln Gly Ser Ala Arg Phe Ser
65                  70                  75                  80

Gln Leu Val Glu Glu Leu Leu Lys Ile Ile Asp Ala Phe Glu Leu Asp
                85                  90                  95

Thr Gly Met Gln Cys Ala Asn Gly Phe Ser Phe Ser Lys Lys Lys Asn
            100                 105                 110

Ser Ser Ser Glu Leu Leu Asn Glu Asp Ala Ser Ile Ile Gln Ser Val
        115                 120                 125

Gly Tyr Arg Asn Arg Val Lys Lys Leu Gln Gln Ile Glu Ser Gly Ser
    130                 135                 140

Ala Thr Leu Lys Asp Ser Leu Ser Val Gln Leu Ser Asn Leu Gly Ile
145                 150                 155                 160

Val Arg Ser Met Lys Lys Asn Arg Gln Thr Gln Pro Gln Asn Lys Ser
                165                 170                 175

Val Tyr Ile Ala Leu Glu Ser Asp Ser Glu Glu Arg Val Asn Ala
            180                 185                 190

Pro Asp Gly Cys Ser Val Arg Asp Gln Glu Leu Phe Gln Ile Ala Pro
        195                 200                 205

Gly Gly Ala Gly Asp Glu Gly Lys Leu Asn Ser Ala Lys Lys Ala Ala
    210                 215                 220

Cys Asp Phe Ser Glu Gly Ile Arg Asn Ile Glu His His Gln Cys Ser
225                 230                 235                 240

Asp Lys Asp Leu Asn Pro Thr Glu Asn His Ala Thr Glu Arg His Pro
                245                 250                 255

Glu Lys Cys Pro Arg Ile Ser Val Ala Asn Val His Val Glu Pro Cys
            260                 265                 270

Gly Thr Asp Ala Arg Ala Ser Ser Leu Gln Arg Gly Thr Arg Ser Leu
        275                 280                 285

Leu Phe Thr Glu Asp Arg Leu Asp Ala Glu Lys Ala Glu Phe Cys Asp
    290                 295                 300

Arg Ser Lys Gln Ser Gly Ala Ala Val Ser Gln Gln Ser Arg Trp Ala
305                 310                 315                 320

Asp Ser Lys Glu Thr Cys Asn Gly Arg Pro Val Pro Arg Thr Glu Gly
                325                 330                 335

Lys Ala Asp Pro Asn Val Asp Ser Leu Cys Gly Arg Lys Gln Trp Asn
            340                 345                 350

His Pro Lys Ser Leu Cys Pro Glu Asn Ser Gly Ala Thr Thr Asp Val
        355                 360                 365

Pro Trp Ile Thr Leu Asn Ser Ser Ile Gln Lys Val Asn Glu Trp Phe
    370                 375                 380

Ser Arg Thr Gly Glu Met Leu Thr Ser Asp Asn Ala Ser Asp Arg Arg
385                 390                 395                 400

Pro Ala Ser Asn Ala Glu Ala Val Val Leu Glu Val Ser Asn Glu
                405                 410                 415

Val Asp Gly Cys Phe Ser Ser Lys Lys Ile Asp Leu Val Ala Pro
            420                 425                 430

Asp Pro Asp Asn Ala Val Met Cys Thr Ser Gly Arg Asp Phe Ser Lys
        435                 440                 445

Pro Val Glu Asn Ile Ile Asn Asp Lys Ile Phe Gly Lys Thr Tyr Gln
    450                 455                 460
```

```
Arg Lys Gly Ser Arg Pro His Leu Asn His Val Thr Glu Ile Ile Gly
465                 470                 475                 480

Thr Phe Thr Thr Glu Pro Gln Ile Ile Gln Glu Gln Pro Phe Thr Asn
                485                 490                 495

Lys Leu Lys Arg Lys Arg Ser Thr Cys Leu His Pro Glu Asp Phe Ile
            500                 505                 510

Lys Lys Ala Asp Leu Thr Val Val Gln Arg Ile Ser Glu Asn Leu Asn
            515                 520                 525

Gln Gly Thr Asp Gln Met Glu Pro Asn Asp Gln Ala Met Ser Ile Thr
        530                 535                 540

Ser Asn Gly Gln Glu Asn Arg Ala Thr Gly Asn Asp Leu Gln Arg Gly
545                 550                 555                 560

Arg Asn Ala His Pro Ile Glu Ser Leu Arg Lys Glu Pro Ala Phe Thr
                565                 570                 575

Ala Lys Ala Lys Ser Ile Ser Asn Ser Ile Ser Asp Leu Glu Val Glu
            580                 585                 590

Leu Asn Val His Ser Ser Lys Ala Pro Lys Lys Asn Arg Leu Arg Arg
            595                 600                 605

Lys Ser Thr Arg Cys Val Leu Pro Leu Glu Pro Ile Ser Arg Asn Pro
        610                 615                 620

Ser Pro Pro Thr Cys Ala Glu Leu Gln Ile Glu Ser Cys Gly Ser Ser
625                 630                 635                 640

Glu Glu Thr Lys Lys Asn Asn Ser Asn Gln Thr Pro Ala Gly His Ile
                645                 650                 655

Arg Glu Pro Gln Leu Ile Glu Asp Thr Glu Pro Ala Ala Asp Ala Lys
            660                 665                 670

Lys Asn Glu Pro Asn Glu His Ile Arg Lys Arg Ser Ala Ser Asp Ala
            675                 680                 685

Phe Pro Glu Glu Lys Leu Met Asn Lys Ala Gly Leu Leu Thr Ser Cys
690                 695                 700

Ser Ser Pro Arg Lys Pro Gln Gly Pro Val Asn Pro Ser Pro Glu Arg
705                 710                 715                 720

Lys Gly Ile Glu Gln Leu Glu Met Cys Gln Met Pro Asp Asn Asn Lys
                725                 730                 735

Glu Leu Gly Asp Leu Val Leu Gly Gly Glu Pro Ser Gly Lys Pro Thr
            740                 745                 750

Glu Pro Ser Glu Glu Ser Thr Ser Val Ser Leu Val Pro Asp Thr Asp
            755                 760                 765

Tyr Asp Thr Gln Asn Ser Val Ser Ile Leu Glu Ala Asn Thr Val Arg
770                 775                 780

Tyr Ala Arg Thr Gly Ser Val Gln Cys Met Thr Gln Phe Val Ala Ser
785                 790                 795                 800

Glu Asn Pro Lys Glu Leu Val His Gly Ser Asn Asn Ala Gly Ser Gly
                805                 810                 815

Ser Glu Cys Phe Lys His Pro Leu Arg His Glu Leu Asn His Asn Gln
            820                 825                 830

Glu Thr Ile Glu Met Glu Asp Ser Glu Leu Asp Thr Gln Tyr Leu Gln
            835                 840                 845

Asn Thr Phe Gln Val Ser Lys Arg Gln Ser Phe Ala Leu Phe Ser Lys
850                 855                 860

Leu Arg Ser Pro Gln Lys Asp Cys Thr Leu Val Gly Ala Arg Ser Val
865                 870                 875                 880

Pro Ser Arg Glu Pro Ser Pro Lys Val Thr Ser Arg Gly Glu Gln Lys
```

-continued

```
                885                 890                 895
Glu Arg Gln Gly Gln Glu Glu Ser Glu Ile Ser His Val Gln Ala Val
            900                 905                 910
Thr Val Thr Val Gly Leu Pro Val Pro Cys Gln Glu Gly Lys Pro Gly
            915                 920                 925
Ala Val Thr Met Cys Ala Asp Val Ser Arg Leu Cys Pro Ser Ser His
            930                 935                 940
Tyr Arg Ser Cys Glu Asn Gly Leu Asn Thr Thr Asp Lys Ser Gly Ile
945                 950                 955                 960
Ser Gln Asn Ser His Phe Arg Gln Ser Val Ser Pro Leu Arg Ser Ser
                965                 970                 975
Ile Lys Thr Asp Asn Arg Lys Thr Leu Thr Glu Gly Arg Phe Glu Lys
            980                 985                 990
His Thr Glu Arg Gly Met Gly Asn Glu Thr Ala Val Gln Ser Thr Ile
            995                 1000                1005
His Thr Ile Ser Leu Asn Asn Arg Gly Asp Ala Cys Leu Glu Ala
            1010                1015                1020
Ser Ser Gly Ser Val Ile Glu Val His Ser Thr Gly Glu Asn Val
            1025                1030                1035
Gln Gly Gln Leu Asp Arg Asn Arg Gly Pro Lys Val Asn Thr Val
            1040                1045                1050
Ser Leu Leu Asp Ser Thr Gln Pro Gly Val Ser Lys Gln Ser Ala
            1055                1060                1065
Pro Val Ser Asp Lys Tyr Leu Glu Ile Lys Gln Glu Ser Lys Ala
            1070                1075                1080
Val Ser Ala Asp Phe Ser Pro Cys Leu Phe Ser Asp His Leu Glu
            1085                1090                1095
Lys Pro Met Arg Ser Asp Lys Thr Phe Gln Val Cys Ser Glu Thr
            1100                1105                1110
Pro Asp Asp Leu Leu Asp Asp Val Glu Ile Gln Glu Asn Ala Ser
            1115                1120                1125
Phe Gly Glu Gly Gly Ile Thr Glu Lys Ser Ala Ile Phe Asn Gly
            1130                1135                1140
Ser Val Leu Arg Arg Glu Ser Arg Ser Pro Ser Pro Val Thr
            1145                1150                1155
His Ala Ser Lys Ser Arg Ser Leu His Arg Gly Ser Arg Lys Leu
            1160                1165                1170
Glu Phe Ser Glu Glu Ser Asp Ser Thr Glu Asp Glu Asp Leu Pro
            1175                1180                1185
Cys Phe Gln His Leu Leu Ser Arg Val Ser Ser Thr Pro Glu Leu
            1190                1195                1200
Thr Arg Cys Ser Ser Val Val Thr Gln Arg Val Pro Glu Lys Ala
            1205                1210                1215
Lys Gly Thr Gln Ala Pro Arg Lys Ser Ser Ile Ser Asp Cys Asn
            1220                1225                1230
Asn Glu Val Ile Leu Gly Glu Ala Ser Gln Glu Tyr Gln Phe Ser
            1235                1240                1245
Glu Asp Ala Lys Cys Ser Gly Ser Met Phe Ser Ser Gln His Ser
            1250                1255                1260
Ala Ala Leu Gly Ser Pro Ala Asn Ala Leu Ser Gln Asp Pro Asp
            1265                1270                1275
Phe Asn Pro Pro Ser Lys Gln Arg Arg His Gln Ala Glu Asn Glu
            1280                1285                1290
```

```
Glu Ala Phe Leu Ser Asp Lys Glu Leu Ile Ser Asp His Glu Asp
    1295                1300                1305

Met Ala Ala Cys Leu Glu Glu Ala Ser Asp Gln Glu Asp Ser
    1310                1315                1320

Ile Ile Pro Asp Ser Val Ala Ser Gly Tyr Glu Ser Glu Ala Asn
    1325                1330                1335

Leu Ser Glu Asp Cys Ser Gln Ser Asp Ile Leu Thr Thr Gln Gln
    1340                1345                1350

Arg Ala Thr Met Lys Asp Asn Leu Ile Lys Leu Gln Gln Glu Met
    1355                1360                1365

Ala Gln Leu Glu Ala Val Leu Glu Gln His Gly Ser Gln Pro Ser
    1370                1375                1380

Gly His Pro Pro Cys Leu Pro Ala Asp Pro Cys Ala Leu Glu Asp
    1385                1390                1395

Leu Pro Asp Pro Glu Gln Asn Arg Ser Gly Thr Ala Ile Leu Thr
    1400                1405                1410

Ser Lys Asn Ile Asn Glu Asn Pro Val Ser Gln Asn Pro Lys Arg
    1415                1420                1425

Ala Cys Asp Asp Lys Ser Gln Pro Gln Pro Asp Gly Leu Pro
    1430                1435                1440

Ser Gly Asp Lys Glu Ser Gly Met Arg Arg Pro Ser Pro Phe Lys
    1445                1450                1455

Ser Pro Leu Thr Ser Ser Arg Cys Ser Ala Arg Gly His Ser Arg
    1460                1465                1470

Ser Leu Gln Asn Arg Asn Ser Thr Ser Gln Glu Glu Leu Leu Gln
    1475                1480                1485

Pro Ala Xaa Leu Glu Lys Ser Cys Glu Pro His Asn Leu Thr Gly
    1490                1495                1500

Arg Ser Cys Leu Pro Arg Gln Asp Leu Glu Gly Thr Pro Tyr Pro
    1505                1510                1515

Glu Ser Gly Ile Arg Leu Val Ser Ser Arg Asp Pro Asp Ser Glu
    1520                1525                1530

Ser Pro Lys Val Ser Ala Leu Val Cys Thr Ala Pro Ala Ser Thr
    1535                1540                1545

Ser Ala Leu Lys Ile Ser Gln Gly Gln Val Ala Gly Ser Cys Arg
    1550                1555                1560

Ser Pro Ala Ala Gly Gly Ala Asp Thr Ala Val Val Glu Ile Val
    1565                1570                1575

Ser Lys Ile Lys Pro Glu Val Thr Ser Pro Lys Glu Arg Ala Glu
    1580                1585                1590

Arg Asp Ile Ser Met Val Val Ser Gly Leu Thr Pro Lys Glu Val
    1595                1600                1605

Met Ile Val Gln Lys Phe Ala Glu Lys Tyr Arg Leu Ala Leu Thr
    1610                1615                1620

Asp Val Ile Thr Glu Glu Thr Thr His Val Ile Ile Lys Thr Asp
    1625                1630                1635

Ala Glu Phe Val Cys Glu Arg Thr Leu Lys Tyr Phe Leu Gly Ile
    1640                1645                1650

Ala Gly Gly Lys Trp Ile Val Ser Tyr Ser Trp Val Ile Lys Ser
    1655                1660                1665

Ile Gln Glu Arg Lys Leu Leu Ser Val His Glu Phe Glu Val Lys
    1670                1675                1680

Gly Asp Val Val Thr Gly Ser Asn His Gln Gly Pro Arg Arg Ser
    1685                1690                1695
```

```
Arg Glu Ser Gln Glu Lys Leu Phe Glu Gly Leu Gln Ile Tyr Cys
    1700                1705                1710

Cys Glu Pro Phe Thr Asn Met Pro Lys Asp Glu Leu Glu Arg Met
    1715                1720                1725

Leu Gln Leu Cys Gly Ala Ser Val Val Lys Glu Leu Pro Leu Leu
    1730                1735                1740

Thr Arg Asp Thr Gly Ala His Pro Ile Val Leu Val Gln Pro Ser
    1745                1750                1755

Ala Trp Thr Glu Asp Asn Asp Cys Pro Asp Ile Gly Gln Leu Cys
    1760                1765                1770

Lys Gly Arg Leu Val Met Trp Asp Trp Val Leu Asp Ser Ile Ser
    1775                1780                1785

Val Tyr Arg Cys Arg Asp Leu Asp Ala Tyr Leu Val Gln Asn Ile
    1790                1795                1800

Thr Cys Gly Arg Asp Gly Ser Glu Pro Gln Asp Ser Asn Asp
    1805                1810                1815
```

<210> SEQ ID NO 21
<211> LENGTH: 1812
<212> TYPE: PRT
<213> ORGANISM: Mus musculus

<400> SEQUENCE: 21

```
Met Asp Leu Ser Ala Val Gln Ile Gln Glu Val Gln Asn Val Leu His
1               5                   10                  15

Ala Met Gln Lys Ile Leu Glu Cys Pro Ile Cys Leu Glu Leu Ile Lys
                20                  25                  30

Glu Pro Val Ser Thr Lys Cys Asp His Ile Phe Cys Lys Phe Cys Met
            35                  40                  45

Leu Lys Leu Leu Asn Gln Lys Lys Gly Pro Ser Gln Cys Pro Leu Cys
        50                  55                  60

Lys Asn Glu Ile Thr Lys Arg Ser Leu Gln Gly Ser Thr Arg Phe Ser
65                  70                  75                  80

Gln Leu Ala Glu Glu Leu Leu Arg Ile Met Ala Ala Phe Glu Leu Asp
                85                  90                  95

Thr Gly Met Gln Leu Thr Asn Gly Phe Ser Phe Ser Lys Lys Arg Asn
            100                 105                 110

Asn Ser Cys Glu Arg Leu Asn Glu Glu Ala Ser Ile Ile Gln Ser Val
        115                 120                 125

Gly Tyr Arg Asn Arg Val Arg Arg Leu Pro Gln Val Glu Pro Gly Asn
    130                 135                 140

Ala Thr Leu Lys Asp Ser Leu Gly Val Gln Leu Ser Asn Leu Gly Ile
145                 150                 155                 160

Val Arg Ser Val Lys Lys Asn Arg Gln Thr Gln Pro Arg Lys Lys Ser
                165                 170                 175

Val Tyr Ile Glu Leu Asp Ser Asp Ser Ser Glu Glu Thr Val Thr Lys
            180                 185                 190

Pro Gly Asp Cys Ser Val Arg Asp Gln Glu Leu Leu Gln Thr Ala Pro
        195                 200                 205

Gln Glu Ala Gly Asp Glu Gly Lys Leu His Ser Ala Glu Glu Ala Ala
    210                 215                 220

Cys Glu Phe Ser Glu Gly Ile Arg Asn Ile Glu His Gln Cys Ser
225                 230                 235                 240

Asp Asp Leu Asn Pro Thr Glu Asn His Ala Thr Glu Arg His Pro Glu
                245                 250                 255
```

```
Lys Cys Gln Ser Ile Ser Ile Ser Asn Val Cys Val Glu Pro Cys Gly
            260                 265                 270

Thr Asp Ala His Ala Ser Ser Leu Gln Pro Glu Thr Ser Ser Leu Leu
            275                 280                 285

Leu Ile Glu Asp Arg Met Asn Ala Glu Lys Ala Glu Phe Cys Asn Lys
            290                 295                 300

Ser Lys Gln Pro Gly Ile Ala Val Ser Gln Gln Ser Arg Trp Ala Ala
305                 310                 315                 320

Ser Lys Gly Thr Cys Asn Asp Arg Gln Val Pro Ser Thr Gly Glu Lys
            325                 330                 335

Val Gly Pro Asn Ala Asp Ser Leu Ser Asp Arg Glu Lys Trp Thr His
            340                 345                 350

Pro Gln Ser Leu Cys Pro Glu Asn Ser Gly Ala Thr Thr Asp Val Pro
            355                 360                 365

Trp Ile Thr Leu Asn Ser Ser Val Gln Lys Val Asn Glu Trp Phe Ser
            370                 375                 380

Arg Thr Gly Glu Met Leu Thr Ser Asp Ser Ala Ser Ala Arg Arg His
385                 390                 395                 400

Glu Ser Asn Ala Glu Ala Ala Val Val Leu Glu Val Ser Asn Glu Val
            405                 410                 415

Asp Gly Gly Phe Ser Ser Ser Arg Lys Thr Asp Leu Val Thr Pro Asp
            420                 425                 430

Pro His His Thr Leu Met Cys Lys Ser Gly Arg Asp Phe Ser Lys Pro
            435                 440                 445

Val Glu Asp Asn Ile Ser Asp Lys Ile Phe Gly Lys Ser Tyr Gln Arg
            450                 455                 460

Lys Gly Ser Arg Pro His Leu Asn His Val Thr Glu Ile Ile Gly Thr
465                 470                 475                 480

Phe Ile Thr Glu Pro Gln Ile Thr Gln Glu Gln Pro Phe Thr Asn Lys
            485                 490                 495

Leu Lys Arg Lys Arg Ser Thr Ser Leu Gln Pro Glu Asp Phe Ile Lys
            500                 505                 510

Lys Ala Asp Ser Ala Gly Val Gln Arg Thr Pro Asp Asn Ile Asn Gln
            515                 520                 525

Gly Thr Asp Leu Met Glu Pro Asn Glu Gln Ala Val Ser Thr Thr Ser
            530                 535                 540

Asn Cys Gln Glu Asn Lys Ile Ala Gly Ser Asn Leu Gln Lys Glu Lys
545                 550                 555                 560

Ser Ala His Pro Thr Glu Ser Leu Arg Lys Glu Pro Ala Ser Thr Ala
            565                 570                 575

Gly Ala Lys Ser Ile Ser Asn Ser Val Ser Asp Leu Glu Val Glu Leu
            580                 585                 590

Asn Val His Ser Ser Lys Ala Pro Lys Lys Asn Arg Leu Arg Arg Lys
            595                 600                 605

Ser Ser Ile Arg Cys Ala Leu Pro Leu Glu Pro Ile Ser Arg Asn Pro
            610                 615                 620

Ser Pro Pro Thr Cys Ala Glu Leu Gln Ile Asp Ser Cys Gly Ser Ser
625                 630                 635                 640

Glu Glu Thr Lys Lys Asn His Ser Asn Gln Gln Pro Ala Gly His Leu
            645                 650                 655

Arg Glu Pro Gln Leu Ile Glu Asp Thr Glu Pro Ala Ala Asp Ala Lys
            660                 665                 670

Lys Asn Glu Pro Asn Glu His Ile Arg Lys Arg Arg Ala Ser Asp Ala
```

```
            675                 680                 685
Phe Pro Glu Glu Lys Leu Met Asn Lys Ala Gly Leu Leu Thr Ser Cys
690                 695                 700

Ser Ser Pro Arg Lys Ser Gln Gly Pro Val Asn Pro Ser Pro Gln Arg
705                 710                 715                 720

Thr Gly Thr Glu Gln Leu Glu Thr Arg Gln Met Ser Asp Ser Ala Lys
                725                 730                 735

Glu Leu Gly Asp Arg Val Leu Gly Glu Pro Ser Gly Lys Thr Thr
                740                 745                 750

Asp Arg Ser Glu Glu Ser Thr Ser Val Ser Leu Val Ser Asp Thr Asp
                755                 760                 765

Tyr Asp Thr Gln Asn Ser Val Ser Val Leu Asp Ala His Thr Val Arg
                770                 775                 780

Tyr Ala Arg Thr Gly Ser Ala Gln Cys Met Thr Gln Phe Val Ala Ser
785                 790                 795                 800

Glu Asn Pro Lys Glu Leu Val His Gly Ser Asn Asn Ala Gly Ser Gly
                805                 810                 815

Thr Glu Gly Leu Lys Pro Pro Leu Arg His Ala Leu Asn Leu Ser Gln
                820                 825                 830

Glu Lys Val Glu Met Glu Asp Ser Glu Leu Asp Thr Gln Tyr Leu Gln
                835                 840                 845

Asn Thr Phe Gln Val Ser Lys Arg Gln Ser Phe Ala Leu Phe Ser Lys
                850                 855                 860

Pro Arg Ser Pro Gln Lys Asp Cys Ala His Ser Val Pro Ser Lys Glu
865                 870                 875                 880

Leu Ser Pro Lys Val Thr Ala Lys Gly Lys Gln Lys Glu Arg Gln Gly
                885                 890                 895

Gln Glu Glu Phe Glu Ile Ser His Val Gln Ala Val Ala Ala Thr Val
                900                 905                 910

Gly Leu Pro Val Pro Cys Gln Glu Gly Lys Leu Ala Ala Asp Thr Met
                915                 920                 925

Cys Asp Arg Gly Cys Arg Leu Cys Pro Ser Ser His Tyr Arg Ser Gly
930                 935                 940

Glu Asn Gly Leu Ser Ala Thr Gly Lys Ser Gly Ile Ser Gln Asn Ser
945                 950                 955                 960

His Phe Lys Gln Ser Val Ser Pro Ile Arg Ser Ser Ile Lys Thr Asp
                965                 970                 975

Asn Arg Lys Pro Leu Thr Glu Gly Arg Phe Glu Arg His Thr Ser Ser
                980                 985                 990

Thr Glu Met Ala Val Gly Asn Glu Asn Ile Leu Gln Ser Thr Val His
                995                 1000                1005

Thr Val Ser Leu Asn Asn Arg Gly Asn Ala Cys Gln Glu Ala Gly
                1010                1015                1020

Ser Gly Ser Ile His Glu Val Cys Ser Thr Gly Asp Ser Phe Pro
                1025                1030                1035

Gly Gln Leu Gly Arg Asn Arg Gly Pro Lys Val Asn Thr Val Pro
                1040                1045                1050

Pro Leu Asp Ser Met Gln Pro Gly Val Cys Gln Gln Ser Val Pro
                1055                1060                1065

Val Ser Asp Lys Tyr Leu Glu Ile Lys Lys Gln Glu Gly Glu Ala
                1070                1075                1080

Val Cys Ala Asp Phe Ser Pro Cys Leu Phe Ser Asp His Leu Glu
                1085                1090                1095
```

```
Gln Ser Met Ser Gly Lys Val Phe Gln Val Cys Ser Glu Thr Pro
    1100            1105            1110

Asp Asp Leu Leu Asp Asp Val Glu Ile Gln Gly His Thr Ser Phe
    1115            1120            1125

Gly Glu Gly Asp Ile Met Glu Arg Ser Ala Val Phe Asn Gly Ser
    1130            1135            1140

Ile Leu Arg Arg Glu Ser Arg Ser Pro Ser Pro Val Thr His
    1145            1150            1155

Ala Ser Lys Ser Gln Ser Leu His Arg Ala Ser Arg Lys Leu Glu
    1160            1165            1170

Ser Ser Glu Glu Ser Asp Ser Thr Glu Asp Glu Asp Leu Pro Cys
    1175            1180            1185

Phe Gln His Leu Leu Ser Arg Ile Ser Asn Thr Pro Glu Leu Thr
    1190            1195            1200

Arg Cys Ser Ser Ala Val Thr Gln Arg Met Pro Glu Lys Ala Glu
    1205            1210            1215

Gly Thr Gln Ala Pro Trp Lys Gly Ser Ser Asp Cys Asn Asn
    1220            1225            1230

Glu Val Ile Met Ile Glu Ala Ser Gln Glu His Gln Phe Ser Glu
    1235            1240            1245

Asp Pro Arg Cys Ser Gly Ser Met Phe Ser Ser Gln His Ser Ala
    1250            1255            1260

Ala Gln Gly Ser Thr Ala Asn Ala Asn Ser Gln Asp Ser Asn Phe
    1265            1270            1275

Ile Pro Pro Ser Lys Gln Arg Ser His Gln Cys Gly Asn Glu Glu
    1280            1285            1290

Ala Phe Leu Ser Asp Lys Glu Leu Ile Ser Asp Asn Glu Glu Met
    1295            1300            1305

Ala Thr Cys Leu Glu Glu Asp Asn Asp Gln Glu Glu Asp Ser Ile
    1310            1315            1320

Ile Pro Asp Ser Glu Ala Ser Gly Tyr Glu Ser Glu Thr Asn Leu
    1325            1330            1335

Ser Glu Asp Cys Ser Gln Ser Asp Ile Leu Thr Thr Gln Gln Arg
    1340            1345            1350

Ala Thr Met Lys Tyr Asn Leu Ile Lys Leu Gln Gln Glu Met Ala
    1355            1360            1365

His Leu Glu Ala Val Leu Glu Gln Arg Gly Asn Gln Pro Ser Gly
    1370            1375            1380

His Ser Pro Ser Leu Leu Ala Asp Pro Cys Ala Leu Glu Asp Leu
    1385            1390            1395

Pro Asp Leu Glu Pro Asn Met Ser Gly Ala Ala Ile Leu Thr Ser
    1400            1405            1410

Lys Asn Ile Asn Glu Asn Pro Val Ser Gln Asn Leu Lys Ser Ala
    1415            1420            1425

Cys Asp Asp Lys Phe Gln Leu Gln His Leu Glu Gly Pro Thr Ser
    1430            1435            1440

Gly Asp Asp Glu Ser Gly Met Gly Arg Pro Ser Pro Phe Lys Ser
    1445            1450            1455

Pro Leu Ala Gly Ser Arg Gly Ser Ala His Gly Cys Ser Arg His
    1460            1465            1470

Leu Gln Lys Arg Asn Ser Pro Ser Gln Glu Glu Leu Leu Gln Pro
    1475            1480            1485

Ala Gly Ser Glu Ala Ser Ser Glu Pro His Asn Ser Thr Gly Gln
    1490            1495            1500
```

```
Ser Cys Leu Pro Arg Arg Glu Leu Glu Gly Thr Pro Tyr Leu Gly
    1505                1510                1515

Ser Gly Ile Ser Leu Phe Ser Ser Arg Asp Pro Glu Ser Glu Ser
    1520                1525                1530

Pro Lys Glu Pro Ala His Ile Gly Thr Thr Pro Ala Ser Thr Ser
    1535                1540                1545

Ala Leu Lys Ile Pro Gln Gly Gln Val Ala Phe Arg Ser Ala Ala
    1550                1555                1560

Ala Ala Gly Ala Asp Lys Ala Val Val Gly Ile Val Ser Lys Ile
    1565                1570                1575

Lys Pro Glu Leu Thr Ser Ser Glu Glu Arg Ala Asp Arg Asp Ile
    1580                1585                1590

Ser Met Val Val Ser Gly Leu Thr Pro Lys Glu Val Met Thr Val
    1595                1600                1605

Gln Lys Phe Ala Glu Lys Tyr Arg Leu Thr Leu Thr Asp Ala Ile
    1610                1615                1620

Thr Glu Glu Thr Thr His Val Ile Ile Lys Thr Asp Ala Glu Phe
    1625                1630                1635

Val Cys Glu Arg Thr Leu Lys Tyr Phe Leu Gly Ile Ala Gly Gly
    1640                1645                1650

Lys Trp Ile Val Ser Tyr Ser Trp Val Val Arg Ser Ile Gln Glu
    1655                1660                1665

Arg Arg Leu Leu Asn Val His Glu Phe Glu Val Lys Gly Asp Val
    1670                1675                1680

Val Thr Gly Arg Asn His Gln Gly Pro Arg Arg Ser Arg Glu Ser
    1685                1690                1695

Arg Glu Lys Leu Phe Lys Gly Leu Gln Val Tyr Cys Cys Glu Pro
    1700                1705                1710

Phe Thr Asn Met Pro Lys Asp Glu Leu Glu Arg Met Leu Gln Leu
    1715                1720                1725

Cys Gly Ala Ser Val Val Lys Glu Leu Pro Ser Leu Thr His Asp
    1730                1735                1740

Thr Gly Ala His Leu Val Val Ile Val Gln Pro Ser Ala Trp Thr
    1745                1750                1755

Glu Asp Ser Asn Cys Pro Asp Ile Gly Gln Leu Cys Lys Ala Arg
    1760                1765                1770

Leu Val Met Trp Asp Trp Val Leu Asp Ser Leu Ser Ser Tyr Arg
    1775                1780                1785

Cys Arg Asp Leu Asp Ala Tyr Leu Val Gln Asn Ile Thr Cys Asp
    1790                1795                1800

Ser Ser Glu Pro Gln Asp Ser Asn Asp
    1805                1810

<210> SEQ ID NO 22
<211> LENGTH: 1266
<212> TYPE: PRT
<213> ORGANISM: Tetraodon nigroviridis
<220> FEATURE:
<221> NAME/KEY: MOD_RES
<222> LOCATION: (139)..(139)
<223> OTHER INFORMATION: Any amino acid
<220> FEATURE:
<221> NAME/KEY: MOD_RES
<222> LOCATION: (196)..(196)
<223> OTHER INFORMATION: Any amino acid
<220> FEATURE:
<221> NAME/KEY: MOD_RES
<222> LOCATION: (412)..(412)
```

-continued

```
<223> OTHER INFORMATION: Any amino acid
<220> FEATURE:
<221> NAME/KEY: MOD_RES
<222> LOCATION: (506)..(506)
<223> OTHER INFORMATION: Any amino acid
<220> FEATURE:
<221> NAME/KEY: MOD_RES
<222> LOCATION: (574)..(574)
<223> OTHER INFORMATION: Any amino acid
<220> FEATURE:
<221> NAME/KEY: MOD_RES
<222> LOCATION: (688)..(688)
<223> OTHER INFORMATION: Any amino acid
<220> FEATURE:
<221> NAME/KEY: MOD_RES
<222> LOCATION: (837)..(837)
<223> OTHER INFORMATION: Any amino acid
<220> FEATURE:
<221> NAME/KEY: MOD_RES
<222> LOCATION: (931)..(931)
<223> OTHER INFORMATION: Any amino acid
<220> FEATURE:
<221> NAME/KEY: MOD_RES
<222> LOCATION: (955)..(955)
<223> OTHER INFORMATION: Any amino acid
<220> FEATURE:
<221> NAME/KEY: MOD_RES
<222> LOCATION: (1036)..(1036)
<223> OTHER INFORMATION: Any amino acid
<220> FEATURE:
<221> NAME/KEY: MOD_RES
<222> LOCATION: (1198)..(1198)
<223> OTHER INFORMATION: Any amino acid

<400> SEQUENCE: 22

Met Glu Ala Pro Thr Ala Thr Asp Val Lys Lys Arg Ile Ser Leu Leu
1               5                   10                  15

Trp Glu Thr Leu Gln Cys Pro Ile Cys Leu Asp Leu Met Ser Pro Val
            20                  25                  30

Ser Thr Lys Cys Asp His Gln Phe Cys Arg Phe Cys Met Leu Lys Leu
        35                  40                  45

Leu Ser Asn Thr Lys Gln Asn Lys Ala Asn Cys Pro Val Cys Lys Ser
    50                  55                  60

Lys Ile Thr Lys Arg Ser Leu Gln Glu Ser Pro Gly Phe Gln Arg Leu
65                  70                  75                  80

Val Ser Gly Leu Gln Glu Ile Ile Leu Ala Tyr Glu Asn Asp Thr Gly
                85                  90                  95

Thr Asn Tyr Phe Thr Gly Leu Ser Lys Gln Ala Gln Pro Pro His Val
            100                 105                 110

Ala Asp Ile Lys Ala Gln His His Asn Lys Val Ser Val Met Asp Ala
        115                 120                 125

Ser Cys Ala Glu Asp Asp Tyr Glu Glu Ala Xaa Pro Lys Ser Gln Ser
    130                 135                 140

Ser Thr Thr Ala Ala Gln Asp Gly Phe Ala Arg Leu Met Gly Leu Lys
145                 150                 155                 160

Asp Thr Ser Pro Leu Thr Thr Gly Leu Asp Ser Gly Leu Gly Glu Ala
                165                 170                 175

Pro Pro Thr Cys Asp Lys Lys Met Tyr Ser Pro Thr Lys Val Glu Asn
            180                 185                 190

Val Pro Leu Xaa Pro Ala Phe Ile Pro Asp Glu Asp Glu Arg Ser Asp
        195                 200                 205

Leu Gln Thr Pro Ser Lys Lys Ser Lys Asp Leu Glu Pro Asp
    210                 215                 220

Lys Ile Leu Asp Gln Arg Gln Lys Lys Ser Leu Glu Lys Val Ala Glu
225                 230                 235                 240
```

```
Trp Leu Met Asn Val Pro Ser Glu Gln Ser Leu Glu Met Glu Asn Pro
                245                 250                 255
Glu Glu Asp Gly Asp Asp Ser Asp Ser Arg Ser Ser Thr Ser Thr Ile
            260                 265                 270
Asp Leu Gly Gln Leu His Arg Gly Thr Asn Pro Thr Arg Gly Arg Ala
        275                 280                 285
Lys Ala Leu Glu Asp Gln Val Phe Gly Ala Val Tyr Lys Arg Glu Arg
    290                 295                 300
Arg Gly Lys Glu Met Val Lys Pro Thr Glu Ala Ala Leu Glu Val Ala
305                 310                 315                 320
Arg Phe Asn Leu Ser Val Glu Asn Thr Ser Glu Asp Glu Asn Arg Asp
                325                 330                 335
Asn Lys Gln Glu Glu His Phe Ile Arg Glu Arg Glu Lys Asn Thr Gly
            340                 345                 350
Ser Asn Val Leu Glu Gly Glu Val Glu Phe Leu Glu Asp Cys Arg Gly
        355                 360                 365
Ser Leu Glu Pro Thr His Met Ser Glu Asn Asp Glu Asn Lys Glu Asp
    370                 375                 380
Glu Val Pro His Pro Val Ser Val Ile Glu Gln Gln Ala Glu Thr
385                 390                 395                 400
Lys Gly Lys Arg Arg Thr Arg Ser Ala Leu Gln Xaa Val Asp Ser Asp
                405                 410                 415
Leu Leu Lys Cys Thr Gln Lys Glu Pro Glu Asn Thr Glu Pro Lys Arg
            420                 425                 430
Thr Gln Lys Arg Ser Arg Gly Ile Lys Ser Glu Arg Ala Lys Ser Ala
        435                 440                 445
Arg Thr Ser Lys Pro Leu Val Leu Val Ala Val Glu Asn Gly Glu Gly
    450                 455                 460
Gly Pro Lys Ile Gly Pro Arg Ser Glu Glu Val Gln Val His Ile Glu
465                 470                 475                 480
Asn Tyr Pro Ser Ser Gly Asp Gln Glu Val Pro Ser Gly Arg Ser Thr
                485                 490                 495
Arg Lys Ser Arg Arg Leu Arg Gly Phe Xaa Lys Glu Asp Thr Gly Lys
            500                 505                 510
Glu Arg Ser Arg Ser Ser Val Pro Glu Lys Glu His Ser Ser Lys His
        515                 520                 525
Pro Lys Phe Glu Cys Glu Thr Leu Asn Asn Val Lys Ser Leu Asp Tyr
    530                 535                 540
Lys Glu Gln Lys Trp Gln Ala Asp Lys Asn Gly Cys Ile Tyr Ser Gln
545                 550                 555                 560
Asp Met Glu Glu Ile Glu Asn Met Asp Ser Gly Glu Lys Xaa Ser Ser
                565                 570                 575
Arg Pro Glu Glu Gly Ser Glu Gln Thr Leu Phe Glu Val Pro Asn Thr
            580                 585                 590
Glu Thr Leu Phe Gln Ala Ala Cys Ser Val Ala Glu Ser Thr Ala Gln
        595                 600                 605
Pro Ser Asn Thr Ala Arg Leu Leu Thr Glu Leu Glu Met Glu Asn Glu
    610                 615                 620
Gln Lys Asn Asp Ser Glu Gln Asp Thr Glu Gln Leu Val Lys Ser Phe
625                 630                 635                 640
Lys Ala Thr Lys Arg Lys Ser Phe His Leu Gly Ser Arg Pro Asp Val
                645                 650                 655
Lys Arg Ser Arg Ser Leu Val Gln Glu Ser Asp Gln Ser Ala Gly Ala
```

```
                   660              665              670
Glu Glu Asn Arg Tyr Val Cys Ser Val Asp Pro Ser Ala Pro Lys Xaa
                675              680              685

Ala Glu Pro Ala Ala Gly Lys Thr Asp Lys Val Leu Val Asp Ser
    690              695              700

Gln Asn Met Pro Gly Ser Asp Leu Ile Ser Asp Ser His Leu Ala Ser
705              710              715              720

Leu Lys Arg Lys Ala Ser Gly Leu Tyr Ser Gly Cys Ser Ala Glu Gly
                725              730              735

Gly Cys Ala Ser Ala Ser Ser Pro Leu Pro Pro Asn Leu Glu Ser Lys
                740              745              750

His Ala Gly Gln Ser Ser Lys Asp Ser Ala Ile Cys Phe Ala Thr Glu
                755              760              765

Lys Pro Ser Gln Ile Ser Gly Ser Gln Ala Asn Phe Met Met Glu Asp
                770              775              780

Thr Gln Ser Ser Thr Leu Leu Gln Ser Val Lys Ala Asp Ala Ala Lys
785              790              795              800

Glu Pro Leu Asn Ala Pro Ser Ser Leu Thr Pro Ser Gly Leu Gln Thr
                805              810              815

Ser Val Pro Gly Gly Glu Met Thr His Ser Gln Ser Ser Arg Glu Leu
                820              825              830

Ser Thr Arg Arg Xaa Arg Thr Lys Ala Gln Lys Leu Asp Cys Leu Ser
                835              840              845

Asp Ser Ser Asp Cys Ala Glu Glu Phe Pro Cys Leu Ala Glu Ile
850              855              860

Leu Asn Glu Thr Ala Ser Pro Gly Glu His Ala Thr Arg Pro Pro Ala
865              870              875              880

Cys Pro Ser Pro Asp Cys Val Asn Ser Ser Gln Ala Ser Val Asp Leu
                885              890              895

Phe Gly Thr Pro His Glu Cys Ala Val Asn Asp Val Ala Ser Ser Gln
                900              905              910

Phe Ser Ser Glu Val Leu Val Thr Gln Gln Lys Ile Glu Met Lys Lys
                915              920              925

Glu Leu Xaa Arg Leu Glu Lys Leu Met Ala Leu Val Ser Glu Val Leu
                930              935              940

His Glu Lys Glu Ala Ser Pro Ala Lys Asp Xaa Leu Asp Lys Thr Lys
945              950              955              960

Gln Lys Ile Thr Gly Ser Asp Val Asp His Val Leu Ser Cys Gly Gln
                965              970              975

Gly Glu Val Phe Asn Gln Glu Thr Phe Pro Glu Glu Glu Gln Asp
                980              985              990

Ala Asn Ala Ser Leu Asn Asp Gly Lys Gly Ala Ala Arg Pro Thr Gly
                995              1000              1005

Ser Lys His Ser Ser Ile Thr Glu Leu Asn Ser Arg Ile Ser Asn
                1010              1015              1020

Thr Val Gly Leu Ser Ser Ala Ala Lys Thr Leu Lys Xaa Asp Gly
    1025              1030              1035

Ser Pro Ser Asp Gly His Glu Asp Lys Glu Asn Thr Pro Glu
    1040              1045              1050

Arg Ala Arg Ser Leu Ala Arg Met Leu Leu Val Thr Ser Gly Leu
    1055              1060              1065

Gly Pro Ser Gln Gln Ile Thr Val Lys Lys Phe Ala Lys Arg Ile
    1070              1075              1080
```

-continued

```
Gly Ala Thr Val Val Ser Gln Val Thr Pro Glu Val Thr His Val
    1085            1090            1095

Val Met His Thr Asp Glu Gln Leu Val Cys Glu Arg Thr Leu Lys
    1100            1105            1110

Tyr Phe Leu Gly Ile Ala Gly Arg Lys Trp Val Val Ser Phe Gln
    1115            1120            1125

Trp Ile Ser Glu Cys Ile Lys Gln Lys Lys Leu Leu Asn Glu Thr
    1130            1135            1140

Leu Phe Glu Val Arg Gly Asp Val Val Asn Gly Phe Asp His Gln
    1145            1150            1155

Gly Pro Met Lys Ala Arg Ala Thr Ala Asp Asn Asn Leu Leu Met
    1160            1165            1170

Lys Gly Tyr Ser Ile Cys Phe Gln Gly Pro Phe Thr Asp Met Thr
    1175            1180            1185

Thr Ala Glu Met Glu Leu Met Val Glu Xaa Cys Gly Ala Thr Val
    1190            1195            1200

Val Gln Asp Pro Leu Leu Leu Asp Gly Lys Arg Thr Ser His Gln
    1205            1210            1215

Leu Ile Val Val Gln Ser Gly Ser Glu Ser Ser Arg Ser Val Ser
    1220            1225            1230

Gly Lys Ala Thr Val Val Thr Arg Gly Trp Leu Leu Asp Ser Val
    1235            1240            1245

Ala Thr Tyr Thr Ile Gln Asn Leu Lys Asn Tyr Arg Ala Asp Leu
    1250            1255            1260

Arg Ala Ala
    1265
```

ISOLATED BRCA1 PEPTIDES AND METHOD OF USE

CROSS REFERENCE TO RELATED APPLICATIONS

This application is a continuation of PCT/US2009/033072 filed on Feb. 4, 2009, which claims priority benefit of U.S. Provisional Application Nos. 61/026,154, filed Feb. 5, 2008, and 61/043,176, filed Apr. 8, 2008, the entire contents of which are incorporated by reference herewith.

STATEMENT OF GOVERNMENT INTEREST

This invention was made with government support under Grant Nos. R37-DK 46071, DK 38652, and CA-96932 awarded by National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Mar. 9, 2009, is named 24978003.txt and is 153,151 bytes in size.

FIELD OF THE INVENTION

The present invention relates to cancer therapy. More particularly, the present invention relates to the development and use of therapeutics for breast and ovarian cancer.

BACKGROUND OF INVENTION

Inherited mutations of the BRCA1 gene are major contributors to hereditary breast and ovarian cancer [1] [2] [3] [4] [5]. However, the mechanisms by which BRCA1 acts as a tumor suppressor are only partially understood [1] [6] [7]. The ability of BRCA1 protein to activate transcription may allow BRCA1 to regulate the cell cycle [8] [9]. Overexpression of BRCA1 blocks growth of breast and ovarian cancer cell lines [10]. Moreover, BRCA1 associates with Rad51, which is important for efficient DNA recombination [11] [12], both in mitotic and meiotic cells [13], suggesting a role for BRCA1 in the preservation of genome integrity [1].

BRCA1 is a co-activator of transcription, given that it is part of the RNA polymerase II holoenzyme and that it functions as a transactivator [7] [9] [13] [14] [15]. Because the tumor suppressor p53 [16] [17] plays a major role in DNA repair processes [18] as well as in the cell cycle arrest triggered by DNA damage [19] [20] [21], characterizing the interactions between BRCA1 and p53 are relevant, particularly under conditions that induce DNA damage, for understanding hereditary breast and ovarian cancer.

Zhang et al [15] reported that BRCA1 (amino acids 224-500) interacts physically with p53 (amino acids 300-393) and that stimulates p53-transactivation and apoptosis. This interaction was identified only in vitro, and cell experiments have not been done with mutations or deletions of this BRCA1 region, nor using mammary or ovarian cells. Moreover, both the p53 C-terminus (amino acids 311-393), which contains the tetramerization domain, and the p53 basic region (amino acids 355-393) bind to BRCA1 (amino acids 224-500) domain with relatively weak affinity [22]. Therefore, it is not clear how biologically relevant is the binding of the BRCA1 (224-500) with the p53 C-terminal domain [22].

Computer analysis has suggested the presence of a probable p53 binding domain in the C-terminus of BRCA1 (BRCT) [23] [24], a module present in proteins involved in DNA repair [25], since it is analogous to the p53 binding domain of 53BP1 [23] [26]. Although it has been also reported that the second BRCT domain of BRCA1 protein may interact with p53 [27], quantitative biophysical measurements indicate that this region of BRCA1 does not bind to p53 [28]. Thus, it is uncertain whether these regions (or others) within BRCA1 reported to interact with p53 [15] [27] are critical for the apoptotic and transactivation effects of BRCA1 [15] [28].

SUMMARY OF THE INVENTION

The present invention provides an isolated peptide, peptidomimetic, and/or synthetic protein comprising a BRCA1 domain comprising amino acids 772-1292 (SEQ ID NO:1), more preferably, amino acids 904-1292 (SEQ ID NO:11), and peptides substantially identical thereto, that stimulates p53 DNA binding and transcription activities and apoptosis. In one preferred embodiment, the isolated peptide has an amino acid sequence as set forth in SEQ ID NO:1. In yet another preferred embodiment, the invention provides an isolated nucleic acid encoding a peptide having an amino acid sequence as set forth in SEQ ID NO:1. The present invention further provides use of the isolated peptide, peptidomimetic, and/or a synthetic protein and their analogs for treating cancer, preferably breast and ovarian cancer. Any techniques known to those of skill in the art for producing such peptides, including, but not limited to, the expression of peptides through standard molecular biological recombinant techniques including the isolation of peptides or proteins from natural sources, or the chemical synthesis of peptides or proteins are within the scope of the present invention.

The present invention also provides an isolated nucleic acid, homologs and analogs that encode a peptide, comprising a BRCA1 domain, preferably comprising amino acids 772-1292 (SEQ ID NO:1), or amino acids 904-1292 (SEQ ID NO:11), or biologically active portions thereof. The invention provides nucleic acids that hybridize at highly stringent conditions to a nucleotide sequence encoding the amino acids 772-1292 (SEQ ID NO:1), more preferably, amino acids 904-1292 (SEQ ID NO: 11), of the BRCA1 domain, or portions thereof, that binds to p53. Moreover, the present invention provides nucleotides, homologs and analogs that comprise the nucleotide sequences encoding the amino acids 772-1292 (SEQ ID NO:1), or amino acids 904-1292 (SEQ ID NO:11) of the BRCA1 domain, or complements thereof. In one preferred embodiment, the isolated nucleotide encodes a peptide comprising an amino acid sequence as set forth in SEQ ID NO:1, or portions thereof, or encodes a nucleic acid, hybridize at highly stringent conditions to the nucleotide sequence, or a complement thereof, encoding the amino acids as set forth in SEQ ID NO:1. The invention provides methods of expressing such nucleic acids for isolation and administration to a patient in need, and expressly such nucleic acids within the patient.

The present invention futher provides a pharmaceutical composition for treating breast and ovary cancer comprising an isolated peptide, peptidomimetic, and/or a synthetic protein comprising a BRCA1 domain comprising amino acids 772-1292 (SEQ ID NO: 1), or amino acids 904-1292 (SEQ ID NO: 11). The present invention also provides a pharmaceutical composition for treating breast and ovary cancer comprising the isolated peptide, peptidomimetic, and/or synthetic protein disclosed herein, and a pharmaceutically acceptable carrier or vehicles. In one preferred embodiment, the present invention provides a pharmaceutical composition for treating breast and ovary cancer comprising an isolated peptide comprising an amino acid sequence as set forth in SEQ ID NO:1 or 11, or portions thereof.

BRIEF DESCRIPTION OF THE DRAWINGS

FIG. 1 illustrates that BRCA1 is associated with p53 in breast cancer cells.

FIG. 2 illustrate that BRCA1 (772-1292, SEQ ID NO:1) induces apoptosis and p21 expression in breast cancer cells.

FIG. 3 illustrates that BRCA1 and p53 form a complex with p53 cognate DNA.

FIG. 4 illustrates that BRCA1 augmented p53 transcriptional activity.

DETAILED DESCRIPTION OF THE INVENTION

Figure 1A:
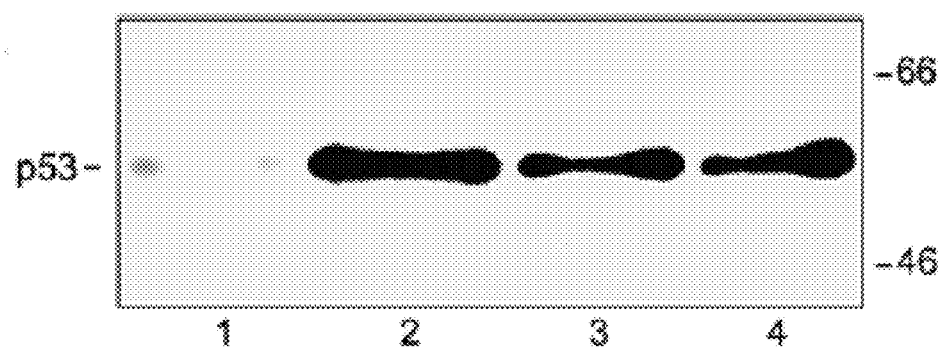
FIG. 1A represents a western blot of p53 in BRCA1 immunoprecipitates. HBL-100 cells, control (lane 1), exposed to UV-B light for 5 min (lane 2) or 10 min (lane 3), or treated with adriamycin for 24 h (0.2 μg ml$^{-1}$) (lane 4) were lysed after 24 h and immunoprecipitated with purified anti-BRCA1 N-terminus (K-18; Santa Cruz). A representative immunoblot for p53 was performed in BRCA1 immunoprecipitates with monoclonal p53 antibodies (Bp53-12; Santa Cruz). Five hundred μg of total protein was used in each immunopurification. Molecular weight markers are shown.

The present invention provides BRCA1 compounds, preferably peptides, or analogs thereof, that stimulate p53 DNA binding and transcription activities and apoptosis for preventing or treating breast and/or ovarian cancer. More particularly, the present invention provides an isolated peptide, peptidomimetic, and/or synthetic protein corresponding to a BRCA1 domain between amino acids 772-1292 and any cancer inhibiting proteins thereof including amino acids 772-1292 (SEQ ID NO:1), preferably, amino acids 904-1292 (SEQ ID NO:11), that stimulates p53 DNA binding and transcription activities and cancer cell apoptosis. In one of the preferred embodiments, the present invention provides an isolated peptide comprising an amino acid sequence of SEQ ID NO:1, or portions thereof. In yet another embodiments, the present invention provides an isolated peptide having an amino acid sequence that is at least between 90% and 96% identical to SEQ ID NO:1.

The interactions between BRCA1 and p53 are relevant for treating hereditary breast and ovarian cancer. Although in vitro studies reported that BRCA1 (amino acids 224-500) and the second BRCT domain of the BRCA1 C-terminus may interact with p53, quantitative biophysical measurements indicate that these regions of BRCA1 do not bind efficiently to p53. The present invention provides that BRCA1 interacts with p53 in vivo in breast cancer cells, through another BRCA1 domain e.g., amino acids 772-1292 (e.g., SEQ ID NO:1), or amino acids 904-1292 (SEQ ID NO:11). It was found that expression of a truncated BRCA1 including amino acids 772-1292 (e.g. SEQ ID NO:1) stimulated p53 DNA binding and transcription activities and apoptosis, recapitulating some effects of DNA damage. These results indicate that a novel domain of BRCA1 interacts with p53 in breast cancer cells, and provide additional mechanisms by which BRCA1 affects transcription and the cellular responses to DNA damage. Dysfunction of the BRCA1 domain that associates with p53, induced by oncogenic pathways or BRCA1 mutations, may confer susceptibility to breast and ovarian cancer and therefore, provides a diagnostic assay.

As used herein, the term "compound" refers to any chemical substances consisting of two or more different chemically bonded chemical elements with a determining composition. The "compound" used herein can be either naturally occurred (endogenous compounds) or chemically synthesized, including but not limited to any peptides, proteins, polynucleotides, oligonucleotides (antisense oligonucleotide agents), ribozymes, dsRNAs, RNAi, siRNAs, gene therapy vectors, vaccines, antibodies. Any techniques known to those of skill in the art for producing such compounds, including but not limited to the expression of peptides or proteins through standard molecular biological techniques including recombinant techniques, the isolation of peptides or proteins from natural sources, or the chemical synthesis of compounds are within the scope of the present invention.

As used herein, the term "peptide" refers to a chain of at least three amino acids joined by peptide bonds. The terms "peptide" and "protein" are used interchangeably herein. The chain may be linear, branched, circular, or combinations thereof. As used herein, the term "analogs" refers to two amino acids that have the same or similar function, but that have evolved separately in unrelated organisms. As used herein, the term "analog" further refers to a structural derivative of a parent compound that often differs from it by a single element. As used herein, the term "analog" also refers to any peptide modifications known to the art, including but are not limited to changing the side chain of one or more amino acids or replacing one or more amino acid with any non-amino acids.

In certain embodiments the peptides and analogs of the present invention are isolated or purified. Protein purification techniques are well known in the art. These techniques involve, at one level, the homogenization and crude fractionation of the cells, tissue or organ to peptide and non-peptide fractions. The peptides of the present invention may be further purified using chromatographic and electrophoretic techniques to achieve partial or complete purification for purification to homogeneity). Analytical methods particularly suited to the preparation of a pure peptide are ion-exchange chromatography, gel exclusion chromatography, polyacrylamide gel electrophoresis, affinity chromatography, immunoaffinity chromatography and isoelectric focusing. A particularly efficient method of purifying peptides is fast protein liquid chromatography (FPLC) or even HPLC.

An isolated peptide is intended to refer to a peptide/protein that is purified to any degree relative to its naturally-occurring state. Therefore, an isolated or purified peptide refers to a peptide free from at least some of the environment in which it may naturally occur. Generally, "purified" will refer to a peptide composition that has been subjected to fractionation to remove various other components, and which composition substantially retains its expressed biological activity. Where the term "substantially purified" is used, this designation will refer to a composition in which the peptide forms the major component of the composition, such as constituting about 50%, about 60%, about 70%, about 80%, about 90%, about 95%, or more of the peptides in the composition.

Various methods for quantifying the degree of purification of the peptide are known in the art. These include, for example, determining the specific activity of an active fraction, or assessing the amount of peptides within a fraction by SDS/PAGE analysis. Various techniques suitable for use in peptide/protein purification are well known to those of skill in the art. These include, for example, precipitation with ammonium sulphate, PEG, antibodies and the like, or by heat denaturation, followed by; centrifugation; chromatography steps such as ion exchange, gel filtration, reverse phase, hydroxylapatite and affinity chromatography, isoelectric focusing; gel electrophoresis; and combinations of these and other techniques. As is generally known in the art, it is believed that the order of conducting the various purification steps may be changed, or that certain steps may be omitted, and still result in a suitable method for the preparation of a substantially purified protein or peptide.

There is no general requirement that the peptides and their analogs always be provided in their most purified state. Indeed, it is contemplated that less substantially purified products will have utility in certain embodiments. Partial purification may be accomplished by using fewer purification steps in combination, or by utilizing different forms of the same general purification scheme. Methods exhibiting, a lower degree of relative purification may have advantages in total recovery of protein product, or in maintaining the activity of an expressed protein. The invention contemplates compositions comprising the peptides and a pharmaceutically acceptable carrier.

In certain embodiments, the peptides and their analogs of the present invention may be attached to imaging agents including but are not limited to fluorescent, and/or radioisotopes including but are not limited to $^{125}$I, for imaging, diagnosis and/or therapeutic purposes. Many appropriate imaging agents and radioisotopes are known in the art, as are methods for their attachment to the peptides.

The present invention also provides isolated nucleotides, homologs and analogs comprising the nucleotide sequences encoding the aforementioned BRCA1 domains including the fragments comprising approximately amino acids 772-1292 (SEQ ID NO:1), or amino acids 904-1292 (SEQ ID NO:11), that stimulates p53 DNA binding and transcription activities and cancer cell apoptosis. In one embodiment, the present invention provides an isolated nucleotide encoding a peptide having amino acid sequence of SEQ ID NO: 1, or functional fragment thereof.

As used herein, the "nucleic acids" or "nucleotides" may be derived from genomic DNA, complementary DNA (cDNA) or synthetic DNA. The term "nucleic acid" or "nucleotide" also refer to RNA or DNA that is linear or branched, single or double stranded, chemically modified, or a RNA/DNA hybrid thereof. Where incorporation into an expression vector is desired, the nucleic acid may also comprise a natural intron or an intron derived from another gene. Less common bases, such as inosine, 5-methylcytosine, 6-methyladenine, hypoxanthine, and others can also be used.

An "isolated" nucleic acid molecule is one that is substantially separated from other nucleic acid molecules which are present in the natural source of the nucleic acid (i.e., sequences encoding other polypeptides). Preferably, an "isolated" nucleic acid is free of some of the sequences which naturally flank the nucleic acid (i.e., sequences located at the 5' and 3' ends of the nucleic acid) in its naturally occurring replicon. For example, a cloned nucleic, acid is considered isolated. A nucleic acid is also considered isolated if it has been altered by human intervention, or placed in a locus or location that is not its natural site, or if it is introduced into a cell by agroinfection. Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized.

As used herein, "homologs" are defined herein as two nucleic acids or peptides that have similar, or substantially identical, nucleic acids or amino acid sequences, respectively. The term "homolog" further encompasses nucleic acid molecules that differ from one of the nucleotide sequences due to degeneracy of the genetic code and thus encodes the same amino acid sequences. In one of the preferred embodiments, homologs include allelic variants, orthologs, paralogs, agonists, and antagonists of nucleic acids encoding the peptide, or analogs thereof, of the present invention.

As used herein, the term "orthologs" refers to two nucleic acids from different species, but that have evolved front a common ancestral gene by speciation. Normally, orthologs encode peptides having the same or similar functions. In particular, orthologs of the invention will generally exhibit at least 80-85%, more preferably 85-90% or 90-95%, and most preferably 95%, 96%, 97%, 96%, or even 99% identity, or 100% sequence identity, with all or part of the amino acid sequence of the BRCA1 peptides, or analogs thereof, of the present invention, preferably, SEQ ID NO:1, or mutants thereof, and will exhibit a function similar to the BRCA1 peptides. Preferably, the orthologs of the present invention are BRCA1 peptide stimulates p53 DNA binding and transcription activities and cancer cell apoptosis. As also used herein, the term "paralogs" refers to two nucleic acids that are related by duplication within a genome. Paralogs usually have different functions, but these functions may be related.

To determine the percent sequence identity of two amino acid sequences e.g., SEQ ID NO:1, and a mutant form thereof), the sequences are aligned for optimal comparison purposes (e.g., gaps can be introduced in the sequence of one polypeptide for optimal alignment with the other polypeptide or nucleic acid). The amino acid residues at corresponding amino acid positions are then compared. When a position in one sequence (e.g., SEQ ID NO:1) is occupied by the same amino acid residue as the corresponding position in the other sequence (e.g., a mutant form of the sequence selected from the peptide sequences of SEQ ID NO:1), then the molecules are identical at that position. The same type of comparison can be made between two nucleic acid sequences.

The percent sequence identity between the two sequences is a function of the number of identical positions shared by the sequences percent sequence identity=numbers of identical positions/total numbers of positions×100). Preferably, the isolated amino acid or nucleic acid homologs included in the present invention are at least about 50-60%, preferably at least about 60-70%, and more preferably at least about 70-75%, 75-80%, 80-85%, 85-90%, or 90-95%, and most preferably at least about 96%, 97%, 98%, 99%, or more identical to an entire amino acid or nucleic acid sequence of the aforementioned BRCA1 domain including those comprising the amino acids 772-1292, (SEQ ID NO:1) or amino acids 904-1292, or (SEQ ID NO:11). In one preferred embodiment, the isolated nucleic acid homologs of the present invention encode a peptide of the BRCA1 domain comprising an amino acids sequence, that is at least 90%, more preferably at least 95% identical to an amino acid sequence of SEQ ID NO:1 or SEQ ID NO:11, and stimulates p53 DNA binding and transcriptional activites and cancer cell apoptosis.

The determination of the percent sequence identity between two nucleic acid or peptide sequences is well known in the art. For instance, the Vector NTI 6.0 (PC) software package (InforMax, 7600 Wisconsin Ave., Bethesda, Md. 20814) to determine the percent sequence identity between two nucleic acid or peptide sequences can be used. In this method, a gap opening penalty of 15 and a gap extension penalty of 6.66 are used for determining the percent identity of two nucleic acids. A gap opening, penalty of 10 and a gap extension penalty of 0.1 are used for determining the percent identity of two polypeptides. All other parameters are set at the default settings. For purposes of a multiple alignment (Clustal W algorithm), the gap opening penalty is 10, and the gap extension penalty is 0.05 with blosum62 matrix. It is to be understood that for the purposes of determining sequence identity when comparing a DNA sequence to an RNA sequence, a thymidine nucleotide is equivalent to a uracil nucleotide.

In another aspect, the present invention provides an isolated nucleic acid comprising a nucleotide sequence that hybridizes to the nucleotides encoding the amino acid sequence shown in SEQ ID NO:1 or SEQ ID NO:11 under stringent conditions, and stimulates p53 DNA binding and transcriptional activities, causing cancer cell apoptosis. As used herein with regard to hybridization for DNA to a DNA blot, the term "stringent conditions" refers to hybridization overnight at 60° C. in 10× Denhart's solution, 6×SSC, 0.5% SDS, and 100 µg/ml denatured salmon sperm DNA. Blots are washed sequentially at 62° C. for 30 minutes each time in 3×SSC/0.1% SDS, followed by 1×SSC/0.1% SDS, and finally 0.1×SSC/0.1% SDS. As also used herein, in a preferred embodiment, the phrase "stringent conditions" refers to hybridization in a 6×SSC solution at 65° C. In another embodiment, "highly stringent conditions" refers to hybridization overnight at 65° C. in 10× Denhart's solution, 6×SSC, 0.5% SDS and 100 µg/ml denatured salmon sperm DNA. Blots are washed sequentially at 65° C. for 30 minutes each time in 3×SSC/0.1% SDS, followed by 1×SSC/0.1% SDS, and finally 0.1×SSC/0.1% SDS. Methods for nucleic acid hybridizations are described in Meinkoth and Wahl, 1984, Anal. Biochem. 138:267-284; Current Protocols in Molecular Biology, Chapter 2, Ausubel et al., eds., Greene Publishing, and Wiley-Interscience, New York, 1995; and Tijssen, 1993, Laboratory Techniques in Biochemistry and Molecular Biology: Hybridization with Nucleic Acid Probes, Part I, Chapter 2, Elsevier, N.Y., 1993.

Using the above-described methods, and others known to those of skill in the art, one of ordinary skill in the art can isolate from nature or create homologs of the aforementioned PCA 1 peptide. One subset of these homologs are allelic variants. As used herein, the term "allelic variant" refers to a nucleotide sequence containing polymorphisms that lead to changes in the amino acid sequences of the peptides of the present invention without altering the functional activities. Such allelic variations can typically result in 1-5% variance in nucleic adds encoding the BRCA1 peptide of the present invention.

In addition, the skilled artisan will further appreciate that changes can be introduced by mutation into a nucleotide sequence that encodes the amino acid sequence of the aforementioned BRCA1 peptide, or analog, thereof. For example, nucleotide substitutions leading to amino acid substitutions at "non-essential" amino acid residues can be made in a sequence encoding the amino acid sequence of the peptides, or analogs thereof, of the present invention. A "non-essential" amino acid residue is a residue that can be altered without altering the activity of said peptide, whereas an "essential" amino acid residue is required for desired activity of such peptide, such as enhance or facilitate transdermal delivery of any drugs.

In one embodiment, the isolated nucleic acid molecule comprises a nucleotide sequence encoding the aforementioned BRCA1 peptide, wherein the aforementioned BRCA1 peptide comprises an amino acid sequence at least about 50% identical to an amino acid sequence of SEQ ID NO:1 or SEQ ID NO:11. Preferably, the peptide encoded by the nucleic acid molecule is at least about 50-60% identical to an amino acid sequence of SEQ ID NO:1 or SEQ NO:11, more preferably at least about 60-70% identical, even more preferably at least about 70-75%, 75-80%, 80-85%, 85-90%, or 90-95% identical, and most preferably at least about 96%, 97%, 98%, 99%, 99.5% OR 99.8% identical to an amino acid sequence of SEQ ID NO:1 or SEQ ID NO:11.

An isolated nucleic acid molecule encoding the aforementioned BRCA1 peptide of the present invention can be created by introducing one or more nucleotide substitutions, additions, or deletions into a nucleotide encoding the peptide sequence, such that one or more amino acid substitutions, additions, or deletions are introduced into the encoded peptide and/or the side chain of the amino acids constituting the encoded peptides. Mutations can be introduced into the nucleic acid sequence encoding the peptide sequence of the present invention by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain.

Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine). Following mutagenesis of the nucleic acid sequence encoding the aforementioned BRCA1 peptide of the present invention, the encoded BRCA1 peptide can be expressed recombinantly.

The nucleotides of the present invention may be produced by any means, including genomic preparations, cDNA preparations, in vitro synthesis, RT-PCR, and in vitro or in vivo transcription. It is contemplated that peptides of the present invention, their variations and mutations, or fusion peptides/proteins may be encoded by any nucleic acid sequence that encodes the appropriate amino acid sequence. The design and production of nucleic acids encoding a desired amino acid sequence is well known to those of skill in the art based on standardized codons. In preferred embodiments, the codons selected for encoding each amino acid may be modified to optimize expression of the nucleic acid in the host cell of interest. Codon preferences for various species of host cell are well known in the art.

Any peptides and their analogs comprising the isolated peptides of the present invention can be made by any techniques known to those of skill in the art, including but are not limited to the recombinant expression through standard molecular biological techniques, the conventional peptide/protein purification and isolation methods, and/or the synthetic chemical synthesis methods. The nucleotide and peptide sequences corresponding to various genes may be found at computerized databases known to those of ordinary skill in the art, for instance, the National Center for Biotechnology Information's Genbank and GenPept databases (National Center for Biotechnology Information). Alternatively, various commercial preparations of proteins and peptides are known to those of skill in the art.

Because the length of the isolated peptides of the present invention is relatively short, peptides and analogs comprising the amino acid sequences of these isolated peptide inserts can be chemically synthesized in solution or on a solid support in accordance with conventional techniques. Various automatic synthesizers are commercially available and can be used in accordance with known protocols. Short peptide sequences, usually from about 6 up to about 35 to 50 amino acids, can be readily synthesized by such methods. Alternatively, recombinant DNA technology may be employed wherein a nucleotide sequence which encodes a peptide and its analog of the present invention is inserted into an expression vector, transformed or transfected into an appropriate host cell, and cultivated under conditions suitable for expression.

Peptide mimetics may also be used for preparation of the peptides and their analogs of the present invention. Mimetics are peptide-containing molecules that mimic elements of protein secondary structure. A peptide mimetic is expected to permit molecular interactions similar to the natural molecule, and may be used to engineer second generation molecules having many of the natural properties of the peptides, but with altered and even improved characteristics.

The present invention also provides chimeric or fusion peptides that comprise the aforementioned BRCA1 compounds, peptides, and/or analogs thereof. As used herein, a "chimeric or fusion peptide" comprises the amino acid sequence corresponding to the amino acid sequence of the aformentioned BRCA1 peptides, or analogs thereof, operatively linked, preferably at the N- or C-terminus, to all or a portion of a second peptide or protein. As used herein, "the second peptide or protein" refer to a peptide or protein having an amino acid sequence which is not substantially identical to the amino acid sequences of the aforementioned BRCA1 peptide, analogs, or mutants thereof, e.g., a peptide or protein that is different from SEQ ID NO:1 and is derived from the same or a different organism. With respect to the fusion peptide, the term "operatively linked" is intended to indicate that the amino acid of the peptides, or analogs thereof, of the present invention, and the second peptide or protein are fused to each other so that both sequences fulfill the proposed function attributed to the sequence used.

For example, fusions may employ leader sequences from other species to permit the recombinant expression of a protein in a heterologous host. Another useful fusion includes the addition of an immunologically active domain, such as an antibody epitope, to facilitate purification of the fusion protein. Inclusion of a cleavage site at or near the fusion junction will facilitate removal of the extraneous poly peptide after purification. Other useful fusions include linking of functional domains, such as active sites from enzymes, glycosylation domains, cellular targeting signals or transmembrane regions. In preferred embodiments, the fusion proteins of the present invention comprise the peptide and/or analog comprising amino acid sequences of the displayed peptide identified from the in vivo phage display, that is linked to a therapeutic protein or peptide. Examples of proteins or peptides that may be incorporated into a fusion protein include cytostatic proteins, cytocidal proteins, pro-apoptosis agents, anti-angiogenic agents, hormones, cytokines, growth factors, peptide drugs, antibodies, Fab fragments antibodies, antigens, receptor proteins, enzymes, lectins, MHC proteins, cell adhesion proteins and binding proteins. These examples are not meant to be limiting and it is contemplated that within the scope of the present invention virtually any protein or peptide could be incorporated into a fusion protein comprising the peptides and analogs of the present invention. Furthermore, in certain preferred embodiments, the fusion proteins of the present invention exhibit enhanced transdermal penetration capability as compared to non-fusion proteins or peptides that have not fused with the peptides and analogs, as disclosed herein.

Methods of generating fusion peptides/proteins are well known to those of skill in the art. Such peptides/proteins can be produced, for example, by chemical attachment using bifunctional cross-linking reagents, by de novo synthesis of the complete fusion peptide/protein, or by standard recombinant DNA techniques that involve attachment of a DNA sequence encoding the peptides of present invention, as disclosed herein, to a DNA sequence encoding the second peptide or protein, followed by expression of the intact fusion peptide/protein using. For example, DNA fragments coding for the peptide sequences of the peptides, or analogs thereof, of the present invention, are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and re-amplified to generate a chimeric gene sequence (See, for example, Current Protocols in Molecular Biology, Eds. Ausubel et al., 1992, John Wiley & Sons). Moreover, many expression vectors are commercially available that already encode a fusion moiety (e.g., a GST polypeptide). The nucleic acids encoding the aforementioned BRCA1 compounds, peptides, analogs, or mutants thereof, can be cloned into such an expression vector such that the fusion moiety is linked in-frame to these nucleic acids encoding the aforementioned BRCA1 peptides, or analogs or mutants thereof.

The present invention further provides antibodies and/or vaccines generated from, and/or comprising the aforementioned BRCA1 compounds, peptides, analogs thereof, of the present invention for preventing or treating breast and/or ovarian cancer. The term "antibody" includes complete antibodies, as well as fragments thereof (e.g., F(ab')2, Fab, etc.) and modified antibodies produced therefrom (e.g., antibodies modified through chemical, biochemical, or recombinant DNA methodologies), with the proviso that the antibody fragments and modified antibodies retain antigen binding characteristics sufficiently similar to the starting antibody so as to provide for specific detection of antigen.

Antibodies may be prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see Monoclonal Antibodies: A Laboratory Manual, Harlow and Lane eds., Cold Spring Harbor Laboratories, Cold Spring Harbor, N.Y. 1988. If desired, the mRNA encoding the heavy and light chains may be isolated and mutagenized by cloning in *E. coli*, and the heavy and light chains mixed to further enhance the affinity of the antibody. Alternatives to in vivo immunization as a method of raising antibodies include binding to phage display libraries, usually in conjunction with in vitro affinity maturation.

As used herein, the term "vaccine" refers to a product that produces immunity therefore protecting the body from the disease. Vaccines that comprise a suspension of attenuated or killed microorganism (e.g. bacterial, viruses, or) are administered for the prevention, amelioration or treatment of infectious diseases. In preferred embodiments, the present invention provides vaccines generated from, and/or comprising the aforementioned BRCA1 compounds, peptides, mutants, or analogs thereof.

The present invention further provides a pharmaceutical composition for preventing and/or treating breast and/or ovarian cancer comprising the aformentioned BRCA1 compounds, peptides, mutants, or analogs thereof, of the present invention, and a pharmaceutically acceptable carrier and/or excipient. Pharmaceutically acceptable carriers and/or excipients are well known in the art, and have been amply described in variety of publications, including, for example, "Remington: The Science and Practice of Pharmacy", $19^{th}$ Ed. (1995).

The present invention further comprises methods for preventing or treating breast and/or ovarian cancer comprising administering to a subject in need an effective amount of a pharmaceutical composition comprising the aforementioned BRCA1 compounds, peptides, mutants, analogs, antibodies, vaccine thereof. In preferred embodiments, the aforementioned BRCA1 compounds, peptides, mutants, analogs, antibodies, or vaccines thereof, can be used as a therapeutic agent for treating breast and/or ovarian cancer. As used herein, the term "therapeutic agent," "or "drug" is used interchangeably to refer to a chemical material or compound that treating cancer.

In yet another preferred embodiment, the aforementioned BRCA1 compounds, peptides, mutants, analogs, antibodies, vaccines thereof, can also be incorporated into vectors/virus and used for gene therapy. The term "gene therapy" refers to a technique for correcting defective genes responsible for disease development. Such techniques may include inserting a normal gene into a nonspecific location within the genome to replace a nonfunctional gene; swapping an abnormal gene for a normal gene through homologous recombinations, repairing an abnormal gene to resume its normal function through selective reverse mutation; and altering or regulating gene expression and/or functions of a particular gene. In most gene therapy, a normal gene is inserted into the genome to replace an abnormal or disease-causing gene.

As used herein, a term "vector/virus" refers to a carrier molecule that carries and delivers the "normal" therapeutic gene to the patient's target cells. Because viruses have evolved a way of encapsulating and delivering their genes to human cells in a pathogenic manner, most common vectors for gene therapy are viruses that have been genetically altered to carry the normal human DNA. As used herein, the viruses/vectors for gene therapy include retroviruses, adenoviruses, adeno-associated viruses, and herpes simplex viruses. The term "retrovirus" refers to a class of viruses that can create double-stranded DNA copies of their RNA genomes, which can be further integrated into the chromosomes of host cells.

As used herein, the terms "treatment," "treating," and the like, refer to obtaining a desired pharmacologic and/or physiologic effect. The effect may be prophylactic in terms of completely or partially preventing a symptom thereof and/or may be therapeutic in terms of a partial or complete cure for an adverse affect attributable to the condition. "Treatment," as used herein, covers any treatment of an injury in a mammal, particularly in a human, and includes: (a) preventing formation of cancer cells, arresting any complications, and minimizing its effects; (b) relieving the symptoms; (c) preventing the disease from occurring in a subject which may be predisposed to the disease but has not yet been diagnosed as having it; (d) inhibiting the disease, i.e., arresting its development; and (e) relieving the disease, i.e., causing regression of the disease.

As used herein, the term "individual," "host," "subject," and "patient" are used interchangeably herein, and refer to a mammal, including, but not limited to, murines, simians, humans, mammalian farm animals, mammalian sport animals, and mammalian pets, preferably, humans.

As used herein, the term "effective amount" or "therapeutically effective amount" means a dosage sufficient to provide treatment of the disease state being treated or to otherwise provide a desired pharmacologic and/or physiologic effect.

These and many other variations and embodiments of the invention will be apparent to one of skill in the art upon a review of the appended description and examples.

EXAMPLES

Materials and Methods
Cell Cultures

Human diploid HBL-100 mammary epithelial cancer, human osteosarcoma SAOS and human colon carcinoma HCT116 cell line derivative, 80S14p21-/-cells were cultured in McCoy's media with 10% fetal calf serum, MCF-7 breast cancer cells were cultured in Earle's MEM supplemented with 1 mM Na pyruvate, nonessential amino acids and bovine insulin (10 µg ml$^{-1}$) (Clonetics). HBL-100, SAOS, 80S14 and MCF-7 cells were from the ATTC. The human lymphoblastoid cell line (GM13713) was cultured as recommended by Coriell Cell Repositories.
Co-Immunoprecipitation and Immunoblots HBL-100 and MCF-7 cells were exposed to UV light (6,600 microwatt seconds per square centimeter), or treated with adriamycin (0.2 µg ml$^{-1}$) for 24 h. Immunoprecipitation of BRCA1, p53, p21 and cytochrome C was performed using specific antibodies (Santa Cruz Biotechnologies) as described [29], immunoprecipitation reactions contained 500 µg total protein cell lysate and 2 µg antibody. Immunoprecipitated proteins were resolved by SDS-PAGE, and detection of BRCA1, p53, p21, cytochrome C, and APAF-1 by western blot was performed as described [30] following the chemiluminescence protocol (DuPont) using specific antibodies against BRCA1 (K-18), p53 (Bp53-12), p21 (C-19; amino acids 146-164), cytochrome C and APAF-1 (Santa Cruz). Immunoblots shown were quantified on a Kodak 4000 Imaging Station and software.
Plasmids The various BRCA1 truncations: 1-1710 (SEQ ID NO:4) 1-1409 (SEQ ID NO:12) 1-1292 (SEQ ID NO:5); 1-904 (SEQ ID NO:6) and 1-472 (SEQ ID NO:7) were inserted into a pcDNA 3 vector (Invitrogen). The BRCA1 domains: 772-1292 (SEQ ID NO:1) and 772-1036 (SEQ ID NO:8) were fused to a vector containing an N-terminus influenza hemagglutinin (HA) epitope [31]. The restriction sites utilized in the cloning of these vectors included AFIII (amino acids 472); KpnI (amino acids 772); DraI (amino acids 1036) and NheI (amino acids 1292). Exonuclease digestion with Exo II (Stratagene), followed by Mung Bean nuclease to generate blunt ends, was used to produce vectors expressing BRCA1(1-904) (SEQ ID NO:6); BRCA1(1-1409) (SEQ ID NO:12) and BRCA1(1-1710) (SEQ ID NO:4) [32].

Transfections

HBL-100, SAOS, 80S14 and MCF-7 cells were transfected with 2 µg DNA as described [33] using 60 µg of superfect (Qiagen). The BAX-Luc promoter reporter vector (1 µg) was transfected with vectors expressing p53 or BRCA1 wt or truncated proteins. The $PG_{13}$-CAT or $MG_{15}$-CAT plasmids [20] (1 µg) were transfected with either pcDNA (lacking BRCA1 or p53 sequences), p53, BRCA1 wt, BRCA1 (109-1863) (SEQ ID NO:13), BRCA1 (772-1292) (SEQ ID NO:1), BRCA1 (1292-1863) (SEQ ID NO:14) or BRCA1 (772-1036) (SEQ ID NO:8). Cells were harvested 24 h after transfection and the CAT content was determined by ELISA (5' Prime 3' Prime) and Luc expression by a luciferase assay as described [34]. For immunohistochemistry, cells were fixed at room temperature with 10% buffered formaldehyde for 20 min, followed by 70% ethanol for 5 min. Apoptotic cells were identified by in vivo annexin-V-FITC (Molecular Probes) binding and DNA staining of apoptotic cells with DAPI [35] (Sigma) using a dual channel fluorescent microscope as described [36]. The Annexin-V-FITC binding was quantified after cell sorting for FITC, using a Kodak 4000 Imaging Station and software.

Gel Retardation Assay

Nuclei extracts were prepared as described [33]. Cells were homogenized in 5% citric acid, 0.5% NP-40, 10 mM NaF, 10 mM Na pyrophosphate and 10 µM butylated hydroxytoluene (to inhibit phosphatases and spurious oxidative stress) with a glass Dounce homogenizer with a loose fitting pestle. The homogenized cells were placed above a cushion consisting of 30% sucrose and 1% citric acid. The nuclei were precipitated by a 4000×g centrifugation at 4° C. for 20 min and lysed [29]. DNA concentrations were determined by spectrophotometric absorbance at 260 nm. Nuclear extracts containing 5 µg of DNA were utilized per lane. Where indicated, nuclear extracts were preincubated with up to 2 µg of purified antibodies for 45 min at room temperature. Gel retardation analysis of protein-DNA complexes was performed in the presence of poly-dIdC with an oligonucleotide spanning the p53 binding site of the p21 gene [20], as described previously [37]. The oligonucleotides were p53 consensus binding site having an amino acid sequence of 5' TAC AGA ATC GCT CTA AGC ATG CTG GGG 3' (SEQ ID NO:2) and p53 mutant having an amino acid sequence of 5 TAC AGA ACA TGT CTA AGC ATG CTG GGG 3' (SEQ ID NO:3) (Santa Cruz).

Example 1

BRCA1 Associated with p53 in Breast Cancer Cells

Figure 1B:
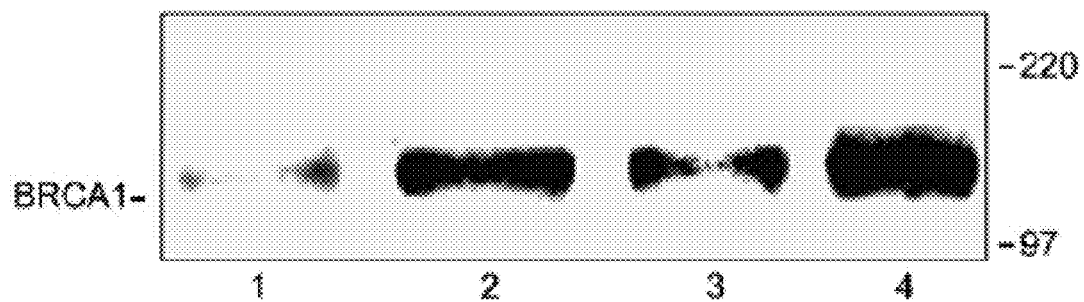
FIG. 1B represents a western blot of BRCA1 in p53 immunoprecipitates. Immunoprecipitation of p53 was done using monoclonal p53 antibodies (Bp53-12) in the HBL-100 cell lysates described in FIG. 1A. A representative BRCA1 immunoblot was performed in p53 immunoprecipitates with anti-BRCA1 N-terminus (K-18). Five hundred μg of total protein was used in each immunopurification. Molecular weight markers are shown.

To analyze whether BRCA1 was associated with p53 in breast cancer cells, BRCA1 from human diploid HBL-100 mammary epithelial cancer cell lysates [6] was immunoprecipitated with a polyclonal antibody (K-18) against an N-terminus epitope (amino acids 70-89). It was found that BRCA1 was associated with p53 in these cells as detected by western blot using specific antibodies against the N-terminus region of p53 (Bp53-12) (FIG. 1A). This association was increased in HBL-100 (FIG. 1A) and MCF-7 (not shown) breast cancer cells following DNA damage induced by UV-B light irradiation or adriamycin treatment, which stimulates the expression of p53 [19] [38], but did not affect the expression of BRCA1 (not shown). The in vivo BRCA1/p53 association was confirmed using another BRCA1 polyclonal antibody (I-20) against a C-terminus sequence (amino acids 1823-1842 (SEQ ID NO:15) for BRCA1 immunoprecipitation, as well as by reciprocal immunoprecipitation with monoclonal antibodies against p53 (Bp53-12) and subsequent immunoblot for BRCA1. DNA damage also increased the amount of BRCA1 present in p53 immunoprecipitates (FIG. 1B).

Figure 1C:
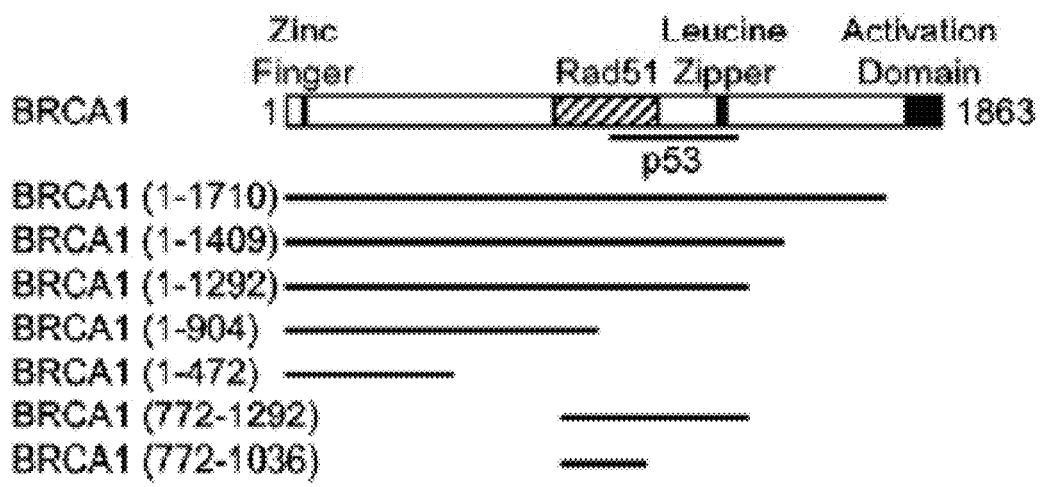
FIG. 1C represents that BRCA1 has a zinc finger, a domain that associates with Rad51, a leucine zipper and an activation domain. The proposed domain interacting with p53 is shown. The indicated C-terminus truncations of BRCA1 were inserted into a pcDNA expression vector, while the N-terminus/C-terminus truncations were inserted into an HA-tag vector [35], as described below.
Figure 1D:
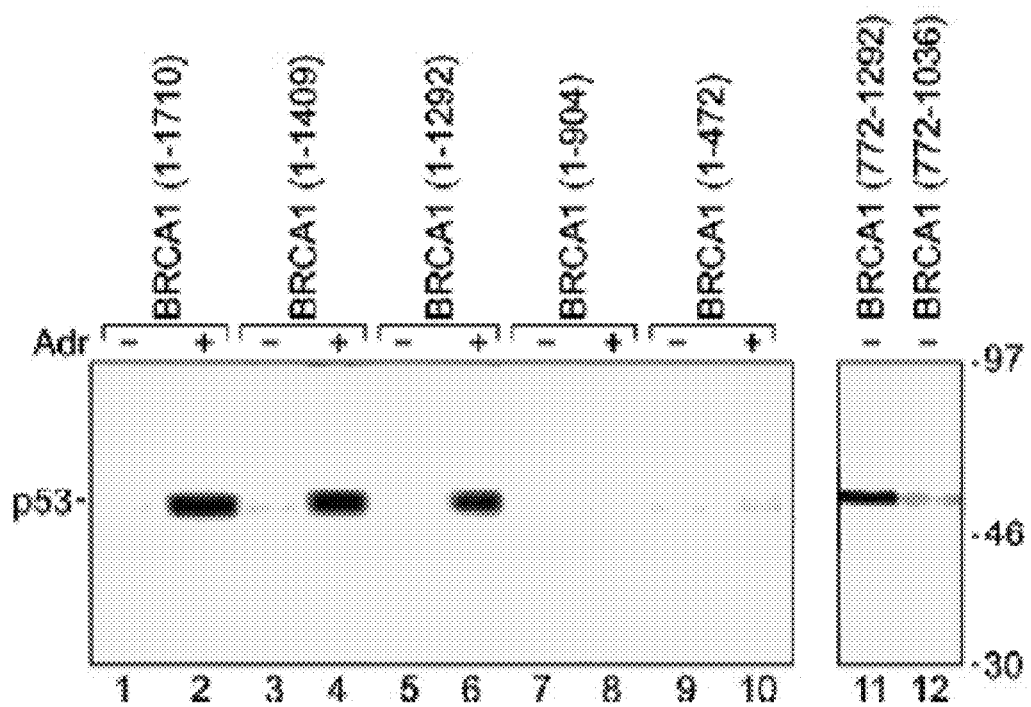
FIG. 1D represents a western blot of p53 in BRCA1 immunoprecipitates. MCF-7 (lanes 1-10) and HBL-100 (lanes 11 and 12) cells were transfected with plasmids expressing truncated BRCA1 proteins. After 24 h, cell lysates were incubated with either anti-BRCA1 N-terminus (K-18) (lanes 1-10), or with purified anti-HA-tag (Y-11; amino acids 98-108; Santa Cruz) (lanes 11 and 12) and precipitated with anti-IgG-sepharose beads [37]. Western blot for p53 was performed using monoclonal p53 antibodies (Bp53-12) as described [37]. Cells in lanes 2, 4, 6, 8 and 10 were treated with adriamycin (Adr) (0.2 μg ml$^{-1}$) for 24 h before harvesting. A representative experiment shows that adriamycin induces the physical association of p53 with BRCA1 (1-1710, SEQ ID NO:4) (lane 2), BRCA1 (1-1409, SEQ ID NO:12)) (lane 4) and BRCA1 (1-1292, SEQ ID NO:5) (lane 6). BRCA1 (772-1292, SEQ ID NO:1) interacts with p53 in the absence of adriamycin treatment (lane 11). In contrast, p53 did not associate with BRCA1 (1-904, SEQ ID NO:6) (lane 8), BRCA1 (1-472, SEQ ID NO:7) (lane 10) and BRCA1 (772-1036, SEQ ID NO:8) (lane 12) either in the absence or presence of adriamycin treatment. Five hundred μg of total protein was used in each immunopurification. Molecular weight markers are shown.

To determine which region of BRCA1 is necessary for its interaction with p53 in vivo, human MCF-7 mammary adenocarcinoma cells, which express wild type p53 [38] was transfected with vectors expressing BRCA1 proteins with progressive deletions of the C-terminus (amino acids 1-1710 (SEQ ID NO:4); amino acids 1-1409 (SEQ ID NO:12); amino acids 1-1292 (SEQ ID NO:5); amino acids 1-904 (SEQ ID NO6); and amino acids 1-472 (SEQ ID NO:7)) (FIG. 1C). The BRCA1 proteins were immunoprecipitated with specific antibodies against an N-terminus epitope (K-18) present in all these proteins. After treatment with adriamycin, p53 was found to be consistently associated with BRCA1 proteins containing deletions of the C-terminus region up to amino acid 1292 [BRCA1 (1-1710) (SEQ NO:4), BRCA1 (1-1409) (SEQ ID NO:12) and BRCA1 (1-1292) (SEQ ID NO:5)] (FIG. 1D). BRCA1 (772-1292) (SEQ ID NO:1) interacts with p53 in the absence of adriamycin treatment (FIG. 1D), suggesting that the mechanisms responsible for the physical interaction are independent of classical genotoxic factors. BRCA1 proteins with further deletions of the C-terminus region [BRCA1 (1-904) (SEQ ID NO:6) and BRCA1 (1-472) (SEQ ID NO:7)] did not associate with p53 even after adriamycin treatment (FIG. 1D).

These studies suggested that the region between amino acids 904 and 1292 (SEQ ID NO:11) could be required for the BRCA1/p53 association in vivo in breast cancer cells. Therefore, segments of the region of interest were expressed as influenza hemagglutinin (HA) fusion proteins [31] in HBL-100 breast cancer cells to determine the domain of BRCA1 that interacts with p53 (FIG. 1C). Following immunoprecipitation with specific antibodies against HA (Y-11, amino acids 98-108), it was found that BRCA1 (772-1292) (SEQ ID NO:1) was associated with p53, while the interaction of BRCA1 (772-1036) (SEQ ID NO:8) with p53 was negligible (FIG. 1D).

Taken together, these studies provide that the region of BRCA1 between amino acids 772-1292 and preferably between 904-1292 is important for its physical interaction with p53. In agreement with the results obtained with BRCA1 deletion constructs, it was found that p53 was associated with the endogenous BRCA1 in a human lymphoblastoid cell line harboring a BRCA 1 germline mutation (Glu 1250ter) that leads to a C-terminus truncation [BRCA1(1-1250) (SEQ ID NO:16)] (MB, unpublished observation).

These results in vivo in breast cancer cells indicate that the BRCA1 domain between amino acid 772 and 1292 binds to p53. Furthermore, these studies also suggests that a major BRCA1/p53 interaction may occur through the segment encompassing amino acids 904 and 1292 of BRCA1 (FIG. 1C). It was also found a putative leucine zipper domain (amino acids 1209-1230) (SEQ ID NO:17) present within the BRCA1 region that associates with p53. An adjacent region of BRCA1 that includes amino acids 758 to 1064 is sufficient to form complexes with Rad51 in vitro [13]. The BRCA1 domains interacting with both Rad51 and p53 are encoded for by exon 11, which is known to be a hotspot for mutations [4] [5].

Congruent with these results, quantitative biophysical measurements indicate that the previously proposed p53-binding regions of BRCA1 [15] [27], either do not bind or bind weakly to p53 [22] [28]. In conclusion, the in vitro studies with truncated proteins may reflect spurious associations between BRCA1 and p53. However, two missense BRCA1 mutations, W1837R and S1841N, previously identified in patients breast and ovarian tumors and located, in the BRCT domain of the BRCA1 gene, might affect binding to p53 in vitro and in tumor cells [39].

A direct physical association between BRCA1 and p53 can further be assessed using quantitative biophysical measurements [22] [28], and/or confocal microscopy studies with fluorescence resonance energy transfer (FRET) to measure molecular proximity between BRCA1 and p53 [40]. Although the crystal structure of human 53BP1 BRCT domains bound to p53 tumor suppressor has been characterized [24] [26] [41], the crystal structure of the interaction between BRCA1 and p53 has not been obtained [28].

Example 2

BRAC1 (772-1292) Induces Apoptosis and p21 Expression in Breast Cancer Cells

Figure 2A:
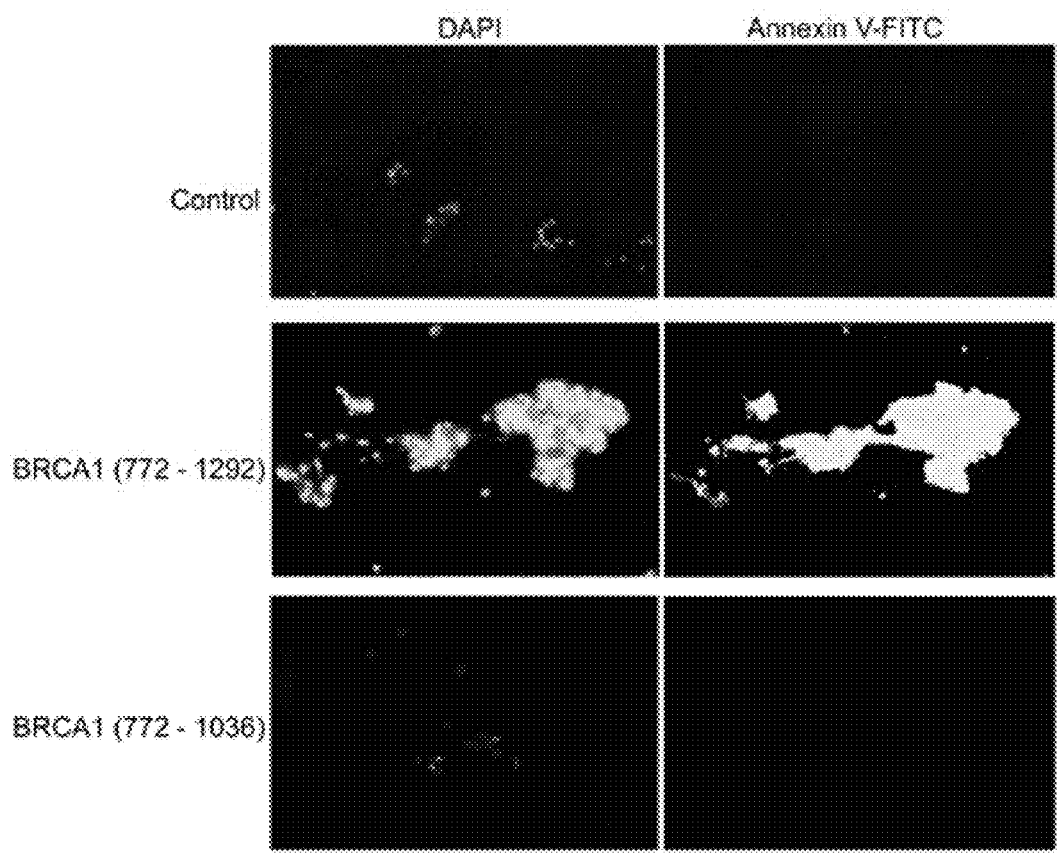
FIG. 2A illustrates that BRCA1 (772-1292, SEQ ID NO:1) induces apoptosis in HBL-100 cells. Cells were untreated (control) or transfected with plasmids expressing control BRCA1 wt, BRCA1 (772-1292, SEQ ID NO:1), and BRCA1 (772-1036, SEQ ID NO:8). Apoptosis was determined by in vivo annexin-V-FITC binding [36] and DNA staining with DAPI [35]. BRCA1 (772-1292, SEQ ID NO:1) induced massive apoptosis (green fluorescence), while BRCA1 wt and BRCA1 (772-1036, SEQ ID NO:8) did not increase apoptosis.
Figure 2B:
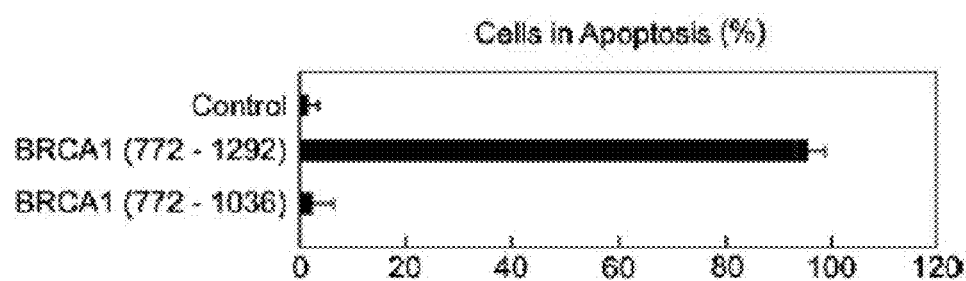
FIG. 2B represents quantitation of apoptosis in HBL-100 cell. Annexin-V-FITC binding was quantified after cell sorting for FITC, using a Kodak 4000 Imaging Station and software. Although the transfection induced a background degree of apoptosis in these cells, expression of BRCA1 (772-1292, SEQ ID No:1) increased more than 10-fold the percentage of cells in apoptosis (P<0.001), while control BRCA1 wt and BRCA1 (772-1036, SEQ ID NO:8) did not increase apoptosis (NS). Values were obtained from three independent experiments.

To analyze the role of the BRCA1/p53 interaction in programmed cell death, HBL-100 cells were transfected with plasmids expressing vectors expressing control BRCA1 wt, BRCA1 (772-1292) (SEQ ID NO:1), and BRCA1 (772-1036) (SEQ ID NO:8). Apoptosis was determined by in vitro annexin-V-FITC binding [36] and DNA staining with DAPI [35]. Annexin-V-FITC binding was quantified after cell sorting for FITC, using a Kodak 4000 Imaging Station and software. Surprisingly, in the absence of genotoxic agents, expression of BRCA1 (772-1292) (SEQ ID NO 1) increased more than 10-fold the percentage of cells in apoptosis ($P<0.001$) (FIG. 2A and 2B). In contrast, expression of control BRCA1 wt or BRCA1(772-1036) (SEQ ID NO:8) had no effect on apoptosis (FIG. 2B), suggesting that interaction between p53 and the region of BRCA1 including amino acids 1036 to 1292 is required to modulate apoptosis. Further studies with siRNA for BCRA1 in HBL-100 cells can be provided.

Figure 2C:
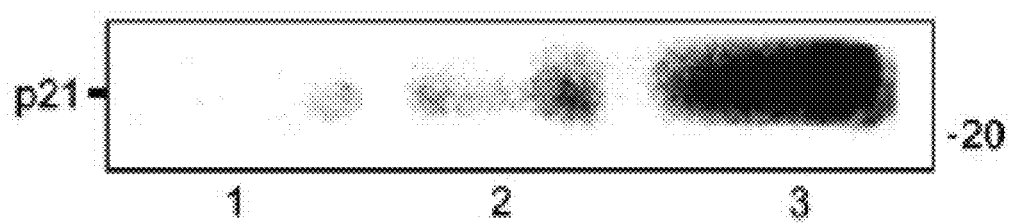
FIG. 2C and 2D represent an expression of p21, cytochrome C, and APAF-1, respectively in HB-100. Cells were transfected as described in FIG. 2A. A p21 immunoblot was performed in immunopurified p21, using purified p21 antibodies (C-19; amino acids 146-164; Santa Cruz) as described previously [33]. Cytochrome C and APAF-1 immunoblots were performed in immunopurified cytochrome C, using specific antibodies. Control BRCA1 wt (lane 1), BRCA1 (772-1292, SEQ ID NO:1) (lane 2), and BRCA1 (772-1036, SEQ ID NO:8) (lane 3) and molecular weight markers are shown (in kD). Immunoblots were quantified using a Kodak 4000 Imaging Station and software. Expression of BRCA1 (772-129.2, SEQ ID NO:1) increased the expression of p21 by 5-fold (P<0.01), and the association of APAF-1 to cytochrome C by 3-fold (P<0.01). Values were obtained from three independent experiments.
Figure 2D:
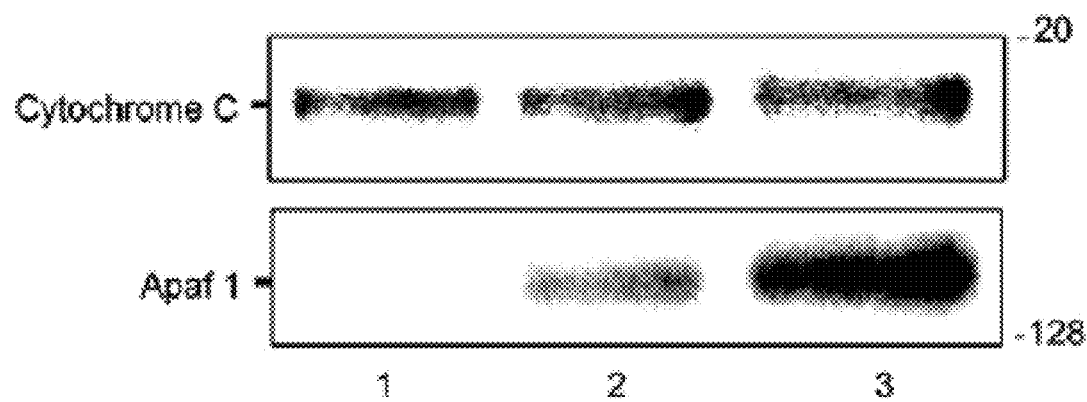

It was reported that after DNA damage, increased synthesis and activity of p53 plays a critical role in p21 expression [19] [20] [21] and in the induction of cell cycle arrest and apoptosis [21] [42] [43]. It was found that expression of BRCA1 (772-1292) stimulated the expression of p21 by 5-fold ($P<0.01$), as shown by the immunoblot immunopurified p21 using specific antibodies (FIG. 2C), whereas neither expression of control BRCA1 wt nor BRCA1 (772-1036) (SEQ ID NO:8) induced p21 expression (NS) (FIG. 2C). These results suggest that BRCA1 (772-1292) (SEQ ID NO:1) facilitates p21 expression, and provide that expression of this peptide or a small peptidomimetic molecule thereof, induces apoptosis in breast tumors resistant to chemotherapeutic agents and radiation.

It is known that apoptotic mitochondrial injury results in the release of cytochrome C into the cytosol, where associates with APAF-1 [44]. The cytochrome C/APAF-1 complex was also detected in immunopurified cytochrome C (FIG. 2C). The expression of APAF-1 associated to cytochrome was increase 3-fold in HBL-100 cells expressing BRCA1 (772-1292) (SEQ ID NO:1) ($P<0.01$) compared to cells expressing control BRCA1 wt or BRCA1 (772-1036) (SEQ ID NO:8) (NS) (FIG. 2C). The increased expression of the cytochrome C/APAF-1 complex is the result in the activation of the initiator caspase 9 in BRCA1 (772-1292) (SEQ ID NO:1) cells [44]. It has been suggested that BRCA1, as a transcriptional co-activator of p53, up-regulates expression of the bax gene, providing a mechanism for apoptosis induction and tumor suppression [15].

Example 3

BRCA1 and p53 Form a Complex with p53 Cognate DNA

Figure 3A:
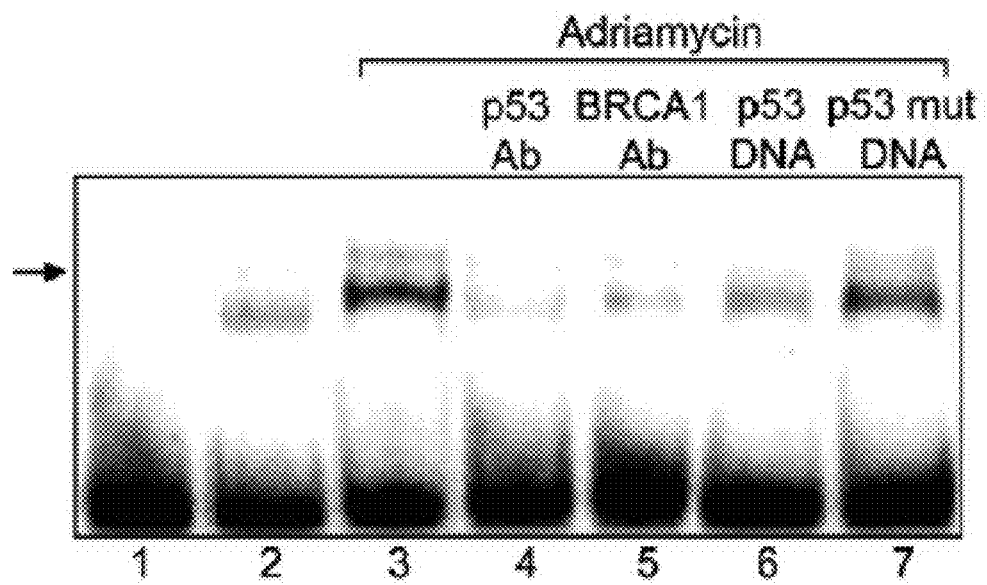
FIG. 3A illustrates that BRCA1 and p53 form a complex with p53 cognate DNA. Mobility shift analysis was performed as described [37]. Equal amounts of nuclear extracts (5 μg of DNA) were incubated with $^{32}$P-labeled p53 consensus oligonucleotide. The position of the bound DNA is indicated by an arrow. Representative examples of HBL-100 cells control (lane 2) or treated with adriamycin (lanes 3-7). Nuclear extracts were incubated with monoclonal p53 antibodies (Bp53-12) (lane 4); purified BRCA1 antibodies (K-18) (lane 5); p53 consensus oligonucleotide (lane 6) or p53 mutant oligonucleotide (lane 7). In lane 1, the probe was processed without nuclear extracts. Adriamycin induced p53 binding activities. Both p53 and BRCA1 participated in the DNA-protein complex as judged by the disruption of the complex with antibodies against p53 and BRCA1.

To determine how the modulation of p21 expression by the BRCA1 is mediated by p53 in breast cancer cells, the p53 binding and transcription activities were analyzed in HBL-100 cells as described previously [29] [33][34] [37]. It was found that adriamycin treatment increased the affinity of nuclear extracts to the p53 cognate sequence within the p21 promoter [20] (FIG. 3A, lanes 2 and 3). Moreover, it was also found that the formation of this complex was disrupted by incubation with antibodies against either p53 (Bp53-12) or BRCA1 (K-18) (FIG. 3A lanes 4 and 5), indicating that these two proteins are physically associated to the p53 consensus DNA. This finding that BRCA1 binds, directly or indirectly, to a specific cognate DNA suggests a role for this tumor suppressor protein in facilitating the assembly of transcriptional factors on target genes. Furthermore, the presence of a leucine zipper (amino acids 1209-1230, SEQ ID NO:17) in the BRCA1 domain that associates with DNA suggests that BRCA1 is a b-Zip protein and that it could form heterodimers with other leucine zipper proteins.

Figure 3B:
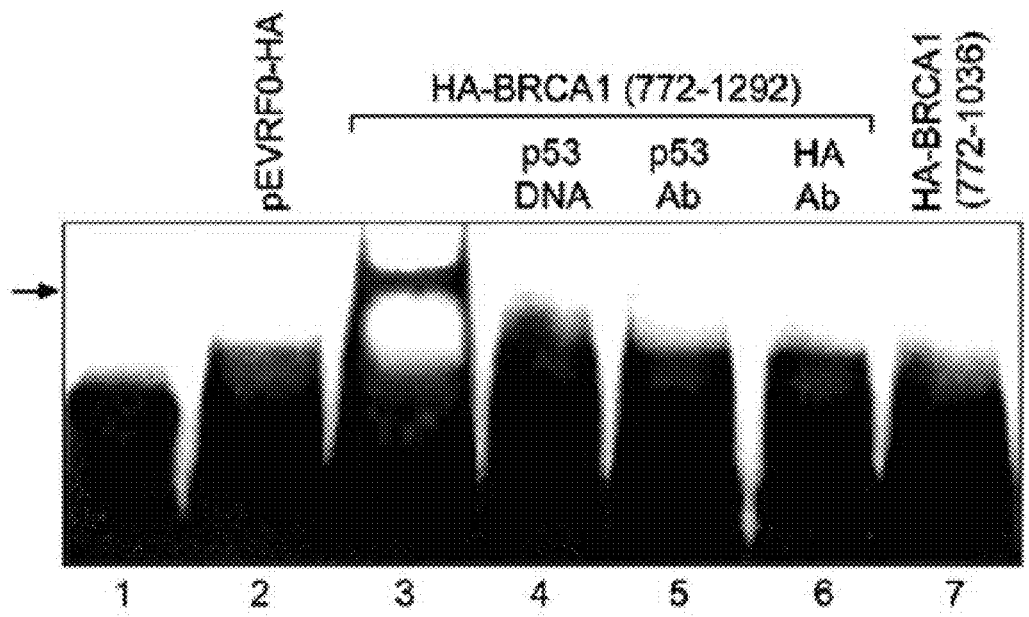
FIG. 3B illustrates that p53 binding activities are increased by BRCA1(772-1292) in HBL-100 cells. Mobility shift analysis was performed as in FIG. 3A. Representative examples of HBL-100 cells transfected with control pEVRFO-HA (lane 2); HA-BRCA1 (772-1292) (lane 3-6); and HA-BRCA1(772-1036, SEQ ID NO:8) (lane 7). Nuclear extracts were incubated with p53 oligonucleotide (lane 4), monoclonal p53 antibodies (Bp53-12) (lane 5); or purified HA antibodies (Y-11) (lane 6). In lane 1, the probe was processed without nuclear extracts. Expression of HA-BRCA1(772-1292, SEQ ID NO:1) stimulated p53 binding activities. Both p53 and HA-tag-BRCA1(772-1292, SEQ ID NO:1) participated in the DNA-protein complex as judged by the disruption of the complex with antibodies against p53 and HA.

Moreover, it was found that formation of the DNA/protein complex was competed effectively by the p53 consensus oligonucleotide (FIG. 3A, lane 6), but not by a mutant oligonucleotide (FIG. 3A, lane 7), which does not bind p53 [20]. In addition, it was also found that transfection of BRCA1 (772-1292) (SEQ ID NO:1) also increased p53 binding activities, albeit less dramatically, in spite of less than 10% of the cells expressing the transfected DNA (FIG. 3B, lane 3). Transfection of the control HA-tag plasmid (pEVRFO-HA), lacking BRCA1 sequences, did not affect DNA binding (FIG. 3B, lane 2). The DNA/protein complex was disrupted by p53 consensus DNA (FIG. 3B, lane 4) and by p53 monoclonal antibodies (Bp53-12) (FIG. 3B, lane 5). Similarly, HA antibodies impaired the formation of the shifted band (FIG. 3B, lane 6), indicating the presence of both p53 and HA-tag-BRCA1 (772-1292) (SEQ ID NO:1) in a functional complex with the p53 consensus oligonucleotide. Congruent with its negligible association with p53 (FIG. 1D), HA-tag-BRCA1 (772-1036) (SEQ ID NO:8) did not affect p53 binding to cognate DNA (FIG. 3B, lane 7).

These findings provide that BRCA1, specifically the domain between amino acids 772 (and preferably, amino acids 904) and 1292, contributes to the enhanced p53 binding affinity to its cognate DNA, after DNA damage in mammary cells.

Example 4

BRCA1 Augmented p53 Transcriptional Activity

Figure 4A:
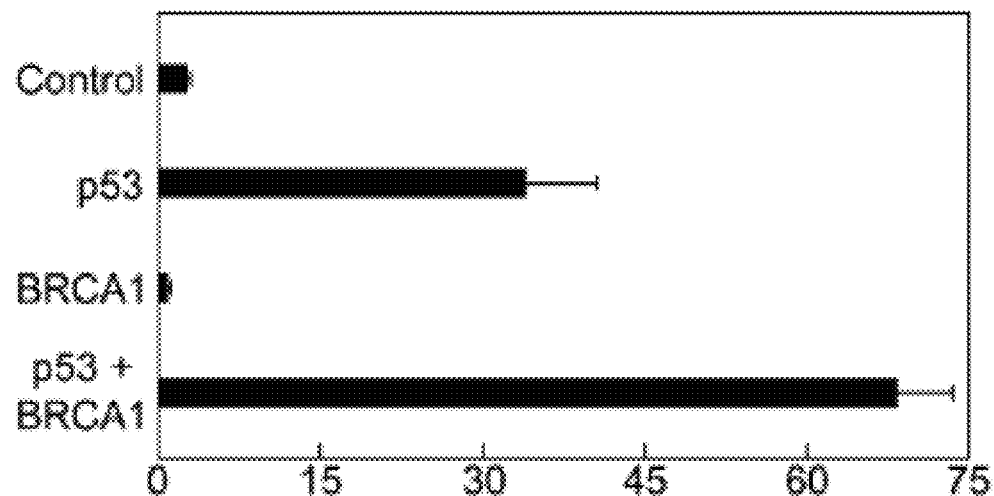
FIG. 4A represents BAX-luciferase (BAX-Luc) expression in p53-/-SAOS cells. Cells were transfected with BAX-Luc or with plasmids expressing pcDNA. BRCA1, and/or p53 as described [29]. Cells were harvested 24 h after transfection and luciferase activity was determined in cell lysates as described [34], and expressed in relative units per mg of cell lysate protein. BAX-Luc expression was stimulated by p53 (P<0.05) and p53 (P<0.01), but not by BRCA1 alone. Values were obtained from three independent experiments.
Figure 4B:
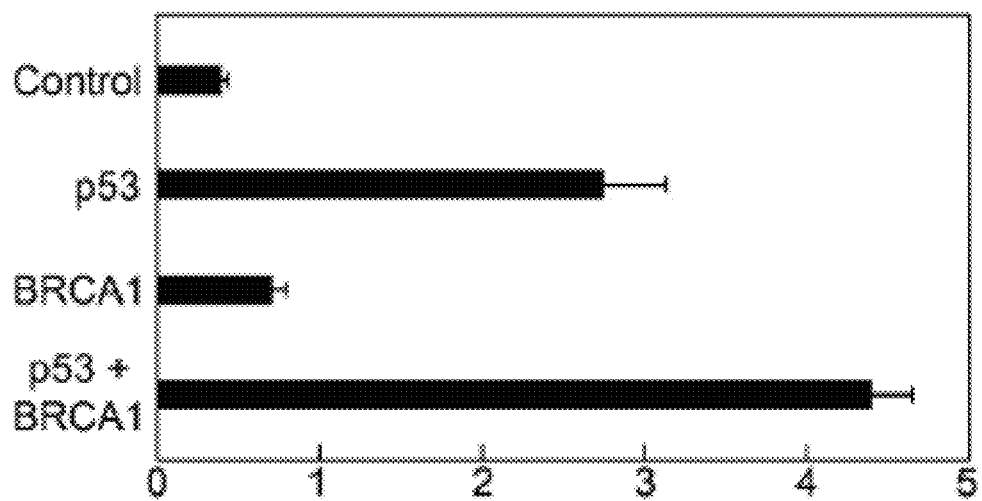
FIG. 4B represents BAX-luciferase expression in p21-/-80S14 cells. Cells were transfected with BAX-Luc or with plasmids expressing pcDNA, BRCA1, and p53. Cells were harvested 24 h after transfection and luciferase activity was determined in cell lysates as described in FIG. 4A. BAX-Luc expression was stimulated by p53 (P<0.05) and p53+BRCA1 (P<0.05), but not by BRCA1 alone. Values were obtained from three independent experiments.
Figure 4C:
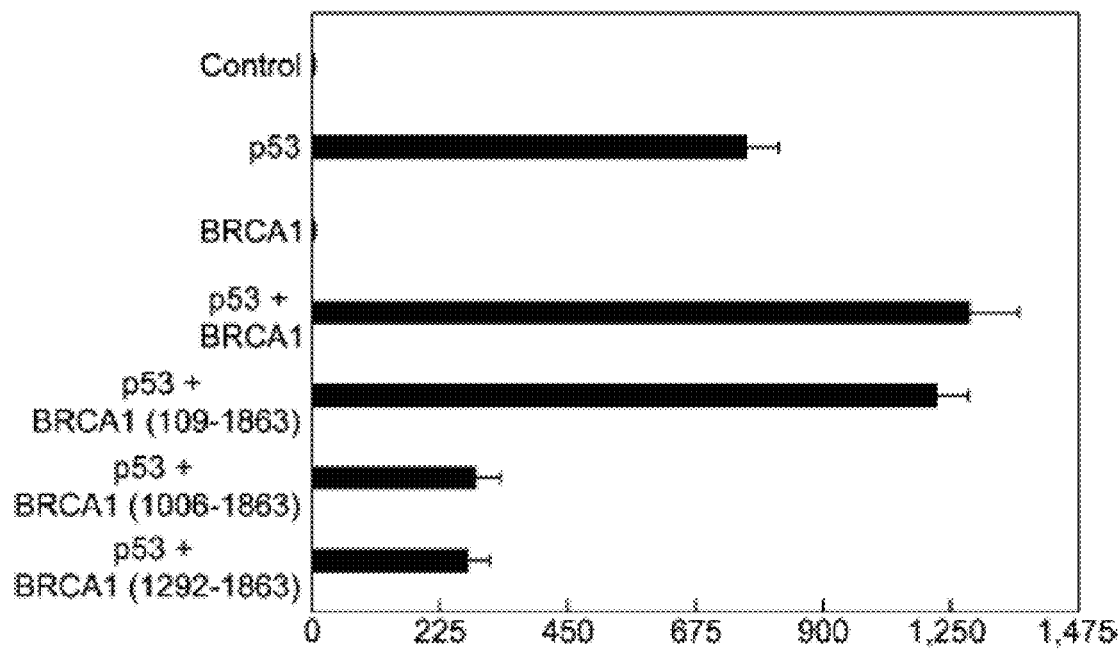
FIG. 4C represents BAX-luciferase expression in MCF-7 cells. Cells were transfected with BAX-Luc or with plasmids expressing pcDNA, BRCA1 and p53. Cells were harvested 24 h after transfection and luciferase activity was determined in cell lysates as described in FIG. 4A. BAX-Luc expression was stimulated by p53 (P<0.001), p53 BRCA1 wt (P<0.001) and p53+BRCA1(109-1863) (SEQ ID NO:13) (P<0.001), but neither by BRCA1 alone nor by p53+BRCA1 (1006-1863) (SEQ ID NO:18) or BRCA1(1292-1863) (SEQ ID NO:14). Values were obtained from three independent experiments.

In agreement with previous studies [15], it was found that BRCA1 augmented p53 transcriptional activity from a BAX-Luc reporter gene [45] both in p53-/-SAOS cells (FIG. 4A) and in p21-/-80S14 cells (FIG. 4B), as described previously [29] [30] [32] [33] [34] [37]. To ascertain whether the expression of p53-responsive genes is augmented by the interaction between specific domains of BRCA1. MCF-7 cells were transfected with the BAX-Luc reporter gene, p53, and various BRCA1 constructs, it was found that the increase in p53- mediated transcription by BRCA1 wt was conserved with a 108 amino acids deletion of the N-terminus, BRCA1 (109-1863) (SEQ ID NO:13), but further deletion of the BRCA1 N-terminus inhibited p53-mediated transcription (BRCA1 [1006-1862] (SEQ ID NO:18) and BRCA1 [1292-1862] (SEQ ID NO:15) (FIG. 4C).

Figure 4D:
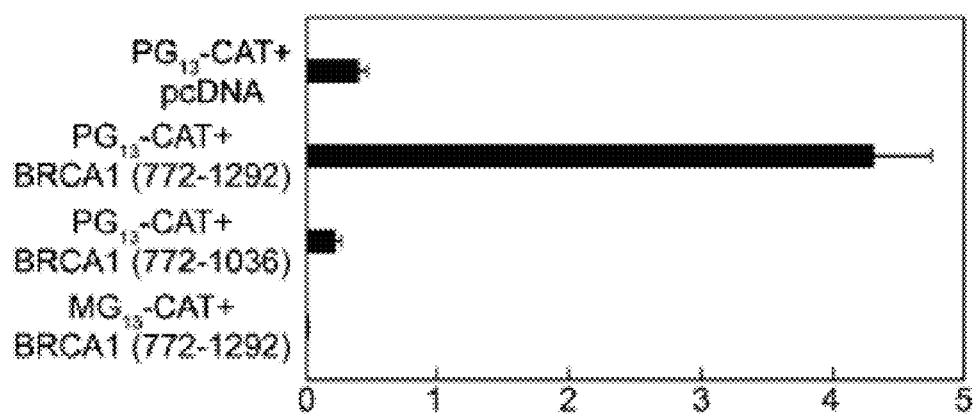
FIG. 4D illustrates $PG_{13}$-CAT protein expression in HBL-100 cells. Cells were transfected with $PG_{13}$-CAT, $MG_{15}$-CAT or with plasmids expressing pcDNA, BRCA1(772-1292) and BRCA1 (772-1036, SEQ ID NO:8), as described [34]. Cells were harvested 24 h after transfection and CAT protein was determined in cell lysates by ELISA as described [34], and expressed in pg per mg of cell lysate protein. $PG_{13}$-CAT expression was stimulated by BRCA1 (772-1292, SEQ ID NO:1) (P<0.01) but not by BRCA1(772-1036, SEQ ID NO:8). The expression from the $MG_{15}$-CAT was not induced by BRCA1 (772-1292, SEQ ID NO:1). Values were obtained from three independent experiments.

In addition, HBL-100 cells were transfected with a p53-responsive, chimeric reporter gene derived from the ribosomal gene cluster clone ($PG_{13}$-CAT) [20], alone or with plasmids expressing various BRCA1 peptides in agreement with the previous experiments, FIG. 4D shows that the expression of $PG_{13}$-CAT was markedly increased by BRCA1 (772-1292) (SEQ ID NO:1), which interacts effectively with p53, but not by BRCA1 (772-1036) (SEQ ID NO:8), which interacts much less effectively with p53. In contrast, expression of BRCA1 (772-1292) (SEQ ID NO:1) did not enhance transcription from a mutated, p53-nonresponsive, control $MG_{15}$-CAT reporter gene [20] (FIG. 4D).

Collectively, these data suggest that after DNA damage, the induction of p21 expression and the subsequent apoptosis is modulated by the interaction between p53 and BRCA1. Of interest, expression of a truncated BRCA1 (772-1292) (SEQ ID NO:1) stimulated p53 binding and transcription activities and apoptosis, recapitulating some effects of DNA damage.

These findings provide additional insights into the mechanisms by which BRCA1 affects transcription and the cellular responses to DNA damage. Dysfunction of the BRCA1 domain that associates with p53, induced by oncogenic pathways or BRCA1 mutations, may confer susceptibility to breast and ovarian cancer.

REFERENCES

[1] K. W. Kinzler and B. Vogelstein, Gatekeepers and caretakers. Nature 386 (1997) 761-763.

[2] Y. Miki, J. Swensen, D. Shattuck-Eidens, P. A. Futreal, K. Harshman, S. Tavtigian. Q. Liu, C. Cochran, and et al, A strong candidate for the breast and ovarian cancer susceptibility gene BRCA1. Science 266 (1994) 66-71.

[3] P. A. Futreal, Q. Liu, D. Shattuck-Eidens, C. Cochran, K. Harshman, S. Tavtigian, L. M. Bennett, A. Haugen-Strano, and et al, BRCA1 mutations in primary breast and ovarian carcinomas. Science 266 (1994) 120-122.

[4] J. P. Struewing, L. C. Brody, M. R. Erdos, R. G. Kase, T. R. Giambarresi, S. A. Smith, F. S. Collins, and M. A. Tucker, Detection of eight BRCA1 mutations in 10 breast/ovarian cancer families, including 1 family with male breast cancer. Am. J. Hum. Genet. 57 (1995) 1-7.

[5] F. J. Couch, M. R. Erdos, K. F. Hoskins, K. Calzone, J. E. Garber, J. Boyd, M. B. Lubin, and et al, Mutations in the BRCA1 gene in families with early-onset breast and ovarian cancer. Nat. Genet. 8 (1994) 387-391.

[6] Y. Chen, C.-F. Chen, D. J. Riley, D. C. Allred, P.-L. Chen, D. Von Hoff, C. K. Osborne, and W.-H. Lee, Aberrant subcellular localization of BRCA1 in breast cancer. Science 270 (1995) 789-791.

[7] E. Rosen, S. Fan, and Y. Ma, BRCA1 regulation of transcription. Cancer Lett 236 (2006) 175-185.

[8] A. N. Monteiro, A. August, and H. Hanafusa, Evidence for a transcriptional activation function of BRCA1 C-terminal region. Proc. Natl. Acad. Sci. USA 93 (1996) 13595-13599.

[9] M. S. Chapman and I. M. Verma, Transcriptional activation by BRCA1. Nature 382 (1996) 678-679.

[10] J. T. Holt, M. E. Thompson, C. Szabo, C. Robinson-Benion, C. L. Arteaga, M.-C. King, and R. A. Jensen, Growth retardation and tumour inhibition by BRCA1. Nat. Genet. 12 (1996) 298-302.

[11] P. Sung, Catalysis of ATP-dependent homologous DNA pairing and strand exchange by yeast RAD51 protein. Science 265 (1994) 1241-1243.

[12] P. Baumann, F. E. Benson, and S. C. West, Human Rad51 protein promotes ATP-dependent homologous pairing and strand transfer reactions in vitro. Cell 87 (1996) 757-766.

[13] R. Scully, J. Chen, A. Plug, Y. Xiao, D. Weaver, J. Feunteun, T. Ashley, and D. M. Livingston, Association of BRCA1 with Rad51 in mitotic and meiotic cells. Cell 88 (1997) 265-275.

[14] K. Somasundaram and W. S. El-Deiry, Inhibition of p53-mediated transactivation and cell cycle arrest by E1A through its p300/CBP-interacting region. Oncogene 14 (1997) 1047-1057.

[15] H. Zhang, K. Somasundaram, Y. Peng, H. Tian, H. Zhang, D. Bi, B. Weber, and W. S. El-Deiry, BRCA1 physically associates with p53 and stimulates its transcriptional activity. Oncogene 16 (1998) 1713-1721.

[16] J. M. Nigro, S. J. Baker, A. C. Preisinger, J. M. Jessup, R. Hostetter, K. Cleary, S. H. Bigner, N. Davidson, and et al, Mutations in the p53 gene occur in diverse human tumour types. Nature 342 (1989) 705-708.

[17] B. Vogelstein and K. W. Kinzler, p53 function and dysfunction. Cell 70 (1992) 523-526.

[18] T. Mummenbrauer, F. Janus, B. Muller, L. Wiesmuller, W. Deppert, and F. Grosse, p53 protein exhibits 3'-to-5' exonuclease activity. Cell 85 (1996) 1089-1099.

[19] T. Waldman, K. W. Kinzler, and B. Vogelstein, p21 is necessary for the p53-mediated $G_1$ arrest in human cancer cells. Cancer Res. 55 (1995) 5187-5190.

[20] W. S. El-Deiry, T. Tokino, V. E. Velculescu, D. B. Levy, R. Parsons, J. M. Trent, D. Lin, W. E. Mercer. K. W. Kinzler, and B. Vogelstein, WAF1, a potential mediator of p53 tumor suppression. Cell 75 (1993) 817-825.

[21] X. Chen, L. J. Ko, L. Jayaraman, and C. Prives, p53 levels, functional domains, and DNA damage determine the extent of the apoptotic response of tumor cells. Genes and Development 10 (1996) 2438-2451.

[22] W. Mark, J. Liao, Y. Lu, A. Ayed, R. Laister, B. Szymczyna, A. Chakrabartty, and C. Arrowsmith, Characterization of segments from the central region of BRCA1: an intrinsically disordered scaffold for multiple protein-protein and protein DNA interactions? J Mol Biol 345 (2005) 275-287.

[23] K. Iwabuchi, P. L. Bartel, B. Li, R. Marraccino, and S. Fields, Two cellular proteins that bind to wild-type but not mutant p53. Proc. Natl. Acad. Sci. USA 91 (1994) 6098-6102.

[24] P. Bork, K. Hofmann, P. Bucher, A. F. Neuwald, S. F. Altschul, and E. V. Koonin, A superfamily of conserved domains in DNA damage-responsive cell cycle checkpoint proteins. The FASEB Journal 11 (1997) 68-76.

[25] I. Callebaut and J.-P. Mornon, From BRCA1 to RAP1: a widespread BRCT module closely associated with DNA repair. FEBS Letters 400 (1997) 25-30.

[26] W. Joo, P. D. Jeffrey, S. Cantor, M. Finnin, D. M. Livingston, and N. P. Pavletich, Structure of the 53BP1 BRCT region bound to p53 and its comparison to the Brca1 BRCT structure. Genes and Development 16 (2002) 583-593.

[27] Y. Chai, J. Cui, N. Shao, E. Shyam, P. Reddy, and V. N. Rao, The second BRCT domain of BRCA1 proteins interacts with p53 and stimulates transcription from the p2WAF1/CIP1 promoter. Oncogene 18 (1999) 263-269.

[28] J. Liu, Y. Pan, B. Ma, and R. Nussinov, "Similarity type" in protein-protein interactions could be carcinogenic: simulations of p53 core domain complexed with 53BP1 and BRCA1 BRCT domains. Structure 14 (2006) 1811-1821.

[29] M. Buck, H. Turler, and M. Chojkier, LAP (NF-IL6), a tissue-specific transcriptional activator, is an inhibitor of hepatoma cell proliferation. EMBO J. 13 (1994) 851-860.

[30] M. Buck, V. Poli, P, van der Geer, M. Chojkier, and T. Hunter, Phosphorylation of rat serine 105 or mouse threonine 217 in C/EBPb is required for hepatocyte proliferation induced by TGFa. Mol. Cell 4 (1999) 1087-1092.

[31] S. J. Morana, C. M. Wolf, J. Li, J. E. Reynolds, and M. K. Brown. The involvement of protein phosphatases in the activation of ICE/CED-3 protease, intracellular acidification. DNA digestion and apoptosis. Journal of Biological Chemistry 271 (1996) 18263-18271.

[32] M. Buck, V. Poli, T. Hunter, and M. Chojkier, C/EBPb phosphorylation by RSK creates a functional XEXD caspase inhibitory box critical for cell survival. Mol. Cell 8 (2001) 807-816.

[33] M. Buck, L. Zhang, T. Hunter, and M. Chojkier, Nuclear export of phosphorylated C/EBPb mediates the inhibition of albumin expression by TNFa. EMBO J. 20 (2001) 6712-6723.

[34] C. Trautwein, C. Caelles. P. van der Geer, T. Hunter, M. Karin, and M. Chojkier, Transactivation by NF-IL6/LAP is enhanced by phosphorylation of its activation domain. Nature 364 (1993) 544-547.

[35] P. Matthias, M. M. Muller, E. Schreiber, S. Rusconi, and W. Schaffner, Eukanyotic expression vectors for the analysis of mutant proteins. Nucleic Acids Res. 17 (1989) 6418.

[36] M. Buck and M. Chojkier, C/EBP(beta) phosphorylation rescues macrophage disfunction and apoptosis induced by anthrax lethal toxin. Am J Physiol Cell Physiol 293 (2007) C1788-C1796.

[37] M. Buck and M. Chojkier, Muscle wasting and dedifferentiation induced by oxidative stress in a murine model of cachexia is prevented by inhibitors of nitric oxide synthesis and antioxidants. EMBO J. 15 (1996) 1753-1765.

[38] Q. Zhan, S. Fan, M. L. Smith, I. Bae, K. Yu, I. Jr. Alamo, P. M. O'Connor, and A. J. Jr. Fornace, Abrogation of p53 function affects gadd gene responses to DNA base-damaging agents and starvation. DNA Cell. Biol. 15 (1996) 805-815.

[39] B. Quaresima, M. G. Faniello, F. Baudi, T. Crugliano, M. Di Sanzo, G. Cuda, F. Costanzo, and S. Venuta, Missense mutations of BRCA1 gene affect the binding with p53 both in vitro and in vivo. Oncol Rep 16 (2006) 811-815.

[40] B. Giepmans, S. Adams, M. Ellisman, and R. Tsien, The fluorescent toolbox for assessing protein location and function. Science 312 (2006) 217-224.

[41] D. Derbyshire, B. Basu, L. Serpell, W. Joo, T. Date, K. Iwabuchi and A. Doherty, Crystal structure of human 53BP1 BRCT domains bound to p53 tumour suppressor. EMBO J. 21 (2002) 3863-3972.

[42] J. Chen, P. K. Jackson, M. W. Kirschner, and A. Dutta, Separate domains of p21 involved in the inhibition of Cdk kinase and PCNA. Nature 374 (1995) 386-388.

[43] Y. Luo, J. Hurwitz, and J. Massague, Cell-cycle inhibition by independent CDK and PCNA binding domains in $p21^{Cip1}$. Nature 375 (1995) 159-161.

[44] D. Spierings, G. McStay, M. Saleh, C. Bender, J. Chipuk, U. Maurer, and D. Green, Connected to death: the (unexpurgated) mitochondrial pathway of apoptosis. Science 310 (2005) 66-67.

[45] T. Miyashita and J. Reed, Tumor suppressor p53 is a direct transcriptional activator of the human bax gene. Cell 80 (1995) 293-299.

[46] H. R. Stennicke and G. S. Salvesen, Biochemical characteristics of caspases-3, -6, -7, and -8. Journal of Biological Chemistry 272 (1997) 25719-25723.

[47] O. Micheau and J. Tschopp, Induction of TNF Receptor I-Mediated Apoptosis via Two Sequential Signaling Complexes. Cell 114 (2003) 181-190.

What is claimed is:

1. A composition comprising an isolated peptide domain of a wild-type BRCA1 protein, said peptide domain consists of the BRCA1 amino acids 772-1292 (SEQ ID NO:1), amino acids 1036-1292 (SEQ ID NO:10), or amino acids 904-1292 (SEQ ID NO:11), wherein said peptide domain stimulates p53 cognate DNA binding and transcription activities, resulting in cell apoptosis in a cancer cell in the presence of p53.

2. The composition of claim 1, wherein said peptide domain consists of the amino acid sequence of SEQ ID NO:1.

3. The composition of claim 1, wherein said peptide domain consists of the amino acid sequence of SEQ ID NO:11.

4. The composition of claim 1, further comprising a pharmaceutically acceptable carrier.

5. A method of stimulating transcription activities resulting in cancer cell apoptosis comprising binding said peptide domain of claim 1 to p53 cognate DNA in a cancer cell in the presence of p53.

6. The method of claim 5, wherein said cancer cell is breast cancer cell.

7. The method of claim 5, wherein said cancer cell is ovarian cancer cell.

8. A method of making the peptide domain of claim 1 comprising recombinantly expressing a nucleic acid encoding said peptide domain.

9. The method of claim 8, wherein said nucleic acid encodes the peptide domain consisting of the amino acid sequence of SEQ ID NO:1.

10. The method of claim 8, wherein said nucleic acid encodes the peptide domain consisting of the amino acid sequence of SEQ ID NO:11.

11. The composition of claim 1, wherein said peptide domain consists of the amino acid sequence of SEQ ID NO:10.

12. The method of claim 5, wherein said peptide domain consists of the amino acid sequence of SEQ ID NO:1.

13. The method of claim 5, wherein said peptide domain consists of the amino acid sequence of SEQ ID NO:10.

14. The method of claim 5, wherein said peptide domain consists of the amino acid sequence of SEQ ID NO:11.

15. The method of claim 8, wherein said nucleic acid encodes the peptide domain consisting of the amino acid sequence of SEQ ID NO:10.

* * * * *